(12) United States Patent
Lopez-Tapia et al.

(10) Patent No.: US 7,776,910 B2
(45) Date of Patent: Aug. 17, 2010

(54) ARYLSULFONYL PYRROLIDINES AS 5-HT$_6$ INHIBITORS

(75) Inventors: Francisco Javier Lopez-Tapia, Union City, CA (US); Lee Edwin Lowrie, Jr., San Jose, CA (US); Dov Nitzan, San Jose, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 452 days.

(21) Appl. No.: 11/983,347

(22) Filed: Nov. 8, 2007

(65) Prior Publication Data

US 2008/0167361 A1 Jul. 10, 2008

Related U.S. Application Data

(60) Provisional application No. 60/858,106, filed on Nov. 9, 2006.

(51) Int. Cl.
*A61K 31/40* (2006.01)
*A61K 31/404* (2006.01)
*C07D 207/04* (2006.01)
*C07D 403/12* (2006.01)

(52) U.S. Cl. ............... 514/428; 548/356.1; 548/361.5; 548/465; 548/570; 514/408; 514/414; 514/415

(58) Field of Classification Search ............ 548/356.1, 548/361.5, 465, 570; 514/408, 414, 415, 514/428

See application file for complete search history.

(56) References Cited

FOREIGN PATENT DOCUMENTS

WO  WO 2004074283  *  9/2004

* cited by examiner

*Primary Examiner*—Golam M Shameem
(74) *Attorney, Agent, or Firm*—Robert C. Hill

(57) ABSTRACT

Compounds of the formula I:

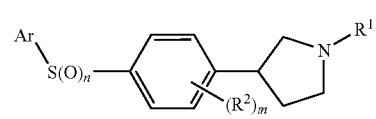

wherein m, n, Ar, R$^1$ and R$^2$ are as defined herein. Methods of making the compounds and using the compounds are disclosed.

16 Claims, No Drawings

ARYLSULFONYL PYRROLIDINES AS 5-HT$_6$ INHIBITORS

CROSS REFERENCE TO RELATED APPLICATIONS

This application claims the benefit of priority of U.S. Provisional Patent Application Ser. No. 60/858,106 filed Nov. 9, 2006, the disclosure of which is incorporated herein by reference in its entirety.

FIELD OF THE INVENTION

This invention relates to substituted pyrrolidine compounds, and associated compositions, methods for use as therapeutic agents, and methods of preparation thereof.

BACKGROUND OF THE INVENTION

The actions of 5-hydroxytryptamine (5-HT) as a major modulatory neurotransmitter in the brain are mediated through a number of receptor families termed 5-HT1, 5-HT2, 5-HT3, 5-HT4, 5-HT5, 5-HT6, and 5-HT7. Based on a high level of 5-HT6 receptor mRNA in the brain, it has been stated that the 5-HT6 receptor may play a role in the pathology and treatment of central nerve system disorders. In particular, 5-HT2-selective and 5-HT6 selective ligands have been identified as potentially useful in the treatment of certain CNS disorders such as Parkinson's disease, Huntington's disease, anxiety, depression, manic depression, psychoses, epilepsy, obsessive compulsive disorders, mood disorders, migraine, Alzheimer's disease (enhancement of cognitive memory), sleep disorders, feeding disorders such as anorexia, bulimia and obesity, panic attacks, akathisia, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. Such compounds are also expected to be of use in the treatment of certain gastrointestinal (GI) disorders such as functional bowel disorder. See for example, B. L. Roth et al., J. Pharmacol. Exp. Ther., 1994, 268, pages 1403-14120, D. R. Sibley et al., Mol. Pharmacol., 1993, 43, 320-327, A. J. Sleight et al., Neurotransmission, 1995, 11, 1-5, and A. J. Sleight et al., Serotonin ID Research Alert, 1997, 2(3), 115-8.

While some 5-HT6 and 5-HT2A modulators have been disclosed, there continues to be a need for compounds that are useful for modulating the 5-HT6 receptor, the 5-HT2A receptor, or both.

SUMMARY

The invention provides compounds of the formula I:

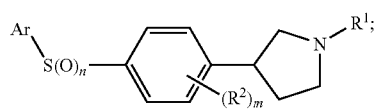

I or a pharmaceutically acceptable salt thereof, wherein:
m is from 0 to 4;
n is from 0 to 2;
Ar is optionally substituted aryl or optionally substituted heteroaryl;
$R^1$ is:
  hydrogen;
  $C_{1-6}$alkyl;
  hetero-$C_{1-6}$alkyl; or
  —(CH$_2$)$_p$—X—(CH$_2$)$_q$—$R^a$;
  wherein:
    X is —C(O)— or —SO$_2$—;
    p and q each independently is 0 or 1; and
    $R^a$ is:
      $C_{1-6}$alkyl;
      $C_{1-6}$alkoxy;
      halo-$C_{1-6}$alkyl;
      halo-$C_{1-6}$alkoxy;
      hydroxy;
      amino;
      N—$C_{1-6}$alkyl-amino; or
      N,N-di-$C_{1-6}$alkylamino; and
each $R^2$ is independently:
  halo;
  $C_{1-6}$alkyl;
  halo-$C_{1-6}$alkyl;
  halo-$C_{1-6}$alkoxy;
  $C_{1-6}$alkoxy;
  hydroxy;
  hetero-$C_{1-6}$alkyl;
  cyano;
  nitro;
  amino;
  N—$C_{1-6}$alkyl-amino;
  N,N-di-$C_{1-6}$alkylamino; or
  —(CH$_2$)$_r$—Y—(CH$_2$)$_s$—Z—(CH$_2$)$_t$—Q-(CH$_2$)$_u$—$R^b$;
  wherein
    r, s, t and u each independently is 0 or 1;
    Z is —C(O)— or —SO$_2$—;
    X and Y each independently is —O—, —NR$^c$— or a bond;
    $R^b$ is:
      hydrogen;
      $C_{1-6}$alkyl;
      halo-$C_{1-6}$alkyl;
      halo-$C_{1-6}$alkoxy;
      $C_{1-6}$alkoxy;
      hydroxy;
      hetero-$C_{1-6}$alkyl;
      cyano;
      amino;
      $C_{1-6}$alkyl-amino; or
      N,N-di-$C_{1-6}$alkylamino; and
    $R^c$ is:
      hydrogen; or
      $C_{1-6}$alkyl.

The invention further provides compositions comprising, methods for making and methods for using the subject compounds.

DETAILED DESCRIPTION OF THE INVENTION

The invention provides substituted quinolinone compounds, associated compositions, methods for use as therapeutic agents, and methods of preparation thereof. In specific embodiments the invention provides piperazinyl-substituted quinolinone compounds and associated pharmaceutical compositions, and methods for using the same in the treatment of central nervous system (CNS) diseases and gastrointestinal tract disorders.

All patents and publications cited in this disclosure are incorporated herein by reference in their entirety. definitions

Unless otherwise stated, the following terms used in this application, including the specification and claims, have the definitions given below. It must be noted that, as used in the specification and the appended claims, the singular forms "a", "an," and "the" include plural referents unless the context clearly dictates otherwise.

"Agonist" refers to a compound that enhances the activity of another compound or receptor site.

"Alkyl" means the monovalent linear or branched saturated hydrocarbon moiety, consisting solely of carbon and hydrogen atoms, having from one to twelve carbon atoms. "Lower alkyl" refers to an alkyl group or moiety of one to six carbon atoms, i.e. $C_1$-$C_6$alkyl. Examples of alkyl groups include, but are not limited to, methyl, ethyl, propyl, isopropyl, isobutyl, sec-butyl, tert-butyl, pentyl, n-hexyl, octyl, dodecyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkenylene" means a linear unsaturated divalent hydrocarbon radical of two to six carbon atoms or a branched saturated divalent hydrocarbon radical of three to six carbon atoms, e.g., ethenylene (—CH=CH—), 2,2-dimethylethenylene, propenylene, 2-methylpropenylene, butenylene, pentenylene, and the like.

"Alkoxy" means a moiety of the formula —OR, wherein R is an alkyl moiety as defined herein. Examples of alkoxy moieties include, but are not limited to, methoxy, ethoxy, isopropoxy, and the like.

"Alkoxyalkyl" means a moiety of the formula —R'—R", where R' is alkylene and R" is alkoxy as defined herein. Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"Alkylcarbonyl" means a moiety of the formula —R'—R", where R' is oxo and R" is alkyl as defined herein.

"Alkylsulfonyl" means a moiety of the formula —R'—R", where R' is —$SO_2$— and R" is alkyl as defined herein.

"Alkylsulfonylalkyl" means a moiety of the formula $R^a$—$SO_2$—$R^b$—, where $R^a$ is alkyl and $R^b$ is alkylene as defined herein. Exemplary alkylsulfonylalkyl groups include, by way of example, 3-methanesulfonylpropyl, 2-methanesulfonylethyl, 2-methanesulfonylpropyl, and the like.

"Aminoalkyl" means a group —R—R' wherein R' is amino and R is alkylene as defined herein. "Aminoalkyl" includes aminomethyl, aminoethyl, 1-aminopropyl, 2-aminopropyl, and the like. The amino moiety of "aminoalkyl" may be substituted once or twice with alkyl to provide "alkylaminoalkyl" and "dialkylaminoalkyl" respectively. "Alkylaminoalkyl" includes methylaminomethyl, methylaminoethyl, methylaminopropyl, ethylaminoethyl and the like. "Dialkylaminoalkyl" includes dimethylaminomethyl, dimethylaminoethyl, dimethylaminopropyl, N-methyl-N-ethylaminoethyl, and the like.

"Amidinyl" means a group of the formula:

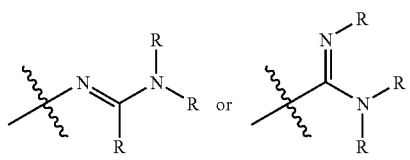

wherein each R independently is hydrogen or alkyl as defined herein.

"Amidinylalkyl" means a group —R—R' wherein R' is amidinyl as defined herein and R is alkylene.

"Amido" means a group —C(O)—NRR' wherein R and R' each independently is hydrogen or alkyl.

"Antagonist" refers to a compound that diminishes or prevents the action of another compound or receptor site.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof. Preferred aryl are phenyl and naphthyl, and more preferably phenyl, which may be optionally substituted as defined herein.

"Aryloxy" means a moiety of the formula —OR, wherein R is an aryl moiety as defined herein.

"Arylalkyl" and "Aralkyl", which may be used interchangeably, mean a radical-$R^aR^b$ where $R^a$ is an alkylene group and $R^b$ is an aryl group as defined herein; e.g., phenylalkyls such as benzyl, phenylethyl, 3-(3-chlorophenyl)-2-methylpentyl, and the like are examples of arylalkyl.

"Aralkoxy" means a moiety of the formula —OR, wherein R is an aralkyl moiety as defined herein.

"Carbamyl" means a group of the formula:

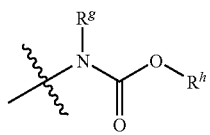

wherein $R^g$ and $R^h$ each independently is hydrogen or alkyl.

"Cyanoalkyl" means a moiety of the formula —R'-R", where R' is alkylene as defined herein and R" is cyano or nitrile.

"Cycloalkyl" means a monovalent saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof.

"Cycloalkylalkyl" means a moiety of the formula —R'-R", where R' is alkylene and R" is cycloalkyl as defined herein.

"Guanidinyl" as used herein means a group of the formula:

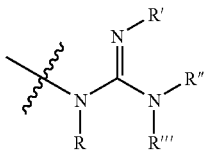

wherein R, R', R" and R'" each independently is hydrogen or alkyl.

"Heteroalkyl" means an alkyl radical as defined herein wherein one, two or three hydrogen atoms have been replaced with a substituent independently selected from the group consisting of —OR$^a$, —NR$^b$R$^c$, and —S(O)$_n$R$^d$ (where n is an integer from 0 to 2), with the understanding that the point of attachment of the heteroalkyl radical is through a carbon atom, wherein R$^a$ is hydrogen, acyl, alkyl, cycloalkyl, or cycloalkylalkyl; R$^b$ and R$^c$ are independently of each other hydrogen, acyl, alkyl, cycloalkyl, or cycloalkylalkyl; and when n is 0, R$^d$ is hydrogen, alkyl, cycloalkyl, or cycloalkylalkyl, and when n is 1 or 2, R$^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof. Preferred heteroaryl include pyridinyl, pyrimidinyl, indolyl, quinolinyl, indazolyl, 1,3-dihydroindolonyl, benzimidazolyl and pyrrolyl, each of which may be optionally substituted as defined herein.

"Heteroaryloxy" means a moiety of the formula —OR, wherein R is a heteroaryl moiety as defined herein.

"Heteroarylalkyl" and "Heteroaralkyl", which may be used interchangeably, mean a radical-R$^a$R$^b$ where R$^a$ is an alkylene group and R$^b$ is a heteroaryl group as defined herein.

"Heteroaralkoxy" means a moiety of the formula —OR, wherein R is a heteroaralkyl moiety as defined herein.

The terms "halo" and "halogen", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —CH$_2$Cl, —CH$_2$CF$_3$, —CH$_2$CCl$_3$, perfluoroalkyl (e.g., —CF$_3$), and the like.

"Haloalkoxy" means a moiety of the formula —OR, wherein R is a haloalkyl moiety as defined herein. Examples of alkoxy moieties include, but are not limited to, methoxy, ethoxy, isopropoxy, and the like.

"Hydroxyalkyl" refers to a subset of heteroalkyl and refers in particular to an alkyl moiety as defined herein that is substituted with one or more, preferably one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl "Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like.

"Heterocyclylalkyl" means a group —R—R' wherein R' is heterocyclyl as defined herein and R is alkylene.

"Imidazolinyl" as used herein means a group of the formula:

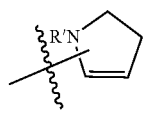

wherein R' is hydrogen or alkyl. Imidazolinyl groups may be optionally substituted as defined herein.

"Imidazolinylalkyl" means a group —R—R' wherein R' is imidazolinyl as defined herein and R is alkylene.

"Imidazolinylaminoalkyl" means a group —R—R'-R" wherein R" is imidazolinyl as defined herein, R' is amino, and R is alkylene. The amino moiety of "imidazolinylaminoalkyl" may be optionally substituted with alkyl.

"Pyrimidinylaminoalkyl" means a group —R—R'-R" wherein R" is pyrimidinyl (preferably pyrimidin-2-yl), R' is amino, and R is alkylene. The pyrimidinyl moiety of "pyrimidinylaminoalkyl" may be optionally substituted as defined herein, and the amino moiety of "pyrimidinylaminoalkyl" may be optionally substituted with alkyl.

"Tetrahydropyrimidinyl" means 1,4,5,6-tetrahydropyrimidinyl, preferably 1,4,5,6-tetrahydropyrimidin-2-yl, and may be optionally substituted as defined herein. "Tetrahydropyrimidinyl" includes 5,5-dimethyl-1,4,5,6-tetrahydropyrimidin-2-yl.

"Tetrahydropyrimidinylaminoalkyl" means a group —R—R'—R" wherein R" is tetrahydropyrimidinyl, R' is amino, and R is alkylene. The amino moiety of "tetrahydropyrimidinylaminoalkyl" may be optionally substituted with alkyl.

"Urea" means a group of the formula:

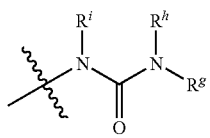

wherein $R^g$, $R^h$ and $R^i$ each independently is hydrogen or alkyl.

"Urealkyl" means a group R—R' wherein R' is urea and R is alkylene.

"Optionally substituted", when used in association with "aryl", "phenyl", "heteroaryl" or "heterocyclyl", means an aryl, phenyl, heteroaryl or heterocyclyl which is optionally substituted independently with one to four substituents, preferably one or two substituents selected from alkyl, cycloalkyl, cycloalkylalkyl, heteroalkyl, hydroxyalkyl, halo, nitro, cyano, hydroxy, alkoxy, amino, acylamino, mono-alkylamino, di-alkylamino, haloalkyl, haloalkoxy, heteroalkyl, —COR (where R is hydrogen, alkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl), or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl). Certain preferred optional substituents for "aryl", "phenyl", "heteroaryl" "cycloalkyl" or "heterocyclyl" include alkyl, halo, haloalkyl, alkoxy, cyano, amino and alkylsulfonyl. More preferred substituents are methyl, fluoro, chloro, trifluoromethyl, methoxy, amino and methanesulfonyl.

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease" and "Disease state" means any disease, condition, symptom, disorder or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include: acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

The terms "pro-drug" and "prodrug", which may be used interchangeably herein, refer to any compound which releases an active parent drug according to formula I in vivo when such prodrug is administered to a mammalian subject. Prodrugs of a compound of formula I are prepared by modifying one or more functional group(s) present in the compound of formula I in such a way that the modification(s) may be cleaved in vivo to release the parent compound. Prodrugs include compounds of formula I wherein a hydroxy, amino, or sulfhydryl group in a compound of Formula I is bonded to any group that may be cleaved in vivo to regenerate the free hydroxyl, amino, or sulfhydryl group, respectively. Examples of prodrugs include, but are not limited to, esters (e.g., acetate, formate, and benzoate derivatives), carbamates (e.g., N,N-dimethylaminocarbonyl) of hydroxy functional groups in compounds of formula I, N-acyl derivatives (e.g. N-acetyl) N-Mannich bases, Schiff bases and enaminones of amino functional groups, oximes, acetals, ketals and enol esters of ketone and aldehyde functional groups in compounds of Formula I, and the like, see Bundegaard, H. "Design of Prodrugs" p 1-92, Elsevier, New York-Oxford (1985), and the like.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. Persons skilled in the art will know how to choose a group for the ease of removal and for the ability to withstand the following reactions.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Treating" or "treatment" of a disease state includes:
(i) preventing the disease state, i.e. causing the clinical symptoms of the disease state not to develop in a subject that may be exposed to or predisposed to the disease state, but does not yet experience or display symptoms of the disease state.
(ii) inhibiting the disease state, i.e., arresting the development of the disease state or its clinical symptoms, or
(iii) relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature and Structures

In general, the nomenclature used in this Application is based on AUTONOM™ v.4.0, a Beilstein Institute computerized system for the generation of IUPAC systematic nomenclature. Chemical structures shown herein were prepared using ISIS® version 2.2. Any open valency appearing on a carbon, oxygen, sulfur or nitrogen atom in the structures herein indicates the presence of a hydrogen atom.

Compounds

The invention provides compounds of the formula I:

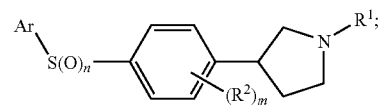

or a pharmaceutically acceptable salt thereof, wherein:
m is from 0 to 4;
n is from 0 to 2;
Ar is optionally substituted aryl or optionally substituted heteroaryl;
$R^1$ is:
  hydrogen;
  $C_{1-6}$alkyl;
  hetero-$C_{1-6}$alkyl; or
  —$(CH_2)_p$—X—$(CH_2)_q$—$R^a$;
  wherein:
    X is —C(O)— or —$SO_2$—;
    p and q each independently is 0 or 1; and
    $R^a$ is:
      $C_{1-6}$alkyl;
      $C_{1-6}$alkoxy;
      halo-$C_{1-6}$alkyl;
      halo-$C_{1-6}$alkoxy;
      hydroxy;
      amino;
      N—$C_{1-6}$alkyl-amino; or
      N,N-di-$C_{1-6}$alkylamino; and
each $R^2$ is independently:
  halo;
  $C_{1-6}$alkyl;
  halo-$C_{1-6}$alkyl;
  halo-$C_{1-6}$alkoxy;
  $C_{1-6}$alkoxy;
  hydroxy;
  hetero-$C_{1-6}$alkyl;
  cyano;
  nitro;
  amino;
  N—$C_{1-6}$alkyl-amino;
  N,N-di-$C_{1-6}$alkylamino; or
  —$(CH_2)_r$—Y—$(CH_2)_s$—Z—$(CH_2)_t$-Q-$(CH_2)_u$—$R^b$;
  wherein
    r, s, t and u each independently is 0 or 1;
    Z is —C(O)— or —$SO_2$—;
    X and Y each independently is —O—, —$NR^c$— or a bond;
    $R^b$ is:
      hydrogen;
      $C_{1-6}$alkyl;
      halo-$C_{1-6}$alkyl;
      halo-$C_{1-6}$alkoxy;
      $C_{1-6}$alkoxy;
      hydroxy;
      hetero-$C_{1-6}$alkyl;
      cyano;
      amino;
      $C_{1-6}$alkyl-amino; or
      N,N-di-$C_{1-6}$alkylamino; and $R^c$ is:
hydrogen; or
$C_{1-6}$alkyl.

It should be understood that the scope of this invention encompasses not only the various isomers which may exist but also the various mixture of isomers which may be formed. Furthermore, the scope of the invention also encompasses solvates, salts and prodrugs of the subject compounds.

In certain embodiments of formula I, n is 0.
In certain embodiments of formula I, n is 1.
In certain embodiments of formula I, n is 2.
In certain embodiments of formula I, Ar is aryl.
In certain embodiments of formula I, Ar is optionally substituted phenyl.
In certain embodiments of formula I, Ar is phenyl optionally substituted once or twice with any of halo, $C_{1-6}$alkyl, halo-$C_{1-6}$alkyl, halo-$C_{1-6}$alkoxy, $C_{1-6}$alkoxy, hydroxy, hetero-$C_{1-6}$alkyl, cyano, nitro, amino, N—$C_{1-6}$alkyl-amino, N,N-di-$C_{1-6}$alkylamino, or —$(CH_2)_w$—$S(O)_x$—$R^d$, wherein w is 0 or 1, x is from 0 to 2, and $R^d$ is hydrogen, $C_{1-6}$alkyl, halo-$C_{1-6}$alkyl, hydroxy, hetero-$C_{1-6}$alkyl, amino, $C_{1-6}$alkyl-amino, or N,N-di-$C_{1-6}$alkylamino.

In certain embodiments of formula I, Ar is phenyl optionally substituted once or twice with halo, $C_{1-6}$alkyl, $C_{1-6}$alkoxy, cyano or hydroxy.

In certain embodiments of formula I, Ar is phenyl substituted with halo, $C_{1-6}$alkyl, $C_{1-6}$alkoxy, cyano or hydroxy.

In certain embodiments of formula I, Ar is heteroaryl.
In certain embodiments of formula I, Ar is heteroaryl selected from indolyl, indazolyl, benzimidazolyl, pyridyl, pyrimidinyl, dihydroindolonyl, quinolinyl and pyrrolyl, each optionally substituted.

In certain embodiments of formula I, Ar is heteroaryl selected from indolyl, indazolyl, benzimidazolyl, pyridyl, pyrimidinyl, dihydroindolonyl, quinolinyl and pyrrolyl, each optionally substituted once or twice with any of halo, $C_{1-6}$alkyl, halo-$C_{1-6}$alkyl, halo-$C_{1-6}$alkoxy, $C_{1-6}$alkoxy, hydroxy, hetero-$C_{1-6}$alkyl, cyano, nitro, amino, N—$C_{1-6}$alkyl-amino, N,N-di-$C_{1-6}$alkylamino, or —$(CH_2)_w$—$S(O)_x$—$R^d$, wherein w is 0 or 1, x is from 0 to 2, and $R^d$ is hydrogen, $C_{1-6}$alkyl, halo-$C_{1-6}$alkyl, hydroxy, hetero-$C_{1-6}$alkyl, amino, $C_{1-6}$alkyl-amino, or N,N-di-$C_{1-6}$alkylamino.

In certain embodiments of formula I, Ar is indolyl, indazolyl, quinolinyl, pyrrolyl, pyridinyl, pyrimidinyl and dihydroindolonyl, each optionally substituted once or twice with any of halo, $C_{1-6}$alkyl, $C_{1-6}$alkoxy, cyano or hydroxy.

In certain embodiments of formula I, Ar is optionally substituted indolyl.
In certain embodiments of formula I, Ar is optionally substituted indazolyl.
In certain embodiments of formula I, Ar is optionally substituted indol-3-yl.
In certain embodiments of formula I, Ar is optionally substituted indol-5-yl.
In certain embodiments of formula I, Ar is optionally substituted indazol-3-yl.
In certain embodiments of formula I, Ar is optionally substituted indazol-5-yl.
In certain embodiments of formula I, $R^1$ is hydrogen or $C_{1-6}$alkyl.
In certain embodiments of formula I, m is 0 or 1.
In certain embodiments of formula I, $R^2$ is $C_{1-6}$alkyl, $C_{1-6}$alkoxy, hydroxy, halo or cyano.
In certain embodiments of formula I, $R^2$ is halo, $C_{1-6}$alkyl, $C_{1-6}$alkoxy, hydroxy, hydroxy-$C_{1-6}$alkyl, hydroxy-$C_{1-6}$alkyl, cyano, —O—C(O)—$R^b$, —O—$CH_2$—C(O)—$R^b$, —C(O)—$R^b$ or —$CH_2$—C(O)—$R^b$.

In certain embodiments of formula I, $R^1$ is —$(CH_2)_p$—X—$(CH_2)_q$—$R^a$.
In certain embodiments of formula I, $R^1$ is —$CH_2$—C(O)—$R^a$.
In certain embodiments of formula I, $R^1$ is —C(O)—$R^a$.
In certain embodiments of formula I, $R^1$ is —$SO_2$—$R^a$.
In certain embodiments of formula I, n is 2 and Ar is optionally substituted phenyl.
In certain embodiments of formula I, n is 2, Ar is optionally substituted phenyl, and m is 0 or 1.
In certain embodiments of formula I, n is 2, Ar is optionally substituted phenyl, m is 0 or 1, and $R^2$ is $C_{1-6}$alkyl, $C_{1-6}$alkoxy, hydroxy, halo or cyano.
In certain embodiments of formula I, n is 2, Ar is optionally substituted phenyl, m is 0 or 1, $R^2$ is $C_{1-6}$alkyl, $C_{1-6}$alkoxy, hydroxy, halo or cyano, and $R^1$ is hydrogen or $C_{1-6}$alkyl.

In certain embodiments of the invention the subject compounds are of the formula II:

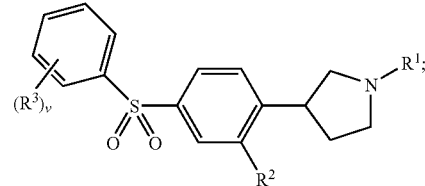

II wherein:
v is from 1 to 4;
each $R^3$ is independently:
halo;
$C_{1-6}$alkyl;
halo-$C_{1-6}$alkyl;
halo-$C_{1-6}$alkoxy;
$C_{1-6}$alkoxy;
hydroxy;
hetero-$C_{1-6}$alkyl;
cyano;
nitro;
amino;
N—$C_{1-6}$alkyl-amino;
N,N-di-$C_{1-6}$alkylamino; or
—$(CH_2)_w$—$S(O)_x$—$R^d$;
wherein:
w is 0 or 1;
x is from 0 to 2;
$R^d$ is:
hydrogen;
$C_{1-6}$alkyl;
halo-$C_{1-6}$alkyl;
hydroxy;
hetero-$C_{1-6}$alkyl;
amino;
$C_{1-6}$alkyl-amino; or
N,N-di-$C_{1-6}$alkylamino; and
$R^1$ and $R^2$ are as defined herein.

In certain embodiments the compounds may be of formula IIa or formula IIb;

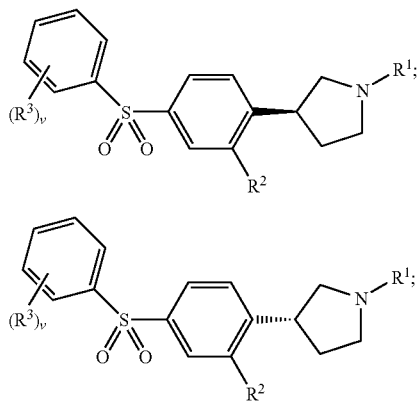

wherein v, $R^1$, $R^2$ and $R^3$ are as defined herein.

In certain embodiments of formula II, formula Ia or formula IIb, $R^1$ is hydrogen or $C_{1-6}$alkyl.

In certain embodiments of formula II, formula Ia or formula IIb, $R^2$ is $C_{1-6}$alkyl, $C_{1-6}$alkoxy, hydroxy, halo or cyano.

In certain embodiments of formula II, formula Ia or formula IIb, $R^2$ is hydrogen, $C_{1-6}$alkyl, $C_{1-6}$alkoxy, $C_{1-6}$alkylsulfanyl, $C_{1-6}$alkylsulfonyl, hydroxy, halo or cyano.

In certain embodiments of formula II, formula Ia or formula IIb, $R^2$ is $C_{1-6}$alkyl, $C_{1-6}$alkoxy, $C_{1-6}$alkylsulfanyl, $C_{1-6}$alkylsulfonyl, hydroxy, halo or cyano.

In certain embodiments of formula II, formula IIa or formula IIb, $R^3$ is $C_{1-6}$alkyl, $C_{1-6}$alkoxy, $C_{1-6}$alkylsulfanyl, $C_{1-6}$alkylsulfonyl, hydroxy, halo or cyano.

In certain embodiments of formula II, formula IIa or formula IIb, $R^2$ is halo, $C_{1-6}$alkyl, $C_{1-6}$alkoxy, hydroxy, hydroxy-$C_{1-6}$alkoxy, hydroxy-$C_{1-6}$alkyl, cyano, —O—C(O)—$R^b$, —O—CH$_2$—C(O)—$R^b$, —C(O)—$R^b$ or —CH$_2$—C(O)—$R^b$.

In certain embodiments of formula II, formula IIa or formula IIb, v is 0, 1 or 2, $R^2$ and $R^3$ each independently is $C_{1-6}$alkyl, $C_{1-6}$alkoxy, $C_{1-6}$alkylsulfanyl, $C_{1-6}$alkylsulfonyl, hydroxy, halo or cyano, and $R^1$ is hydrogen or $C_{1-6}$alkyl.

Where any of $R^1$, $R^2$, $R^3$, $R^4$, $R^5$, $R^6$, $R^a$, $R^b$, $R^c$ and $R^d$ are alkyl or contain an alkyl moiety, such alkyl is preferably lower alkyl, i.e. $C_1$-$C_6$alkyl, and more preferably $C_1$-$C_4$alkyl.

Representative compounds in accordance with the invention are shown in Table 1.

TABLE 1

| # | Structure | Name (Autonom ™) | MP/M + H |
|---|---|---|---|
| 1 | 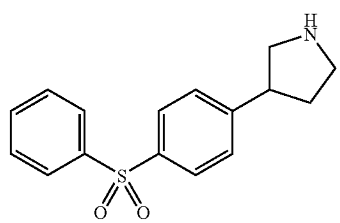 | 3-(4-Benzenesulfonyl-phenyl)-pyrrolidine | 102.4-105.2° C. |
| 2 | 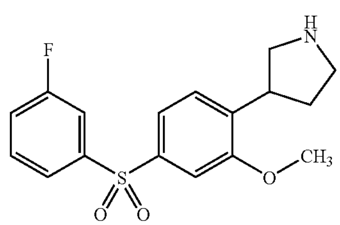 | 3-[4-(3-Fluoro-benzenesulfonyl)-2-methoxy-phenyl]-pyrrolidine | 177.3-178.2° C. |
| 3 | 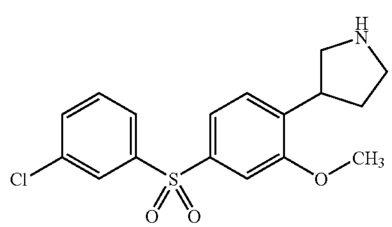 | 3-[4-(3-Chloro-benzenesulfonyl)-2-methoxy-phenyl]-pyrrolidine | 157.3-157.8° C. (HCl Salt) |
| 4 | 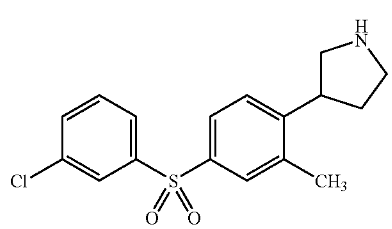 | 3-[4-(3-Chloro-benzenesulfonyl)-2-methyl-phenyl]-pyrrolidine | 336 |

TABLE 1-continued

| # | Structure | Name (Autonom ™) | MP/M + H |
|---|---|---|---|
| 5 | 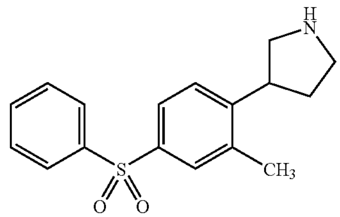 | 3-(4-Benzenesulfonyl-2-methyl-phenyl)-pyrrolidine | 302 |
| 6 | 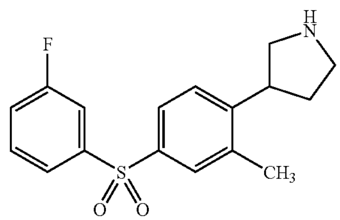 | 3-[4-(3-Fluoro-benzenesulfonyl)-2-methyl-phenyl]-pyrrolidine | 320 |
| 7 | 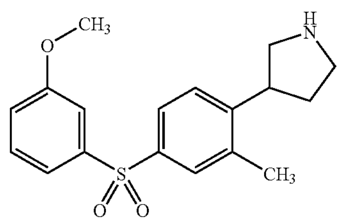 | 3-[4-(3-Methoxy-benzenesulfonyl)-2-methyl-phenyl]-pyrrolidine | 332 |
| 8 | 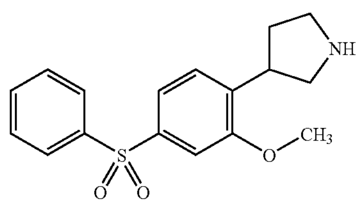 | 3-(4-Benzenesulfonyl-2-methoxy-phenyl)-pyrrolidine | 68.7-70.0° C. (HCl salt) |
| 9 | 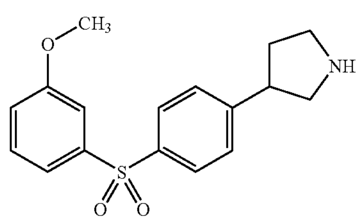 | 3-[4-(3-Methoxy-benzenesulfonyl)-phenyl]-pyrrolidine | 318 |
| 10 | 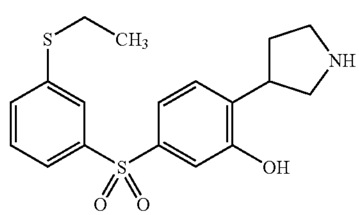 | 5-(3-Ethylsulfanyl-benzenesulfonyl)-2-pyrrolidin-3-yl-phenol | 65.1-70.0° C. |
| 11 | 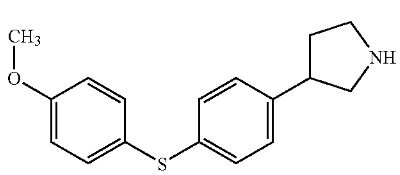 | 3-[4-(4-Methoxy-phenylsulfanyl)-phenyl]-pyrrolidine | 130.0-131.0° C. |

TABLE 1-continued

| # | Structure | Name (Autonom ™) | MP/M + H |
|---|---|---|---|
| 12 | 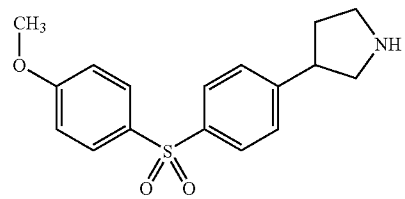 | 3-[4-(4-Methoxy-benzenesulfonyl)-phenyl]-pyrrolidine | 145.6-146.3° C. |
| 13 | 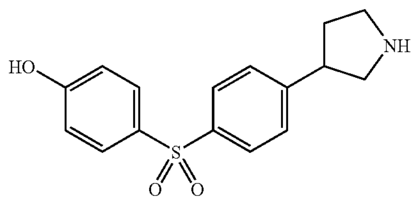 | 4-(4-Pyrrolidin-3-yl-benzenesulfonyl)-phenol | 304 |
| 14 | 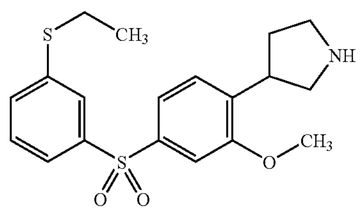 | 3-[4-(3-Ethylsulfanyl-benzenesulfonyl)-2-methoxy-phenyl]-pyrrolidine | 378 |
| 15 | 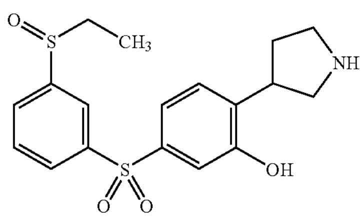 | 5-(3-Ethanesulfinyl-benzenesulfonyl)-2-pyrrolidin-3-yl-phenol | 380 |
| 16 | 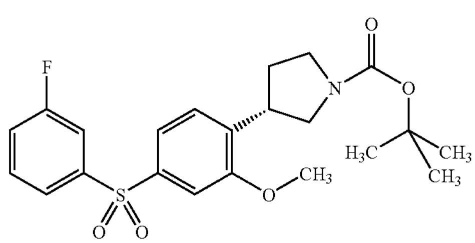 | 3-[4-(3-Fluoro-benzenesulfonyl)-2-methoxy-phenyl]-(S)-pyrrolidine-1-carboxylic acid tert-butyl ester | 436 |
| 17 | 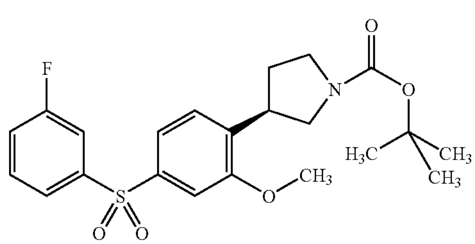 | 3-[4-(3-Fluoro-benzenesulfonyl)-2-methoxy-phenyl]-(R)-pyrrolidine-1-carboxylic acid tert-butyl ester | 436 |
| 18 | 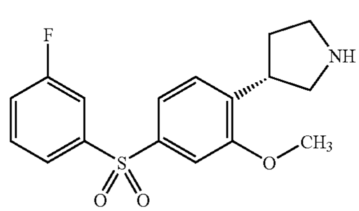 | 3-[4-(3-Fluoro-benzenesulfonyl)-2-methoxy-phenyl]-(S)-pyrrolidine | 336 |

TABLE 1-continued

| # | Structure | Name (Autonom ™) | MP/M + H |
|---|-----------|------------------|----------|
| 19 | 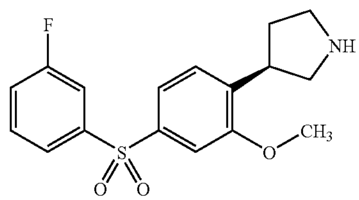 | 3-[4-(3-Fluoro-benzenesulfonyl)-2-methoxy-phenyl]-(R)-pyrrolidine | 336 |
| 20 | 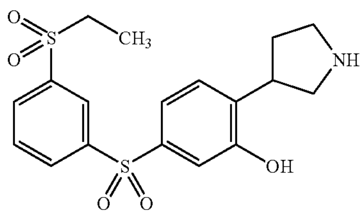 | 5-(3-Ethanesulfonyl-benzenesulfonyl)-2-pyrrolidin-3-yl-phenol | 124.5-126.7° C. (HCl Salt) |
| 21 | 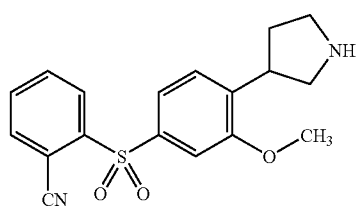 | 2-(3-Methoxy-4-pyrrolidin-3-yl-benzenesulfonyl)-benzonitrile | 247.8-249.1° C. (HCl Salt) |
| 22 | 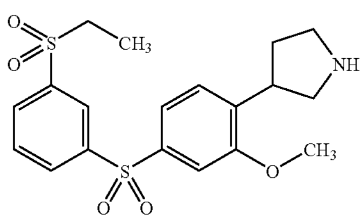 | 3-[4-(3-Ethanesulfonyl-benzenesulfonyl)-2-methoxy-phenyl]-pyrrolidine | 98.5-100.0° C. (HCl Salt) |
| 23 | 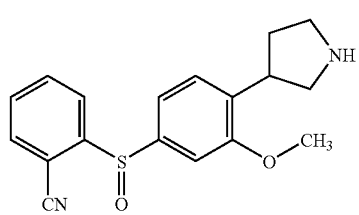 | 2-(3-Methoxy-4-pyrrolidin-3-yl-benzenesulfinyl)-benzonitrile | 79.9-82.0° C. (HCl Salt) |
| 24 | 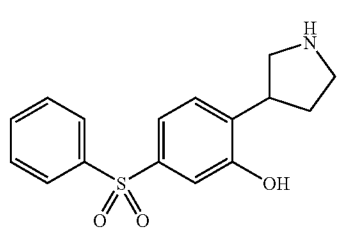 | 5-Benzenesulfonyl-2-pyrrolidin-3-yl-phenol | 304 |
| 25 | 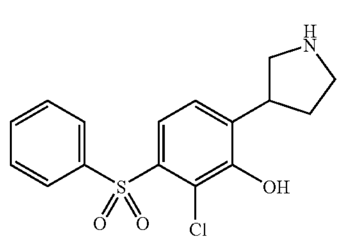 | 3-Benzenesulfonyl-2-chloro-6-pyrrolidin-3-yl-phenol | 338 |

TABLE 1-continued

| # | Structure | Name (Autonom ™) | MP/M + H |
|---|---|---|---|
| 26 | 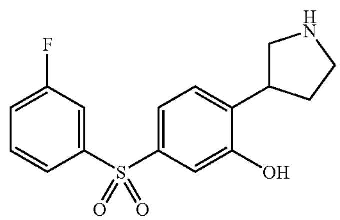 | 5-(3-Fluoro-benzenesulfonyl)-2-pyrrolidin-3-yl-phenol | 322 |
| 27 | 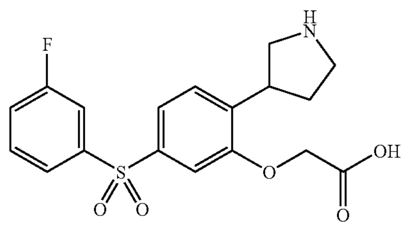 | [5-(3-Fluoro-benzenesulfonyl)-2-pyrrolidin-3-yl-phenoxy]-acetic acid | 380 |
| 28 | 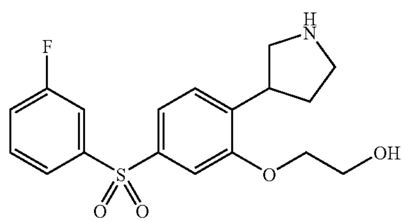 | 2-[5-(3-Fluoro-benzenesulfonyl)-2-pyrrolidin-3-yl-phenoxy]-ethanol | 366 |
| 29 | 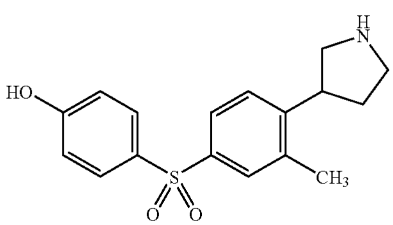 | 4-(3-Methyl-4-pyrrolidin-3-yl-benzenesulfonyl)-phenol | 170.1-173.5° C. (HCl Salt) |
| 30 | 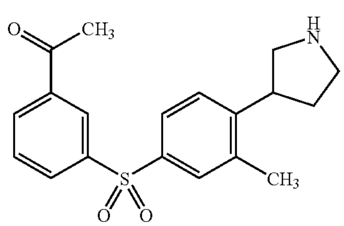 | 1-[3-(3-Methyl-4-pyrrolidin-3-yl-benzenesulfonyl)-phenyl]-ethanone | 344 |
| 31 | 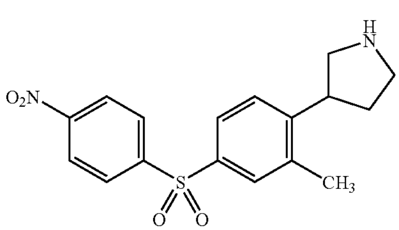 | 3-[2-Methyl-4-(4-nitro-benzenesulfonyl)-phenyl]-pyrrolidine | 269.9-272.5° C. (HCl Salt) |
| 32 | 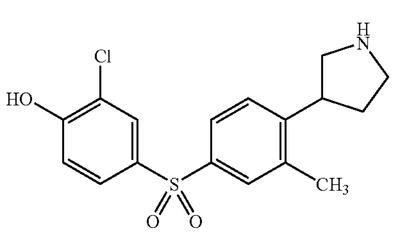 | 2-Chloro-4-(3-methyl-4-pyrrolidin-3-yl-benzenesulfonyl)-phenol | 110.0-112.9° C. (HCl Salt) |

TABLE 1-continued

| # | Structure | Name (Autonom ™) | MP/M + H |
|---|-----------|------------------|----------|
| 33 | 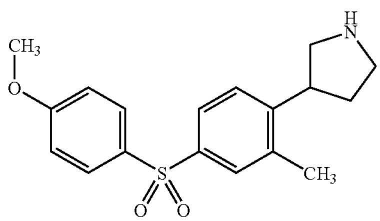 | 3-[4-(4-Methoxy-benzenesulfonyl)-2-methyl-phenyl]-pyrrolidine | 332 |
| 34 | 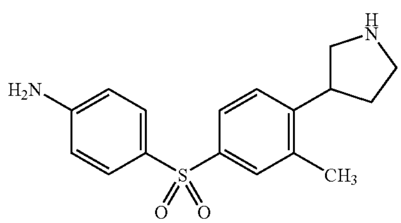 | 4-(3-Methyl-4-pyrrolidin-3-yl-benzenesulfonyl)-phenylamine | 317 |
| 35 | 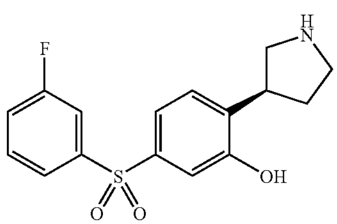 | 5-(3-Fluoro-benzenesulfonyl)-2-(S)-pyrrolidin-3-yl-phenol | 239.0-241.0° C. (HCl Salt) |
| 36 | 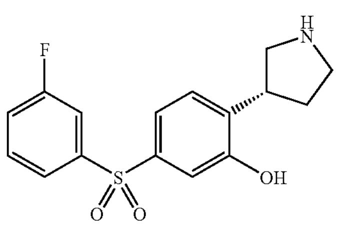 | 5-(3-Fluoro-benzenesulfonyl)-2-(R)-pyrrolidin-3-yl-phenol | 223.0-224.1° C. (HCl Salt) |
| 37 | 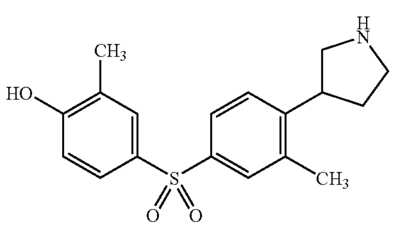 | 2-Methyl-4-(3-methyl-4-pyrrolidin-3-yl-benzenesulfonyl)-phenol | 332 |
| 38 | 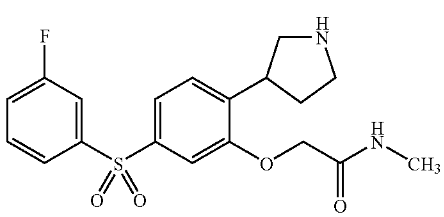 | 2-[5-(3-Fluoro-benzenesulfonyl)-2-pyrrolidin-3-yl-phenoxy]-N-methyl-acetamide | 393 |

TABLE 1-continued

| # | Structure | Name (Autonom ™) | MP/M + H |
|---|---|---|---|
| 39 | 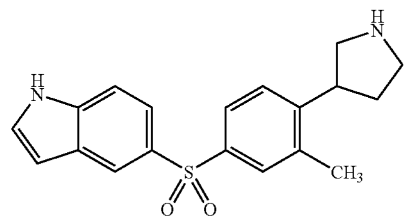 | 5-(3-Methyl-4-pyrrolidin-3-yl-benzenesulfonyl)-1H-indole | 341 |
| 40 | 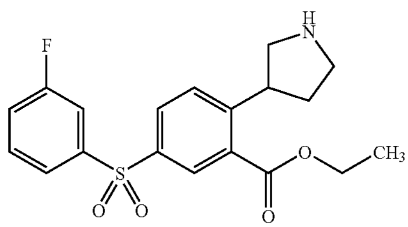 | 5-(3-Fluoro-benzenesulfonyl)-2-pyrrolidin-3-yl-benzoic acid ethyl ester | 378 |
| 41 | 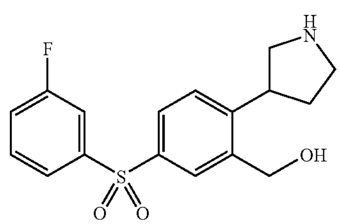 | [5-(3-Fluoro-benzenesulfonyl)-2-pyrrolidin-3-yl-phenyl]-methanol | 336 |
| 42 | 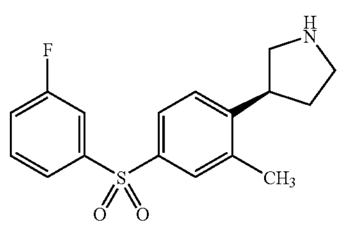 | 3-[4-(3-Fluoro-benzenesulfonyl)-2-methyl-phenyl]-(S)-pyrrolidine | 320 |
| 43 | 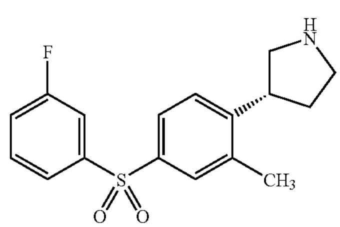 | 3-[4-(3-Fluoro-benzenesulfonyl)-2-methyl-phenyl]-(R)-pyrrolidine | 320 |
| 44 | 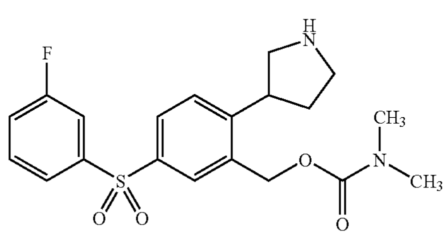 | Dimethyl-carbamic acid 5-(3-fluoro-benzenesulfonyl)-2-pyrrolidin-3-yl-benzyl ester | 407 |

TABLE 1-continued

| # | Name (Autonom ™) | MP/M + H |
|---|---|---|
| 45 | 5-(3-Fluoro-benzenesulfonyl)-2-pyrrolidin-3-yl-benzoic acid | 218.1-219.7° C. |
| 46 | 2-(5-Benzenesulfonyl-2-pyrrolidin-3-yl-phenoxy)-N,N-dimethyl-acetamide | 389 |
| 47 | 8-(3-Methyl-4-pyrrolidin-3-yl-benzenesulfonyl)-quinolin-5-ol | 223.9-225.6° C. (HCl Salt) |
| 48 | 5-(3-Methyl-4-pyrrolidin-3-yl-benzenesulfonyl)-1,3-dihydro-indol-2-one | 269.7-272.1° C. (HCl Salt) |
| 49 | 4-(3-Methyl-4-(S)-pyrrolidin-3-yl-benzenesulfonyl)-phenol | 318 |
| 50 | 3-[4-(4-Methoxy-benzenesulfonyl)-2-methyl-phenyl]-1-methyl-pyrrolidine | 346 |
| 51 | 4-[3-Methyl-4-(1-methyl-pyrrolidin-3-yl)-benzenesulfonyl]-phenol | 186.0-187.5° C. (HCl Salt) |

TABLE 1-continued

| # | Structure | Name (Autonom ™) | MP/M + H |
|---|---|---|---|
| 52 | 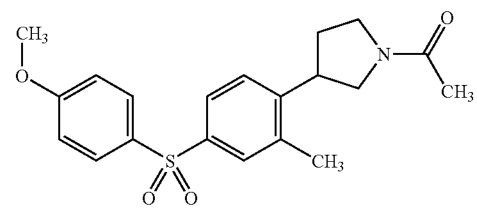 | 1-{4-[4-(4-Methoxy-benzenesulfonyl)-2-methyl-phenyl]-pyrrolidin-1-yl}-ethanone | 374 |
| 53 | 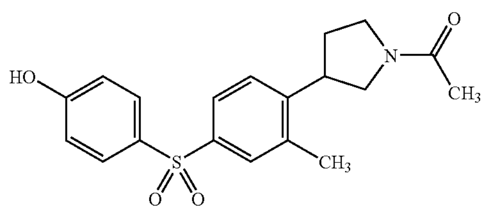 | 1-{3-[4-(4-Hydroxy-benzenesulfonyl)-2-methyl-phenyl]-pyrrolidin-1-yl}-ethanone | 360 |
| 54 | 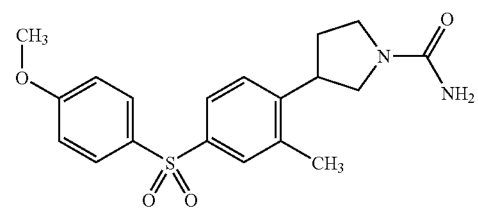 | 3-[4-(4-Methoxy-benzenesulfonyl)-2-methyl-phenyl]-pyrrolidine-1-carboxylic acid amide | 375 |
| 55 | 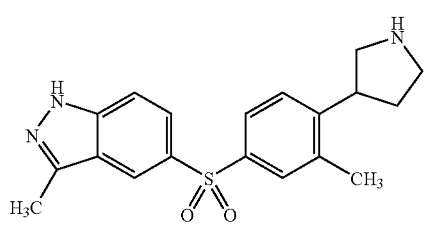 | 3-Methyl-5-(3-methyl-4-pyrrolidin-3-yl-benzenesulfonyl)-1H-indazole | 223.0-225.0° C. (HCl Salt) |
| 56 | 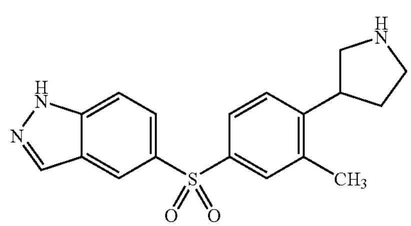 | 5-(3-Methyl-4-pyrrolidin-3-yl-benzenesulfonyl)-1H-indazole | 191.3-193.6° C. (HCl Salt) |
| 57 | 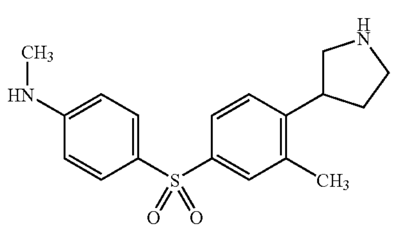 | Methyl-[4-(3-methyl-4-pyrrolidin-3-yl-benzenesulfonyl)-phenyl]-amine | 179.9-182.0° C. (HCl Salt) |
| 58 | 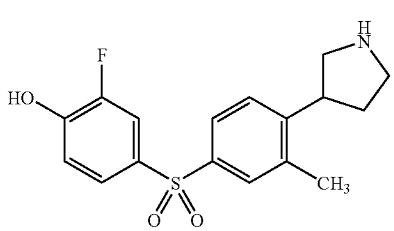 | 2-Fluoro-4-(3-methyl-4-pyrrolidin-3-yl-benzenesulfonyl)-phenol | 198.0-199.3° C. (HCl Salt) |

TABLE 1-continued

| # | Structure | Name (Autonom ™) | MP/M + H |
|---|---|---|---|
| 59 | 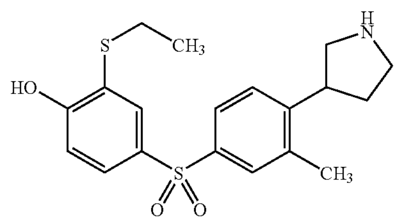 | 2-Ethylsulfanyl-4-(3-methyl-4-pyrrolidin-3-yl-benzenesulfonyl)-phenol | 190.7-192.5° C. (HCl Salt) |
| 60 | 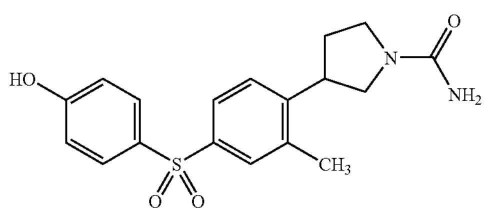 | 3-[4-(4-Hydroxy-benzenesulfonyl)-2-methyl-phenyl]-pyrrolidine-1-carboxylic acid amide | 146.1-148.7° C. |
| 61 | 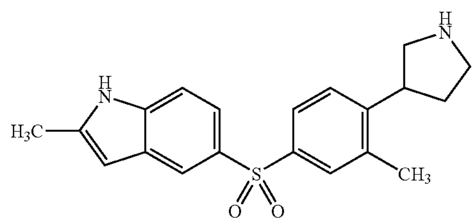 | 2-Methyl-5-(3-methyl-4-pyrrolidin-3-yl-benzenesulfonyl)-1H-indole | 355 |
| 62 | 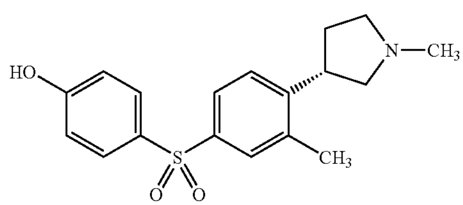 | 4-[3-Methyl-4-(1-methyl-(S)-pyrrolidin-3-yl)-benzenesulfonyl]-phenol | 332 |
| 63 | 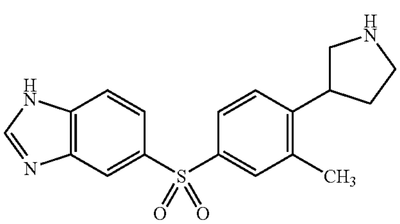 | 5-(3-Methyl-4-pyrrolidin-3-yl-benzenesulfonyl)-1H-benzoimidazole | 268.0-270.9° C. (HCl salt) |
| 64 | 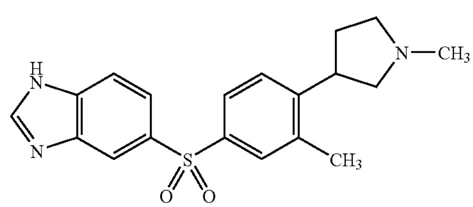 | 5-[3-Methyl-4-(1-methyl-pyrrolidin-3-yl)-benzenesulfonyl]-1H-indazole | 356 |
| 65 | 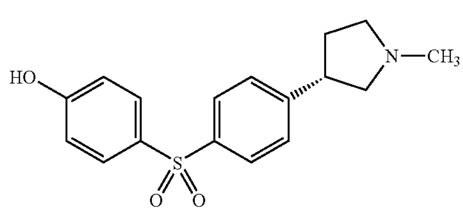 | 4-[4-(1-Methyl-(S)-pyrrolidin-3-yl)-benzenesulfonyl]-phenol | 197-199° C. (HCl salt) |

TABLE 1-continued

| # | Structure | Name (Autonom ™) | MP/M + H |
|---|---|---|---|
| 66 | 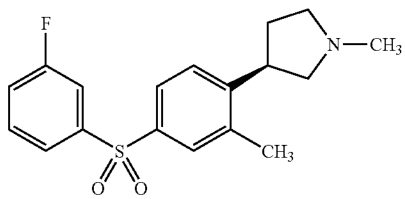 | 3-[4-(3-Fluoro-benzenesulfonyl)-2-methyl-phenyl]-1-methyl-(R)-pyrrolidine | 334 |
| 67 | 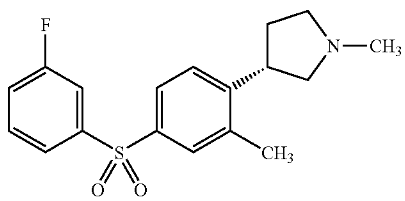 | 3-[4-(3-Fluoro-benzenesulfonyl)-2-methyl-phenyl]-1-methyl-(S)-pyrrolidine | 334 |
| 68 | 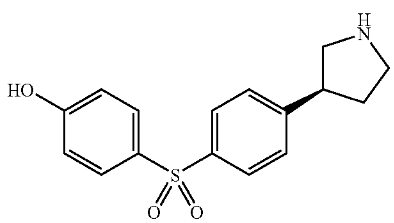 | 4-(4-(S)-Pyrrolidin-3-yl-benzenesulfonyl)-phenol | 128.9-130.9° C. (HCl salt) |
| 69 | 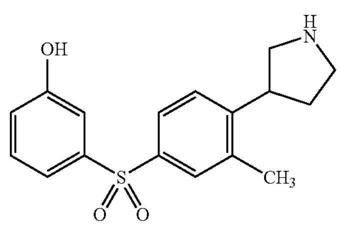 | 3-(3-Methyl-4-pyrrolidin-3-yl-benzenesulfonyl)-phenol | 167.0-169.3° C. (HCl Salt) |
| 70 | 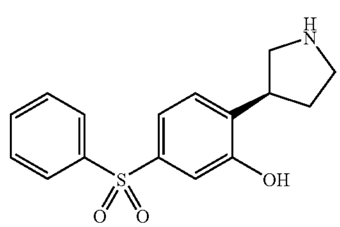 | 5-Benzenesulfonyl-2-(S)-pyrrolidin-3-yl-phenol | 205° C. (HCl Salt) |
| 71 | 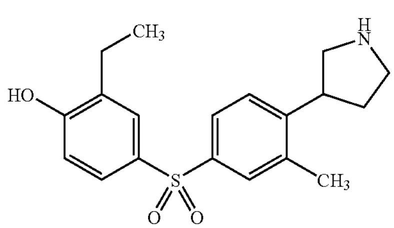 | 2-Ethyl-4-(3-methyl-4-pyrrolidin-3-yl-benzenesulfonyl)-phenol | 103.0-104.3° C. (HCl Salt) |
| 72 | 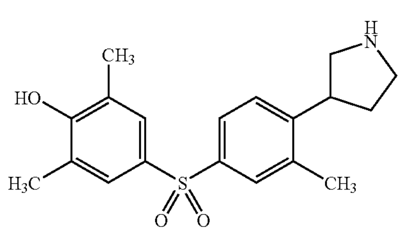 | 2,6-Dimethyl-4-(3-methyl-4-pyrrolidin-3-yl-benzenesulfonyl)-phenol | 278.5-280.9° C. (HCl Salt) |

TABLE 1-continued

| # | Structure | Name (Autonom ™) | MP/M + H |
|---|---|---|---|
| 73 | 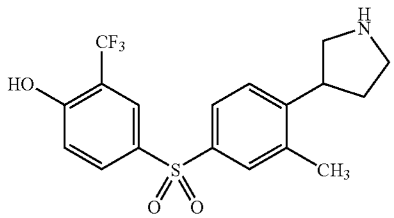 | 4-(3-Methyl-4-pyrrolidin-3-yl-benzenesulfonyl)-2-trifluoromethyl-phenol | 160.9-164.5° C. (HCl salt) |
| 74 | 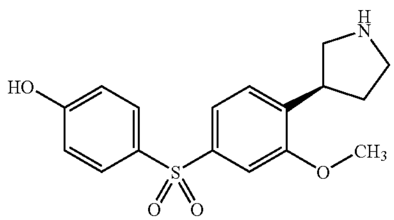 | 4-(3-Methoxy-4-(S)-pyrrolidin-3-yl-benzenesulfonyl)-phenol | 276.9-277.5° C. (HCl salt) |
| 75 | 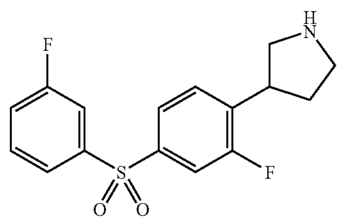 | 3-[2-Fluoro-4-(3-fluoro-benzenesulfonyl)-phenyl]-pyrrolidine | 324 |
| 76 | 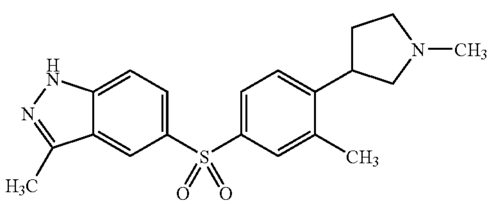 | 3-Methyl-5-[3-methyl-4-(1-methyl-pyrrolidin-3-yl)-benzenesulfonyl]-1H-indazole | 164.0-165.0° C. |
| 77 | 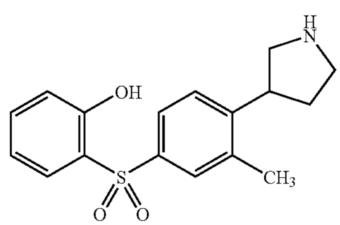 | 2-(3-Methyl-4-pyrrolidin-3-yl-benzenesulfonyl)-phenol | 130.0-132.2° C. (HCl Salt) |
| 78 | 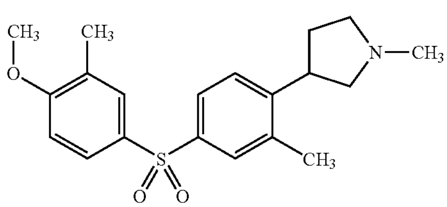 | 3-[4-(4-Methoxy-3-methyl-benzenesulfonyl)-2-methyl-phenyl]-1-methyl-pyrrolidine | 360 |
| 79 | 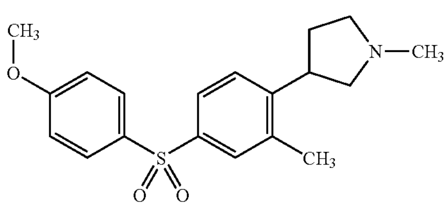 | 3-[4-(4-Methoxy-benzenesulfonyl)-2-methyl-phenyl]-1-methyl-pyrrolidine | 346 |

TABLE 1-continued

| # | Structure | Name (Autonom ™) | MP/M + H |
|---|---|---|---|
| 80 | 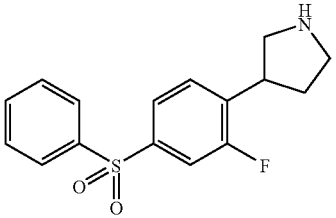 | 3-(4-Benzenesulfonyl-2-fluoro-phenyl)-pyrrolidine | 200.1-204.9° C. (HCl Salt) |
| 81 | 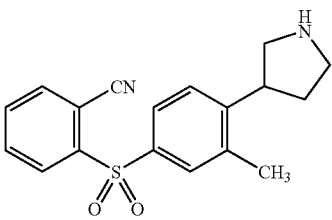 | 2-(3-Methyl-4-pyrrolidin-3-yl-benzenesulfonyl)-benzonitrile | 327 |
| 83 | 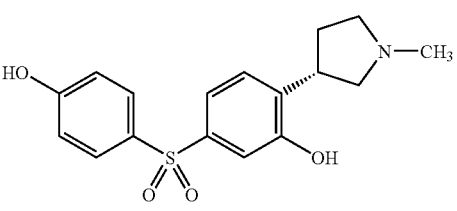 | 5-(4-Hydroxy-benzenesulfonyl)-2-(1-methyl-(S)-pyrrolidin-3-yl)-phenol | 104.0-106.6° C. |
| 83 | 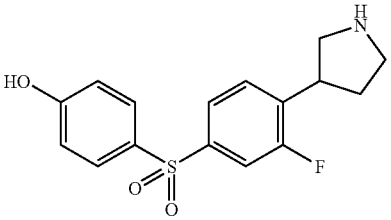 | 4-(3-Fluoro-4-pyrrolidin-3-yl-benzenesulfonyl)-phenol | 322 |
| 84 | 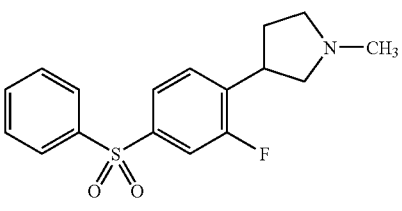 | 3-(4-Benzenesulfonyl-2-fluoro-phenyl)-1-methyl-pyrrolidine | 320 |
| 85 | 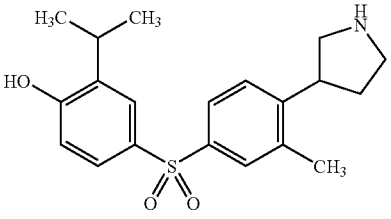 | 2-Isopropyl-4-(3-methyl-4-pyrrolidin-3-yl-benzenesulfonyl)-phenol | 125.0-128.0° C. |
|  | 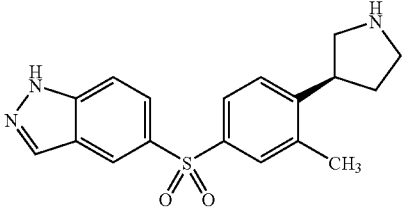 | 5-(3-Methyl-4-(S)-pyrrolidin-3-yl-benzenesulfonyl)-1H-indazole | 342 |

TABLE 1-continued

| # | Structure | Name (Autonom ™) | MP/M + H |
|---|---|---|---|
| 86 | 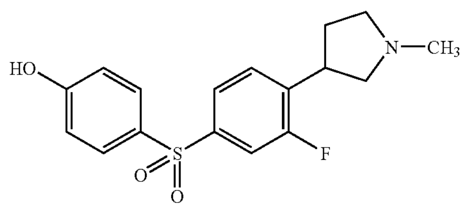 | 4-[3-Fluoro-4-(1-methyl-pyrrolidin-3-yl)-benzenesulfonyl]-phenol | 336 |
| 87 | 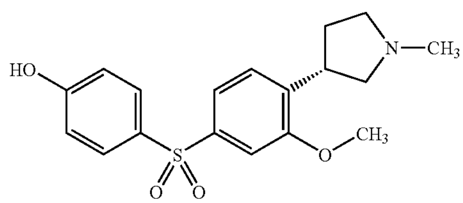 | 4-[3-Methoxy-4-(1-methyl-(S)-pyrrolidin-3-yl)-benzenesulfonyl]-phenol | 348 |
| 88 | 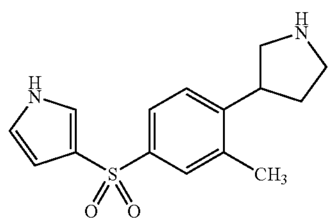 | 3-(3-Methyl-4-pyrrolidin-3-yl-benzenesulfonyl)-1H-pyrrole | 291 |
| 89 | 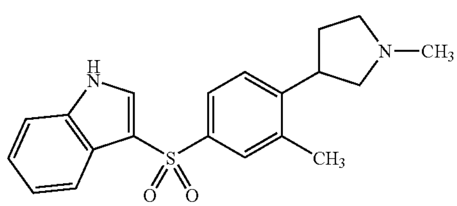 | 3-[3-Methyl-4-(1-methyl-pyrrolidin-3-yl)-benzenesulfonyl]-1H-indole | 355 |
| 90 | 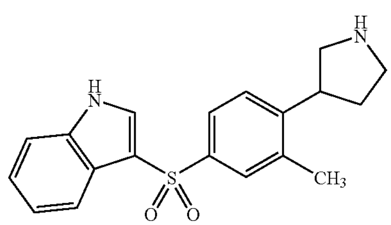 | 3-(3-Methyl-4-pyrrolidin-3-yl-benzenesulfonyl)-1H-indole | 341 |
| 91 | 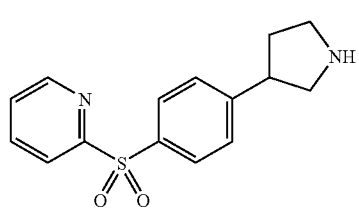 | 2-(4-Pyrrolidin-3-yl-benzenesulfonyl)-pyridine | 289 |
| 92 | 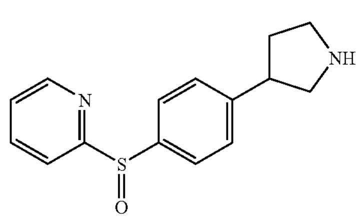 | 2-(4-Pyrrolidin-3-yl-benzenesulfinyl)-pyridine | 273 |

TABLE 1-continued

| # | Structure | Name (Autonom ™) | MP/M + H |
|---|---|---|---|
| 93 | 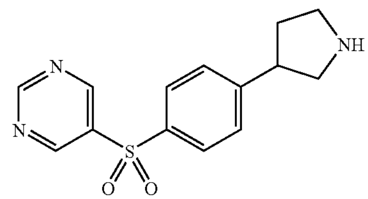 | 4-Pyrrolidin-3-yl-benzenesulfonyl)-pyrimidine | 290 |
| 94 | 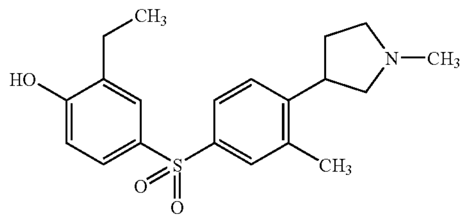 | 2-Ethyl-4-[3-methyl-4-(1-methyl-pyrrolidin-3-yl)-benzenesulfonyl]-phenol | 360 |
| 95 | 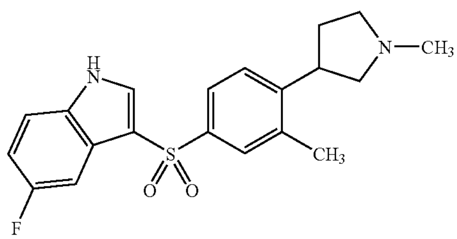 | 5-Fluoro-3-[3-methyl-4-(1-methyl-pyrrolidin-3-yl)-benzenesulfonyl]-1H-indole | 86.5-93.5° C. |
| 96 | 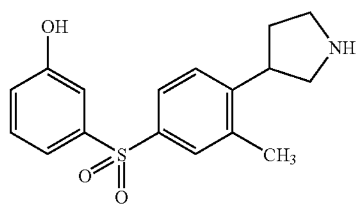 | 3-(3-Methyl-4-pyrrolidin-3-yl-benzenesulfonyl)-phenol | 332 |
| 97 | 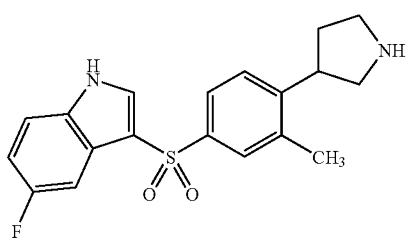 | 5-Fluoro-3-(3-methyl-4-pyrrolidin-3-yl-benzenesulfonyl)-1H-indole | 359 |
| 98 | 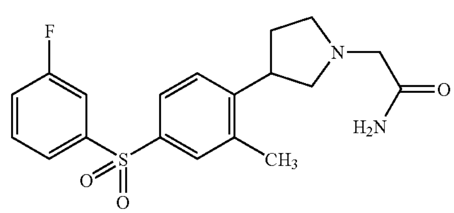 | 2-{3-[4-(3-Fluoro-benzenesulfonyl)-2-methyl-phenyl]-pyrrolidin-1-yl}-acetamide | 377 |
| 99 | 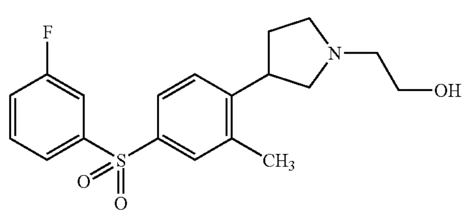 | 2-{3-[4-(3-Fluoro-benzenesulfonyl)-2-methyl-phenyl]-pyrrolidin-1-yl}-ethanol | 364 |

TABLE 1-continued

| # | Structure | Name (Autonom ™) | MP/M + H |
|---|---|---|---|
| 100 | 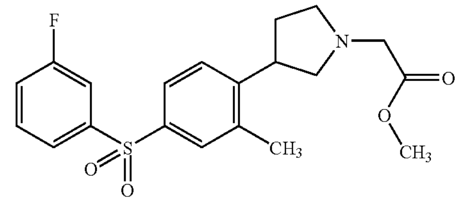 | {3-[4-(3-Fluoro-benzenesulfonyl)-2-methyl-phenyl]-pyrrolidin-1-yl}-acetic acid methyl ester | 392 |
| 101 | 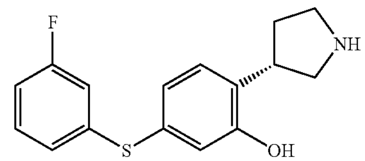 | 5-(3-Fluoro-phenylsulfanyl)-2-(S)-pyrrolidin-3-yl-phenol | 290 |
| 102 | 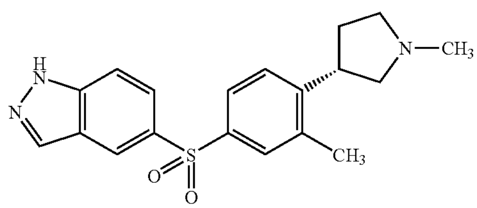 | 5-[3-Methyl-4-(1-methyl-(S)-pyrrolidin-3-yl)-benzenesulfonyl]-1H-indazole | 356 |
| 103 | 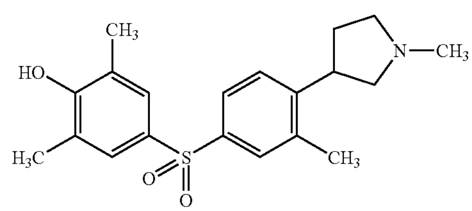 | 2,6-Dimethyl-4-[3-methyl-4-(1-methyl-pyrrolidin-3-yl)-benzenesulfonyl]-phenol | 72.5-77.0 |
| 104 | 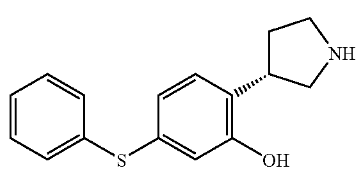 | 5-Phenylsulfanyl-2-(S)-pyrrolidin-3-yl-phenol | 272 |
| 105 | 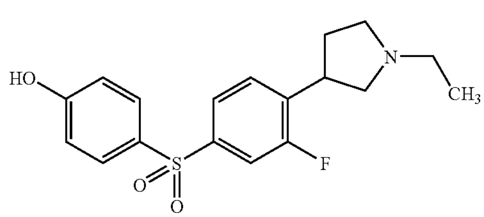 | 4-[4-(1-Ethyl-pyrrolidin-3-yl)-3-fluoro-benzenesulfonyl]-phenol | 350 |
| 106 | 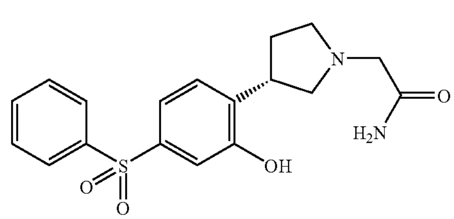 | 2-[3-(4-Benzenesulfonyl-2-hydroxy-phenyl)-(S)-pyrrolidin-1-yl]-acetamide | 361 |

TABLE 1-continued

| # | Structure | Name (Autonom ™) | MP/M + H |
|---|---|---|---|
| 107 | 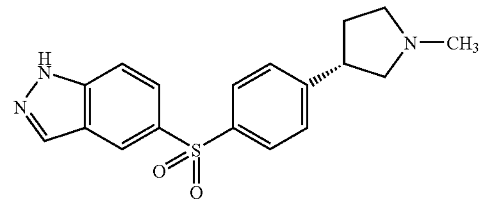 | 5-[4-(1-Methyl-(S)-pyrrolidin-3-yl)-benzenesulfonyl]-1H-indazole | 342 |
| 108 | 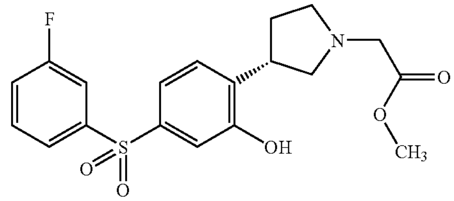 | {3-[4-(3-Fluoro-benzenesulfonyl)-2-hydroxy-phenyl]-(S)-pyrrolidin-1-yl}-acetic acid methyl ester | 394 |
| 109 | 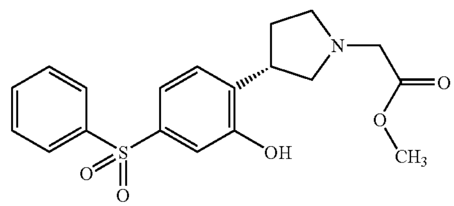 | [3-(4-Benzenesulfonyl-2-hydroxy-phenyl)-(S)-pyrrolidin-1-yl]-acetic acid methyl ester | 376 |
| 110 | 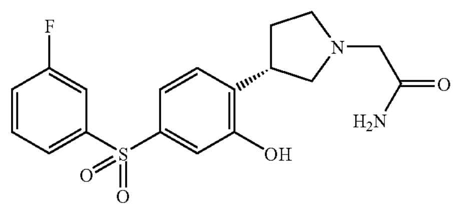 | 2-{3-[4-(3-Fluoro-benzenesulfonyl)-2-hydroxy-phenyl]-(S)-pyrrolidin-1-yl}-acetamide | 379 |
| 111 | 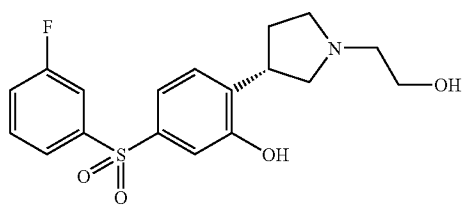 | 5-(3-Fluoro-benzenesulfonyl)-2-[1-(2-hydroxy-ethyl)-(S)-pyrrolidin-3-yl]-phenol | 366 |
| 112 | 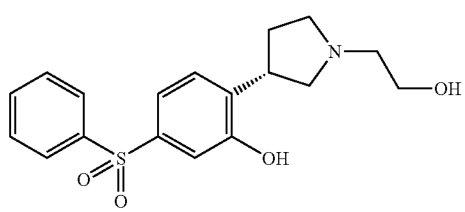 | 5-Benzenesulfonyl-2-[1-(2-hydroxy-ethyl)-(S)-pyrrolidin-3-yl]-phenol | 348 |
| 113 | 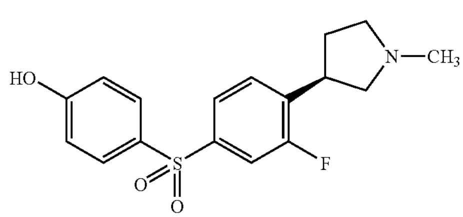 | 4-[3-Fluoro-4-(1-methyl-(R)-pyrrolidin-3-yl)-benzenesulfonyl]-phenol | 336 |

TABLE 1-continued

| # | Structure | Name (Autonom ™) | MP/M + H |
|---|---|---|---|
| 114 | 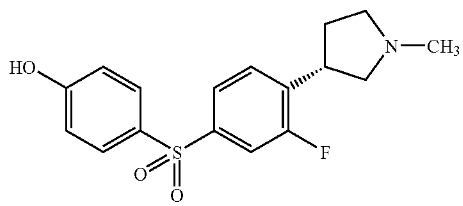 | 4-[3-Fluoro-4-(1-methyl-(S)-pyrrolidin-3-yl)-benzenesulfonyl]-phenol | 336 |
| 115 | 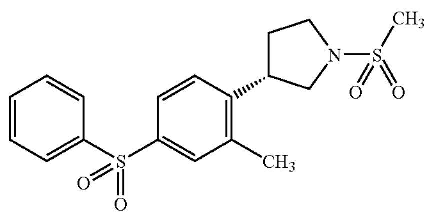 | 3-(4-Benzenesulfonyl-2-methyl-phenyl)-1-methanesulfonyl-(S)-pyrrolidine | 56.0-58.0° C. |
| 116 | 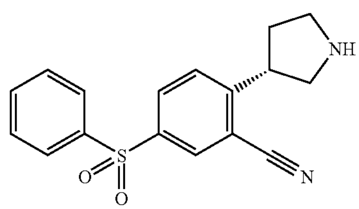 | 5-Benzenesulfonyl-2-(S)-pyrrolidin-3-yl-benzonitrile | 313 |
| 117 | 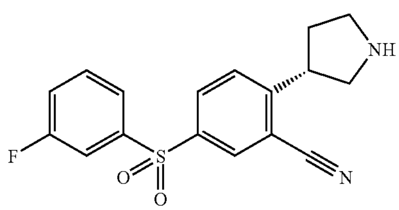 | 5-(3-Fluoro-benzenesulfonyl)-2-(S)-pyrrolidin-3-yl-benzonitrile | 331 |
| 118 | 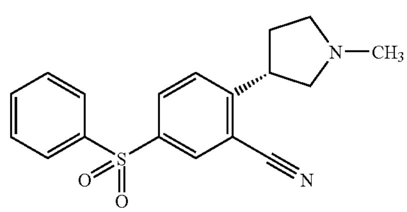 | 5-Benzenesulfonyl-2-(1-methyl-(S)-pyrrolidin-3-yl)-benzonitrile | 326 |
| 119 | 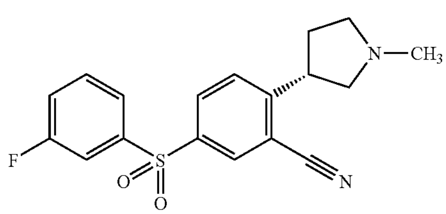 | 5-(3-Fluoro-benzenesulfonyl)-2-(1-methyl-(S)-pyrrolidin-3-yl)-benzonitrile | 345 |
| 120 | 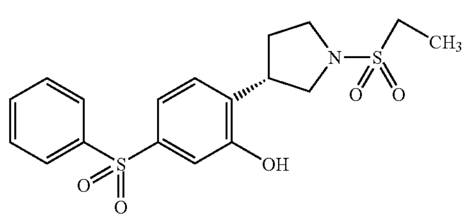 | 5-Benzenesulfonyl-2-(1-ethanesulfonyl-(S)-pyrrolidin-3-yl)-phenol | 386 |

TABLE 1-continued

| # | Structure | Name (Autonom ™) | MP/M + H |
|---|---|---|---|
| 121 | 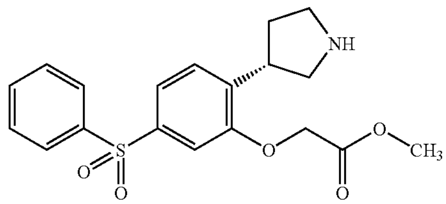 | (5-Benzenesulfonyl-2-(S)-pyrrolidin-3-yl-phenoxy)-acetic acid methyl ester | 376 |
| 122 | 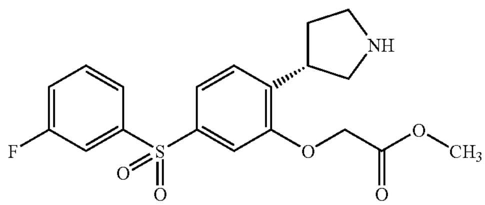 | [5-(3-Fluoro-benzenesulfonyl)-2-(S)-pyrrolidin-3-yl-phenoxy]-acetic acid methyl ester | 394 |
| 123 | 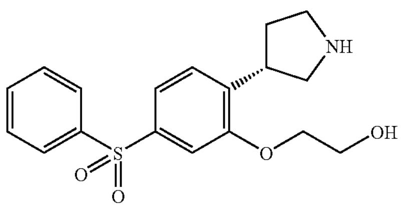 | 2-(5-Benzenesulfonyl-2-(S)-pyrrolidin-3-yl-phenoxy)-ethanol | 348 |
| 124 | 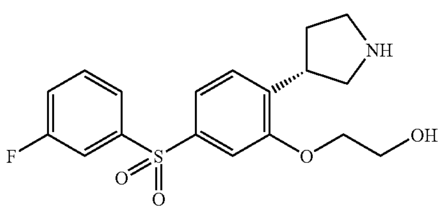 | 2-[5-(3-Fluoro-benzenesulfonyl)-2-(S)-pyrrolidin-3-yl-phenoxy]-ethanol | 366 |
| 125 | 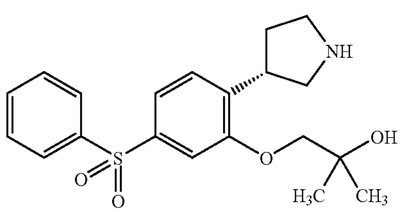 | 1-(5-Benzenesulfonyl-2-(S)-pyrrolidin-3-yl-phenoxy)-2-methyl-propan-2-ol | 376 |
| 126 | 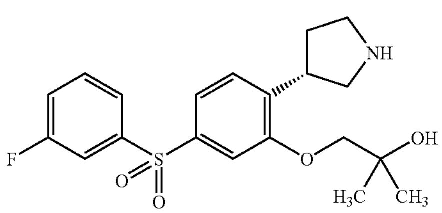 | 1-[5-(3-Fluoro-benzenesulfonyl)-2-(S)-pyrrolidin-3-yl-phenoxy]-2-methyl-propan-2-ol | 394 |
| 127 | 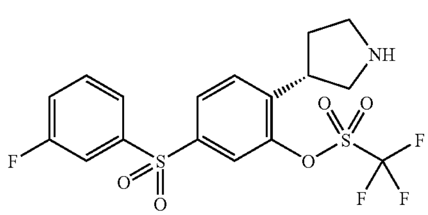 | Trifluoro-methanesulfonic acid 5-(3-fluoro-benzenesulfonyl)-2-(S)-pyrrolidin-3-yl-phenyl ester | 454 |

TABLE 1-continued

| # | Structure | Name (Autonom ™) | MP/M + H |
|---|---|---|---|
| 128 | 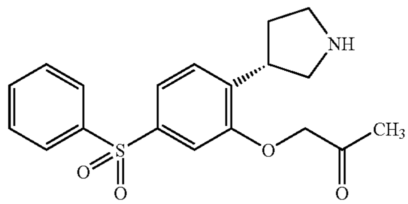 | 1-(5-Benzenesulfonyl-2-(S)-pyrrolidin-3-yl-phenoxy)-propan-2-one | 360 |
| 129 | 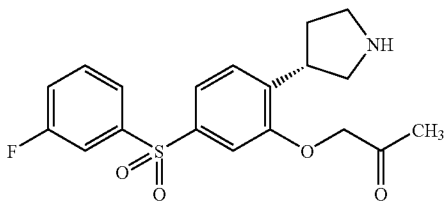 | 1-[5-(3-Fluoro-benzenesulfonyl)-2-(S)-pyrrolidin-3-yl-phenoxy]-propan-2-one | 378 |
| 130 | 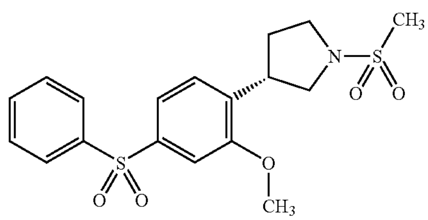 | 3-(4-Benzenesulfonyl-2-methoxy-phenyl)-1-methanesulfonyl-(S)-pyrrolidine | 396 |
| 131 | 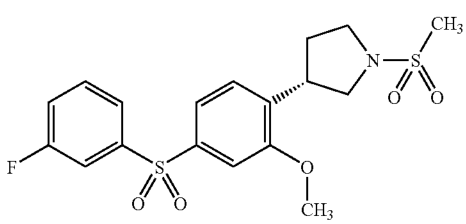 | 3-[4-(3-Fluoro-benzenesulfonyl)-2-methoxy-phenyl]-1-methanesulfonyl-(S)-pyrrolidine | 414 |
| 132 | 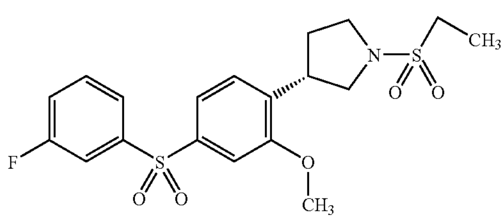 | 1-Ethanesulfonyl-3-[4-(3-fluoro-benzenesulfonyl)-2-methoxy-phenyl]-(S)-pyrrolidine | 428 |
| 133 | 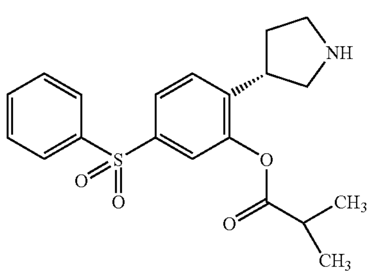 | Isobutyric acid 5-benzenesulfonyl-2-(S)-pyrrolidin-3-yl-phenyl ester | 108.4-112.5° C. (HCl salt) |

TABLE 1-continued

| # | Structure | Name (Autonom ™) | MP/M + H |
|---|---|---|---|
| 134 | 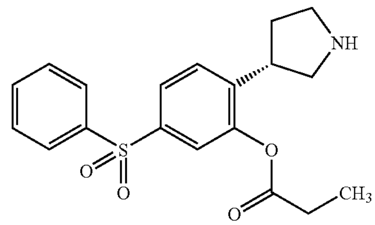 | Propionic acid 5-benzenesulfonyl-2-(S)-pyrrolidin-3-yl-phenyl ester | 176.1-179.0° C. (HCl salt) |
| 135 | 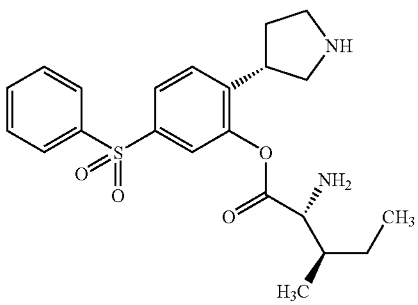 | 2-Amino-3-methyl-pentanoic acid 5-benzenesulfonyl-2-(S)-pyrrolidin-3-yl-phenyl ester | 167.3-169.6° C. (HCl salt) |
| 136 | 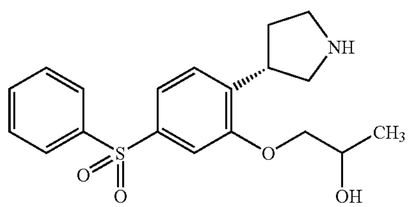 | 1-(5-Benzenesulfonyl-2-(S)-pyrrolidin-3-yl-phenoxy)-propan-2-ol | 362 |
| 137 | 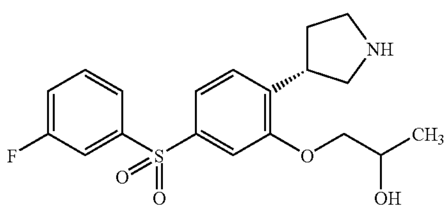 | 1-[5-(3-Fluoro-benzenesulfonyl)-2-(S)-pyrrolidin-3-yl-phenoxy]-propan-2-ol | 380 |
| 138 | 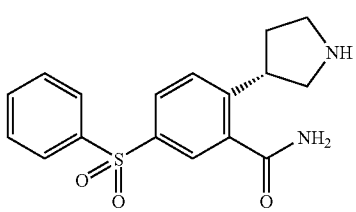 | 5-Benzenesulfonyl-2-(S)-pyrrolidin-3-yl-benzamide | 331 |
| 139 | 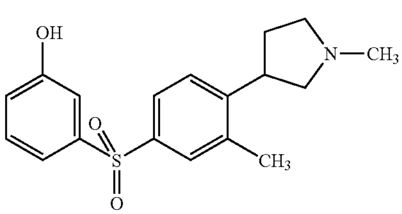 | 3-[3-Methyl-4-(1-methyl-pyrrolidin-3-yl)-benzenesulfonyl]-phenol | 332 |

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Scheme A below illustrates one synthetic procedure usable to prepare compounds of the invention, wherein R is lower alkyl, PG is an amine protecting group, and Ar, m and $R^2$ are as defined herein.

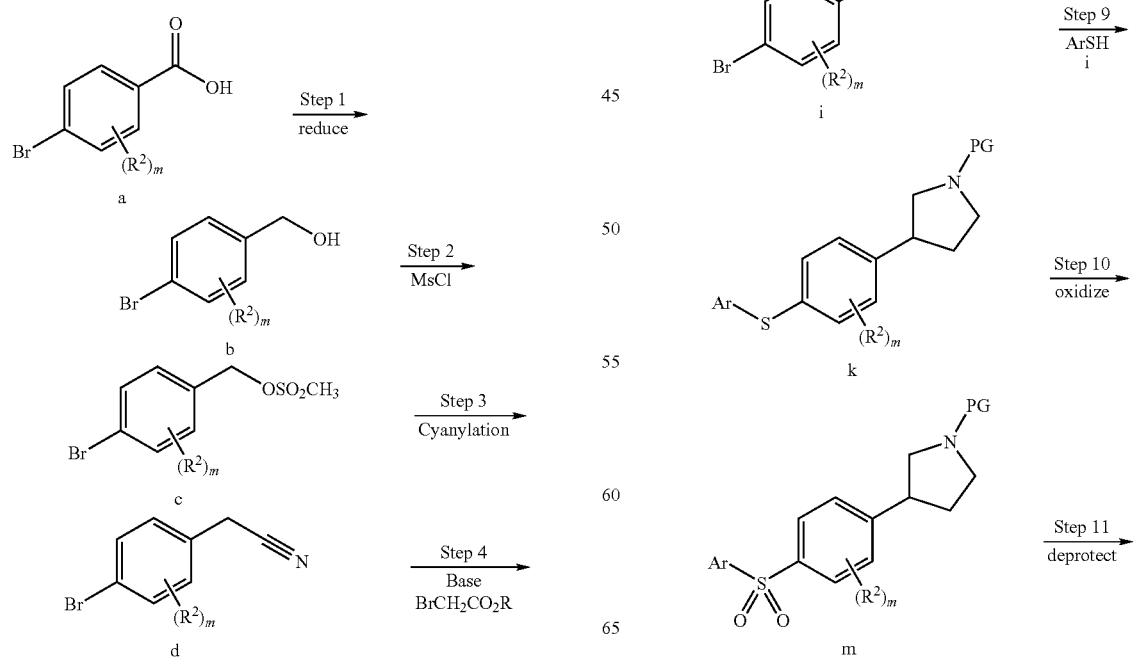

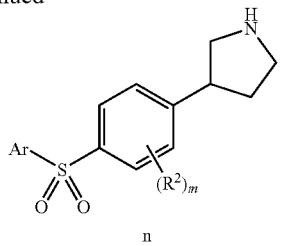

In Step 1 of Scheme A, bromobenzoic acid compound a is reduced bromobenzyl alcohol b. This reduction may be carried out using, for example, a borane reducing agent. In step 2 compound b is treated with methanesulfonyl chloride to form mesyl ester compound c. Cyanylation is carried out in step 3 by treatment of compound c with a cyanate reactant, such as a tetraalkylammonium cyanate, to afford nitrile compound d. Compound d is then alkylated in step 4 by treatment with base such as lithium aluminum hydride, followed by 2-bromoacetate ester, to give nitrile ester compound e. Compound e is reduced in step 5 to provide nitrile alcohol compound f. In step 6 the nitrile group of compound f is reduced and protected to yield amino alcohol compound g. In step 7 compound g is treated with methanesulfonyl chloride to form mesyl ester compound h. Compound h then undergoes cyclization in step 8 to afford phenyl pyrrolidine compound i. Cyclization may be achieved, for example, by treatment of compound h with potassium bis(trimethylsilyl)amide. In step 9 compound i is reacted with aryl thiol j in the presence of palladium catalyst under Buchwald conditions to afford bromopyrrolidone thioether k. In step 10 the sulfur atom of compound k may be oxidized with peracid or like oxidizing agent to afford arylsulfonyl phenyl pyrrolidine compound m. Compound m may be deprotected in step 11 to afford compound n, which is a compound of formula I in accordance with the invention.

Many variations are possible in the procedure of Scheme A and will suggest themselves to those skilled in the art. Specific details for producing compounds of the invention are described in the Examples section below.

Utility

The compounds of the invention have selective affinity for 5-HT receptors, including the $5-HT_6$ the $5-HT_{2A}$ receptor, or both, and as such are expected to be useful in the treatment of certain CNS disorders such as Parkinson's disease, Huntington's disease, anxiety, depression, manic depression, psychosis, epilepsy, obsessive compulsive disorders, mood disorders, migraine, Alzheimer's disease (enhancement of cognitive memory), sleep disorders, feeding disorders such as anorexia, bulimia, and obesity, panic attacks, akathisia, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. Such compounds are also expected to be of use in the treatment of certain GI (gastrointestinal) disorders such functional bowel disorder and irritable bowel syndrome.

Testing

The pharmacology of the compounds of this invention was determined by art recognized procedures. The in vitro techniques for determining the affinities of test compounds at the 5-HT6 receptor and the 5-HT2A receptor in radioligand binding and functional assays are described below.

Administration and Pharmaceutical Composition

The invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

Compounds of the invention may be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention may be formulated for vaginal administration. Pessaries, tampons, creams, gels, pastes, foams or sprays containing in addition to the active ingredient such carriers as are known in the art to be appropriate.

The subject compounds may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described below.

EXAMPLES

The following preparations and examples are given to enable those skilled in the art to more clearly understand and to practice the present invention. They should not be considered as limiting the scope of the invention, but merely as being illustrative and representative thereof. The following abbreviations may be used in the Examples.

List of Abbreviations

AcOH acetic acid
n-BuLi n-butyllithium
$(BOC)_2O$ di-tert-butyl dicarbonate
DCM dichloromethane/methylene chloride
DIPEA diisopropylethylamine
DMAP 4-dimethylaminopyridine
DMF N,N-dimethylformamide
Ee enantiomeric excess
EtOAc ethyl acetate
HPLC high pressure liquid chromatography
LAH lithium aluminum hydride
LDA lithium diisopropylamide
m-CPBA 3-chloroperoxybenzoic acid
MeOH methanol
MsCl methanesulfonylchloride
$PdCl_2dppf$ 1,1-bis(diphenylphosphino)ferrocene dichloropalladium(II)
$Pd_2(dba)_3$ Tris(dibenzylideneacetone)dipalladium(0)
KHMDS potassium bis(trimethylsilyl)amide
TBAF tetrabutylammonium fluoride
TEA triethylamine
THF tetrahydrofuran
TFA trifluoroacetic acid
TLC thin layer chromatography
Xantphos 4,5-Bis(diphenylphosphino)-9,9-dimethylxanthene

Preparation 1

3-(4-Bromo-2-methyl-phenyl)-pyrrolidine-1-carboxylic acid tert-butyl ester

The synthetic procedure described in this Preparation was carried out using the procedure of Scheme B.

SCHEME B

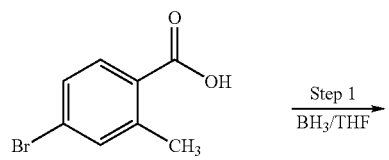

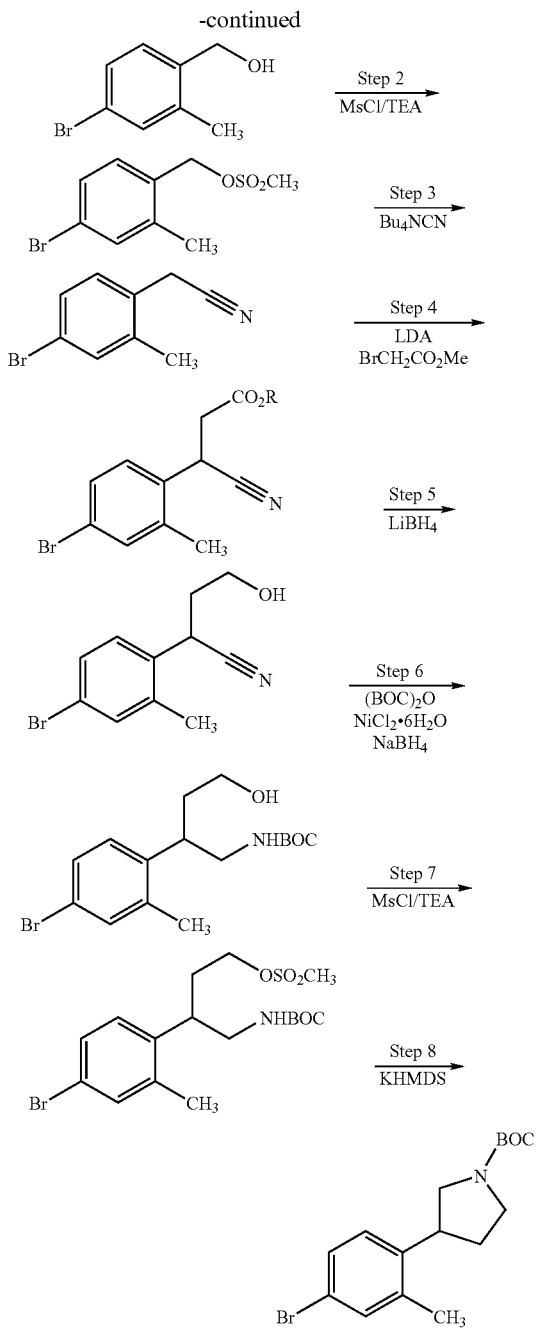

Step 1 (4-Bromo-2-methyl-phenyl)-methanol

A solution of $BH_3$ (1 M in THF, 720 mL, 0.7194 mol) was slowly added to 4-bromo-2-methyl benzoic acid (51.57 g, 0.2398 mol) at 0° C. The ice-bath was removed and the mixture was stirred overnight at room temperature. The reaction mixture was cooled to 0° C. and water was slowly added. The reaction mixture was then stirred at room temperature for 30 minutes. The resulting mixture was extracted with EtOAc, and the combined organic extracts were washed with $NaHCO_3$ (saturated solution), water and brine; dried over $MgSO_4$, filtered and evaporated under reduced pressure affording (4-bromo-2-methyl-phenyl)-methanol, which was used directly in step 2 without further purification.

Step 2 Methanesulfonic acid 4-bromo-2-methyl-benzyl ester

To a solution of (4-bromo-2-methyl-phenyl)-methanol (46.65 g, 0.2320 mol) in DCM (500 mL) at −15° C. was added mesyl chloride (20.65 mL, 0.2668 mol) followed by TEA (37.04 mL, 0.2668 mol). The reaction was stirred at −15° C. for 1.5 hour. A saturated solution of $NH_4Cl$ was then added at −15° C. and the resulting mixture was extracted with DCM. The organic phase was dried over $MgSO_4$, filtered, and concentrated under reduced pressure to afford methanesulfonic acid 4-bromo-2-methyl-benzyl ester as a white solid in quantitative yield (65 g), which was used directly in step 3 without further purification.

Step 3 (4-Bromo-2-methyl-phenyl)-acetonitrile

Tetrabutylammoniumcyanide (1.02 g, 3.799 mmol) was added to a solution of the methanesulfonic acid 4-bromo-2-methyl-benzyl ester (1.01 g, 3.618 mmol) in THF (20 mL) at 0° C. The reaction mixture was stirred at room temperature for 6 hours. The solvent was removed under reduced pressure, water was added to the residue, and the mixture was extracted with $Et_2O$. The combined organic extracts were washed with water and brine; dried over $MgSO_4$, filtered, and evaporated under reduced pressure. The residue was purified via flash chromatography (hexane/EtOAc, 9/1) to give 0.65 g (80% yield) of 4-bromo-2-methyl-phenyl)-acetonitrile as a white solid.

Step 4 3-(4-Bromo-2-methyl-phenyl)-3-cyano-propionic acid methyl ester

Lithium diisopropylamide (2 M in THF, 110 mL) was added dropwise at −78° C. to a solution of (4-bromo-2-methyl-phenyl)-acetonitrile (38.55 g, 0.1835 mol) in THF (400 mL). The reaction mixture was stirred for 10 minutes and methyl bromoacetate (16.87 mL, 0.1835 mol) was added. The resulting mixture was stirred at −78° C. for 2 hours. A saturated solution of $NH_4Cl$ was then added at −78° C. and the resulting mixture was warmed to room temperature. Water was added and the mixture was extracted with EtOAc. The combined organic extracts were washed with water and brine; dried over $MgSO_4$, filtered, and evaporated under reduced pressure. The residue was purified via flash chromatography (hexane/EtOAc, 9/1) to give 43.09 g of 3-(4-bromo-2-methyl-phenyl)-3-cyano-propionic acid methyl ester (83% yield) as a yellow oil.

Step 5 2-(4-Bromo-2-methyl-phenyl)-4-hydroxy-butyronitrile

Lithium borohydride (4.99 g, 0.2290 mol) was added to a room temperature solution of 3-(4-bromo-2-methyl-phenyl)-3-cyano-propionic acid methyl ester (43.08 g, 0.1527 mol) in THF (500 mL) and the reaction mixture was stirred overnight. The reaction mixture was cooled to 0° C., and a solution of 10% $KHSO_4/Na_2SO_4$ was slowly added until pH 1-2 was reached. The resulting mixture was extracted with EtOAc, and the combined organic extracts were washed with water and brine, dried over $Na_2SO_4$, filtered, and evaporated under reduced pressure. The residue was purified via flash chromatography (hexane/EtOAc, 7/3) to give 27.3 g (87% yield) of 2-(4-bromo-2-methyl-phenyl)-4-hydroxy-butyronitrile as a white solid.

Step 6 [2-(4-Bromo-2-methyl-phenyl)-4-hydroxy-butyl]-carbamic acid tert-butyl ester To a solution of 2-(4-bromo-2-methyl-phenyl)-4-hydroxy-butyronitrile (27.3 g, 0.1074 mol) in MeOH (750 mL) at 0° C. was added $(BOC)_2O$ (46.9 g, 0.2149 mol), followed by $NiCl_2.6H_2O$ (2.55 g, 0.01074 mol) and sodium borohydride (27.83 g, 0.7359 mol). The mixture was stirred at room temperature for 24 hours, and diethylenetriamine (12 mL, 0.1074 mol) was added. The reaction mixture was stirred for 30 minutes, then solvent was evaporated under reduced pressure. The resulting crude material was partitioned between $NaHCO_3$ (10% aqueous solution) and EtOAc. The organic phase was washed with water and brine; dried over $Na_2SO_4$, filtered, and evaporated under reduced pressure. The residue was purified via flash chromatography (hexane/EtOAc, 6/4) to give 30.3 g (79% yield) of [2-(4-bromo-2-methyl-phenyl)-4-hydroxy-butyl]-carbamic acid tert-butyl ester.

Step 8 Methanesulfonic acid 3-(4-bromo-2-methyl-phenyl)-4-tert-butoxycarbonylamino-butyl ester Mesyl chloride (7.53 mL, 0.09726 mol) was added, at −78° C., to a solution of [2-(4-bromo-2-methyl-phenyl)-4-hydroxy-butyl]-carbamic acid tert-butyl ester (30.3 g, 0.08457 mol) in DCM (600 mL) followed by TEA (27 mL, 0.1945 mol). The reaction mixture was stirred at −78° C. for 1 hour, then allowed to reach room temperature with stirring for an additional hour. A saturated aqueous solution of $NH_4Cl$ was added, and the resulting mixture was extracted with DCM. The combined organic extracts were dried over $MgSO_4$, filtered, and evaporated under reduced pressure to give methanesulfonic acid 3-(4-bromo-2-methyl-phenyl)-4-tert-butoxycarbonylamino-butyl ester, which was used without further purification.

Step 8 3-(4-Bromo-2-methyl-phenyl)-pyrrolidine-1-carboxylic acid tert-butyl ester KHMDS (0.5 M in toluene, 186 mL, 0.09303 mol) was added at 0° C. to methanesulfonic acid 3-(4-bromo-2-methyl-phenyl)-4-tert-butoxycarbonylamino-butyl ester (36.9 g, 0.08457 mol) dissolved in THF (400 mL). The ice-bath was removed and the mixture was stirred at room temperature for 2 hours. A saturated solution of $NH_4Cl$ was added to the reaction mixture and the resulting mixture was extracted with EtOAc. The combined organic extracts were washed with water and brine, dried over $MgSO_4$, filtered, and evaporated under reduced pressure. The residue was purified via flash chromatography (hexane/EtOAc, 8/2) to give 27.3 g (95% yield) of 3-(4-bromo-2-methyl-phenyl)-pyrrolidine-1-carboxylic acid tert-butyl ester as a clear oil.

3-(4-Bromo-2-methoxy-phenyl)-pyrrolidine-1-carboxylic acid tert-butyl ester was similarly prepared, replacing 4-bromo-2-methyl benzoic acid in step 1 with 4-bromo-2-methoxy benzoic acid.

Preparation 2

3-(4-Mercapto-2-methoxy-phenyl)-pyrrolidine-1-carboxylic acid tert-butyl ester The synthetic procedure described in this Preparation was carried out according to the process shown in Scheme C.

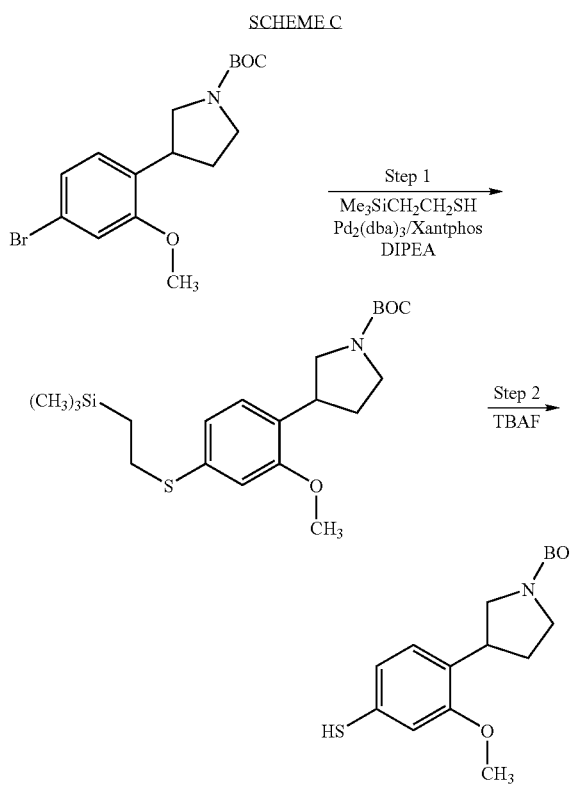

Step 1 3-[2-Methoxy-4-(2-trimethylsilanyl-ethylsulfanyl)-phenyl]-pyrrolidine-1-carboxylic acid tert-butyl ester Tris(dibenzylideneacetone)dipalladium(0) (32 mg, 0.03509 mmol), 4,5-Bis(diphenylphosphino)-9,9-dimethylxanthene (40 mg, 0.07017 mmol), 2-(triethylsilyl)ethanethiol (57 μL, 1.403 mmol) and DIPEA (0.257 mL, 2.807 mmol) were added to a solution of 3-(4-bromo-2-methoxy-phenyl)-pyrrolidine-1-carboxylic acid tert-butyl ester (0.50 g, 1.403 mmol) in 1,4-dioxane (10 mL). The reaction mixture was heated at reflux for 18 hours. The reaction mixture was cooled and a solution of 10% KHSO$_4$/Na$_2$SO$_4$ was added. The resulting mixture was extracted with EtOAc, and the combined organic extracts were washed with water and brine; dried over Na$_2$SO$_4$, filtered and evaporated under reduced pressure. The residue was purified via flash chromatography (hexane/EtOAc, 95/5) to give 0.380 g (66% yield) of 3-[2-methoxy-4-(2-trimethylsilanyl-ethylsulfanyl)-phenyl]-pyrrolidine-1-carboxylic acid tert-butyl ester as a clear oil.

Step 2 3-(4-Mercapto-2-methoxy-phenyl)-pyrrolidine-1-carboxylic acid tert-butyl ester A solution of tetrabutylammoniumfluoride (1.0 M in THF, 9.3 mL) was added to a solution of 3-[2-methoxy-4-(2-trimethylsilanyl-ethylsulfanyl)-phenyl]-pyrrolidine-1-carboxylic acid tert-butyl ester (0.380 g, 0.9275 mmol) in THF (5 mL) and the reaction mixture was stirred at room temperature for 30 minutes. A solution of 10% KHSO$_4$/Na$_2$SO$_4$ was added and the resulting mixture was extracted 3 times with EtOAc. The combined organic extracts were washed with water and brine; and then dried over Na$_2$SO$_4$. The solvent was evaporated under reduced pressure and the crude material was purified via flash chromatography (hexane/EtOAc/AcOH, 80/20/0.1) to give 0.178 g (62% yield) of 3-(4-mercapto-2-methoxy-phenyl)-pyrrolidine-1-carboxylic acid tert-butyl ester as a clear oil.

3-(4-Mercapto-2-methyl-phenyl)-pyrrolidine-1-carboxylic acid tert-butyl ester was similarly prepared, using 3-(4-bromo-2-methoxy-phenyl)-pyrrolidine-1-carboxylic acid tert-butyl ester in step 1.

Preparation 3

1-Benzenesulfonyl-3-bromo-5-fluoro-1H-indole

The synthetic procedure described in this Preparation was carried out according to the process shown in Scheme D.

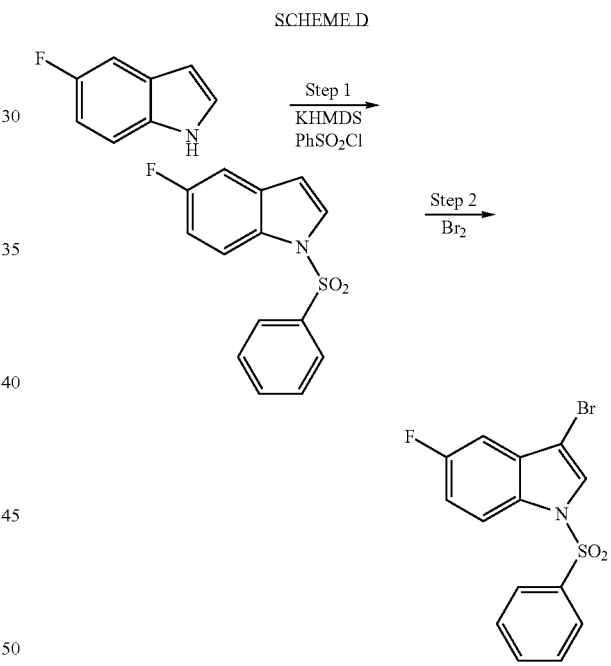

Step 1 1-Benzenesulfonyl-5-fluoro-1H-indole

KHMDS (0.5 M in toluene, 23 mL, 11.65 mmol) was added at 0° C. to a solution of 5-fluoroindole (1.5 g, 11.09 mmol) in DMF (23 mL). After stirring for 10 minutes, benzenesulfonyl chloride (1.55 mL, 12.209 mmol) was added. The ice-bath was removed and the mixture was stirred at room temperature for 4 hours. A saturated solution of NH$_4$Cl was added to the reaction, and the resulting mixture was extracted with EtOAc. The combined organic extracts were washed with water and brine; dried over Na$_2$SO$_4$, filtered and evaporated under reduced pressure. The residue was recrystallized from toluene to afford 2.26 g (74% yield) of 1-benzenesulfonyl-5-fluoro-1H-indole as a white solid.

Step 2
1-Benzenesulfonyl-3-bromo-5-fluoro-1H-indole

Bromine (0.187 mL, 3.632 mmol) was added dropwise to a room temperature solution of 1-benzenesulfonyl-5-fluoro-1H-indole (1.0 g, 3.632 mmol) in DMF (5 mL). The reaction mixture was stirred at room temperature for 5 hours. A saturated solution of NH$_4$Cl was added, and the resulting mixture was extracted with EtOAc. The combined organic extracts were washed with water and with brine; dried over Na$_2$SO$_4$, filtered, and evaporated under reduced pressure. The residue was purified via flash chromatography (hexane/EtOAc, 95/5) to give 0.676 g (53% yield) of 1-benzenesulfonyl-3-bromo-5-fluoro-1H-indole as a white solid.

Preparation 4

3-Bromo-pyrrole-1-carboxylic acid tert-butyl ester

The synthetic procedure described in this Preparation was carried out according to the process shown in Scheme E.

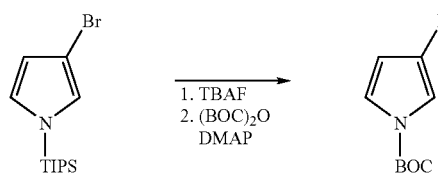

A solution of TBAF (1.0 M in THF, 3.6 mL) was added to a solution of 3-bromo-1-triisopropylsilanyl-1H-pyrrole (1.0 g, 3.308 mmol) in THF (10 mL) and the mixture was stirred at room temperature for 30 minutes. (BOC)$_2$O (0.866 g, 3.965 mmol) and DMAP (40 mg, 0.3308 mmol) were added to the reaction and the resulting mixture was stirred for 2 additional hours. Water was added, and the mixture was extracted with EtOAc. The combined organic extracts were washed with water and with brine; dried over Na$_2$SO$_4$, filtered, and evaporated under reduced pressure. The residue was purified via flash chromatography (hexane/EtOAc) to give 0.197 g (24% yield) of 3-bromo-pyrrole-1-carboxylic acid tert-butyl ester as a clear oil.

Preparation 5

4-Bromo-2-chloro-1-(4-methoxy-benzyloxy)-benzene

The synthetic procedure described in this Preparation was carried out according to the process shown in Scheme F.

SCHEME F

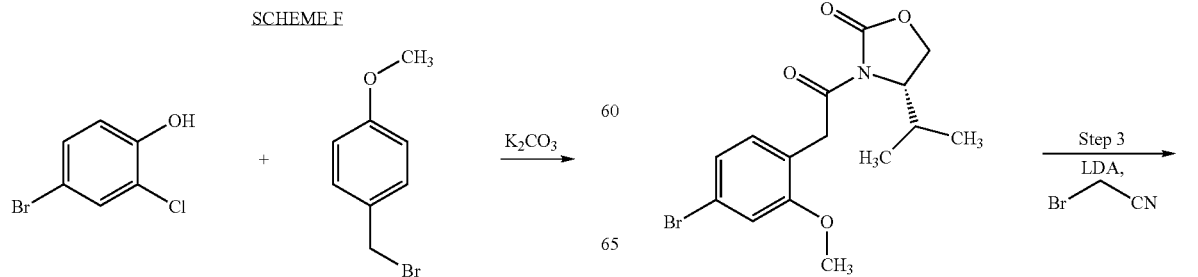

-continued

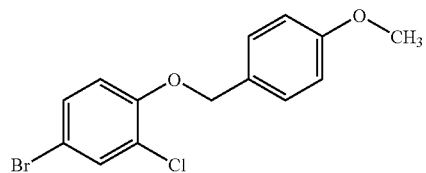

Potassium carbonate (0.98 g, 7.086 mmol) was added to a solution of 4-bromo-2-chlorophenol (0.7 g, 3.374 mmol) and 4-methoxybenzylbromide (0.51 mL, 3.543 mmol) in acetone (20 mL) and the mixture was stirred at room temperature overnight. The solid phase was removed by filtration and the filtrate was evaporated to dryness under reduced pressure. The residue was partitioned between EtOAc and aqueous NaOH (2 M). The organic layer was washed with water and brine; dried over Na$_2$SO$_4$, filtered, and evaporated under reduced pressure. The residue was purified via flash chromatography (hexane/EtOAc, 99/1) to give 0.937 g (85% yield) of 4-bromo-2-chloro-1-(4-methoxy-benzyloxy)-benzene as yellow solid.

Preparation 6

(S)-3-(4-Bromo-2-hydroxy-phenyl)-pyrrolidine-1-carboxylic acid tert-butyl ester The synthetic procedure described in this Preparation was carried out according to the process shown in Scheme G.

SCHEME G

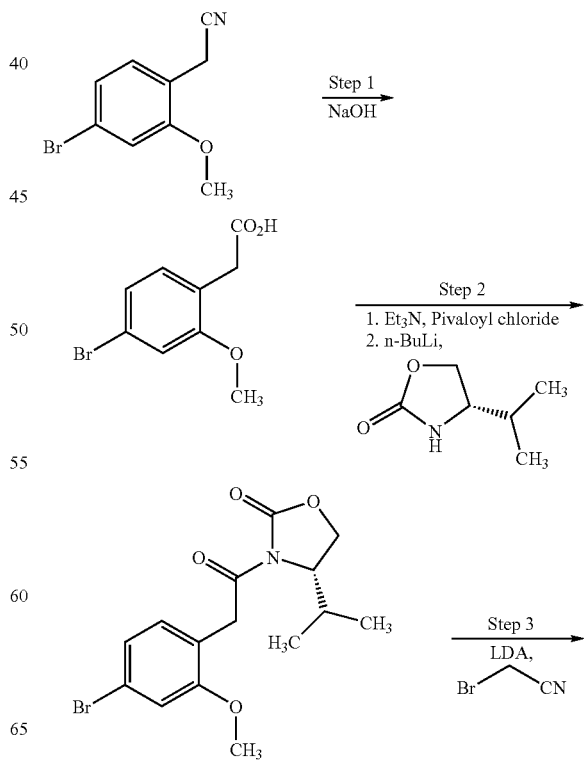

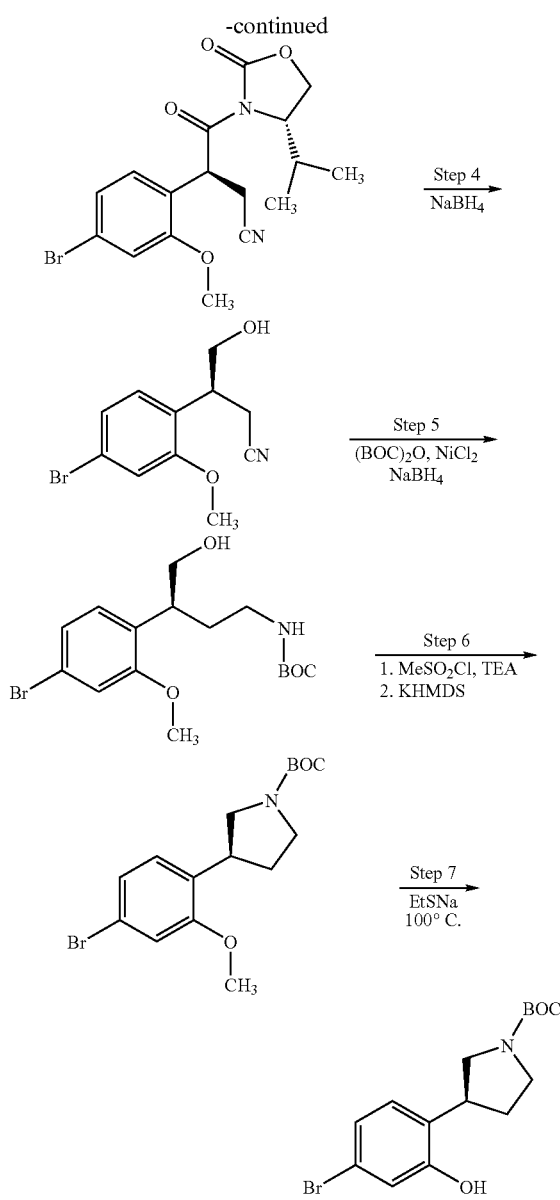

Step 1 (4-Bromo-2-methoxy-phenyl)-acetic acid

A solution of NaOH (5.72 g, 143 mmol) in water (29 mL) was added to a solution of (4-bromo-2-methoxy-phenyl)-acetonitrile (10.2 g, 45.1 mmol) in MeOH (100 mL). The reaction mixture was heated at reflux for 18 hours. The solvent was evaporated under reduced pressure and water was added. The aqueous mixture was washed with diethyl ether, and the aqueous layer was acidified by addition of aqueous HCl (2 M) to pH 1. The aqueous mixture was then extracted with EtOAc, and the combined organic extracts were washed with brine, dried over $Na_2SO_4$, filtered, and evaporated under reduced pressure to give 9.49 g (86% yield) of (4-bromo-2-methoxy-phenyl)-acetic acid.

Step 2 (S)-3-[2-(4-Bromo-2-methoxy-phenyl)-acetyl]-4-isopropyl-oxazolidin-2-one Triethylamine (0.66 mL, 4.75 mmol) was added to a solution of (4-bromo-2-methoxy-phenyl)-acetic acid (1.02 g, 4.162 mmol) in THF (11 mL) in a first round bottom flask under argon atmosphere. The mixture was cooled at −78° C. and pivaloyl chloride (0.513 mL, 4.162 mmol) was added. After stirring for 10 minutes at −78° C., the reaction mixture was warmed to 0° C. and stirred for 30 minutes, then cooled again at −78° C. In second round bottom flask (S)-4-isopropyl-2-oxazolidinone (591.2 mg, 4.577 mmol) was dissolved in THF (20 mL) and cooled to −78° C., and n-BuLi (2.5 M in hexane, 2.0 mL, 4.99 mmol) was added. After stirring for 10 minutes at −78° C., the metallated oxazolidinone mixture in the second flask was added to the mixed anhydride in the first flask at −78° C. The reaction mixture was stirred for 4 hours at 0° C., then at room temperature for 18 hours. A saturated solution of $NH_4Cl$ was added, and the mixture was extracted with EtOAc. The combined organic extracts were washed with brine, dried over $Na_2SO_4$, filtered and evaporated under reduced pressure. The residue was purified via flash chromatography (hexane/EtOAc, 84/16) to give 1.13 g (77% yield) of (S)-3-[2-(4-bromo-2-methoxy-phenyl)-acetyl]-4-isopropyl-oxazolidin-2-one.

Step 3 (S)-3-(4-Bromo-2-methoxy-phenyl)-4-((S)-4-isopropyl-2-oxo-oxazolidin-3-yl)-4-oxo-butyronitrile Lithium diisopropylamide (2.0 M in heptane/THF/ethylbenzene, 1.58 mL, 3.16 mmol) was added to a solution of (S)-3-[2-(4-bromo-2-methoxy-phenyl)-acetyl]-4-isopropyl-oxazolidin-2-one (1.126 g, 3.16 mmol) in THF (11 mL) under argon atmosphere at −78° C. The mixture was stirred for 15 minutes and bromoacetonitrile (0.23 mL, 3.32 mmol) was added at −78° C. The mixture was stirred for 3 hours at 0° C., and then a saturated solution of $NH_4Cl$ was added. The mixture was extracted with EtOAc, and the combined organic extracts were washed with brine, dried over $Na_2SO_4$, filtered and evaporated under reduced pressure. The residue was purified via flash chromatography (hexane/EtOAc, 85/15) to give 755 mg (60% yield) of (S)-3-(4-bromo-2-methoxy-phenyl)-4-((S)-4-isopropyl-2-oxo-oxazolidin-3-yl)-4-oxo-butyronitrile as a white solid.

Step 4 (S)-3-(4-Bromo-2-methoxy-phenyl)-4-hydroxy-butyronitrile

A solution of sodium borohydride (389 mg) in water (1.82 mL) was added to a solution of (S)-3-(4-bromo-2-methoxy-phenyl)-4-((S)-4-isopropyl-2-oxo-oxazolidin-3-yl)-4-oxo-butyronitrile (749 mg, 1.895 mmol) in THF (6 mL) under nitrogen atmosphere. The mixture was stirred at room temperature for three hours. The reaction mixture was cooled to 0° C. and a solution of 10% $KHSO_4/Na_2SO_4$ was carefully added. After the gas evolution stopped, the mixture was extracted with EtOAc. The combined organic extracts were washed with brine, dried over $Na_2SO_4$, filtered, and evaporated under reduced pressure. The residue was purified via flash chromatography (hexane/EtOAc, 7/3) to give 470 mg (92% yield) of (S)-3-(4-bromo-2-methoxy-phenyl)-4-hydroxy-butyronitrile.

Step 5 [(S)-3-(4-Bromo-2-methoxy-phenyl)-4-hydroxy-butyl]-carbamic acid tert-butyl ester To a solution of (S)-3-(4-bromo-2-methoxy-phenyl)-4-hydroxy-butyronitrile (459 mg, 1.699 mmol) in MeOH (12.1 mL) at 0° C. was added $(BOC)_2O$ (736.3 mg, 3.398 mmol), $NiCl_2.6H_2O$ (40.75 mg, 0.17 mmol), and (in portions) sodium borohydride (450.3 mg, 11.9 mmol). The mixture was stirred at room temperature for 18 hours. Diethylamine (0.183 mL, 1.699 mmol) was then added and the mixture was stirred for 30 minutes. Solvent was evaporated under reduced pressure and a solution of aqueous NaHCO$_3$ (10%) was added. The mixture was extracted with EtOAc, and the combined organic extracts were washed with brine, dried over Na$_2$SO$_4$, filtered, and evaporated under reduced pressure. The residue was purified via flash chromatography (hexane/EtOAc, 7/3) to give 405 mg (64% yield) of [(S)-3-(4-bromo-2-methoxy-phenyl)-4-hydroxy-butyl]-carbamic acid tert-butyl ester.

Step 6 (S)-3-(4-Bromo-2-methoxy-phenyl)-pyrrolidine-1-carboxylic acid tert-butyl ester Mesyl chloride (93.7 µL, 1.21 mmol) was added to a solution of [(S)-3-(4-bromo-2-methoxy-phenyl)-4-hydroxy-butyl]-carbamic acid tert-butyl ester (394 mg, 1.0527 mmol) in DCM (7.5 mL) under argon atmosphere at −78° C., followed by addition of TEA (0.336 mL, 2.42 mmol). The mixture was stirred at −78° C. for 1 hour and then at room temperature for an additional hour. A solution of aqueous NaHCO$_3$ (10%) was added, and the organic layer was separated and dried over Na$_2$SO$_4$. Solvent was evaporated under reduced pressure and to afford 480 mg of crude methanesulfonic acid (S)-2-(4-bromo-2-methoxy-phenyl)-4-tert-butoxycarbonylamino-butyl ester. This material was dissolved in THF (4 mL) under Ar atmosphere and cooled to 0° C. KHMDS (0.5 M in toluene, 2.32 mL, 1.158 mmol) was added, and the reaction mixture was stirred for 1 hour at room temperature. A saturated solution of NH$_4$Cl was added, followed by brine, and the resulting mixture was extracted with EtOAc. The combined organic extracts were washed with brine, dried over Na$_2$SO$_4$, filtered, and evaporated under reduced pressure. The residue was purified via flash chromatography (hexane/EtOAc, 98/2) to give 315 mg (84% yield) of (S)-3-(4-bromo-2-methoxy-phenyl)-pyrrolidine-1-carboxylic acid tert-butyl ester in 99% ee determined by chiralcel HPLC column and hexane/i-PrOH (9/1) as mobile phase.

Step 7 (S)-3-(4-Bromo-2-hydroxy-phenyl)-pyrrolidine-1-carboxylic acid tert-butyl ester Sodium ethanethiolate (80%, 218.7 mg, 1.704 mmol) was added to a solution of (S)-3-(4-bromo-2-methoxy-phenyl)-pyrrolidine-1-carboxylic acid tert-butyl ester (303 mg, 0.8505 mmol) in DMF (3.1 mL) under argon atmosphere. The reaction mixture was heated at 105° C. for 3.5 hours, then cooled to 5° C. A solution of 10% KHSO$_4$/Na$_2$SO$_4$ was added until pH reached 2-3. Water was added, and the resulting mixture was extracted with EtOAc. The combined organic extracts were washed with water and brine, dried over Na$_2$SO$_4$, filtered, and evaporated under reduced pressure. The residue was purified via flash chromatography (hexane/EtOAc, with a gradient from 90/10 to 85/15) to give 236 mg (81% yield) of (S)-3-(4-bromo-2-hydroxy-phenyl)-pyrrolidine-1-carboxylic acid tert-butyl ester as a foam.

(S)-3-(4-Bromo-phenyl)-pyrrolidine-1-carboxylic acid tert-butyl ester was similarly prepared using the appropriate bromobenzoic acid.

(R)-3-(4-Bromo-2-hydroxy-phenyl)-pyrrolidine-1-carboxylic acid tert-butyl ester and (R)-3-(4-Bromo-2-methoxy-phenyl)-pyrrolidine-1-carboxylic acid tert-butyl ester were similarly prepared using the appropriate enantiomeric oxazolidinone in step 2.

Preparation 7

(S)-3-(4-Mercapto-phenyl)-pyrrolidine-1-carboxylic acid tert-butyl ester

The synthetic procedure described in this Preparation was carried out according to the process shown in Scheme H.

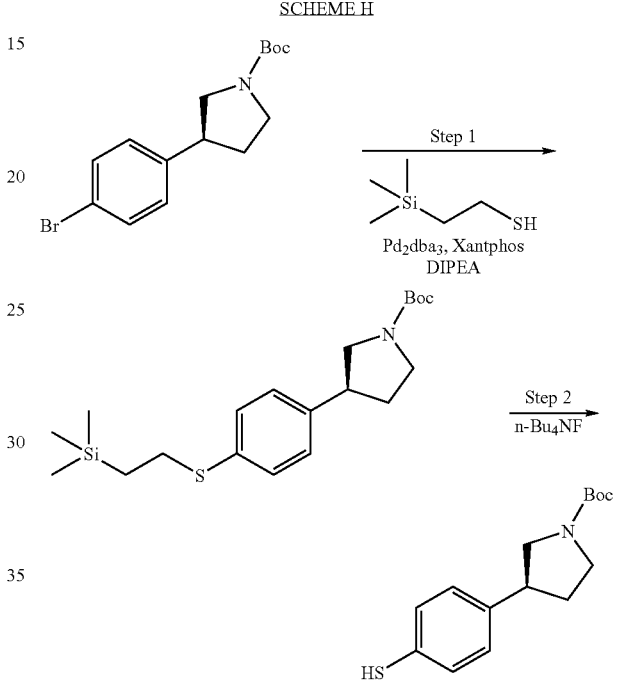

Step 1 (S)-3-[4-(2-Trimethylsilanyl-ethylsulfanyl)-phenyl]-pyrrolidine-1-carboxylic acid tert-butyl ester 2-(Trimethylsilyl)ethane thiol (0.33 mL, 2.1 mmol), Pd$_2$(dba)$_3$ (183.9 mg), Xantphos (231.4 mg) and DIPEA (0.296 mL) were added to a solution of (S)-3-(4-bromo-phenyl)-pyrrolidine-1-carboxylic acid tert-butyl ester (528 mg, 1.618 mmol) in 1,4-dioxane (7 mL) under nitrogen atmosphere. The reaction mixture was heated at 95-100° C. for 20 hours. After cooling to room temperature, a solution of 10% KHSO$_4$/Na$_2$SO$_4$ was added and the mixture was extracted with EtOAc. The combined organic extracts were washed with brine, dried over Na$_2$SO$_4$, filtered, and evaporated under reduced pressure. The residue was purified via flash chromatography (hexane/EtOAc, 94/6) to give 616 mg (quantitative yield) of (S)-3-[4-(2-trimethylsilanyl-ethylsulfanyl)-phenyl]-pyrrolidine-1-carboxylic acid tert-butyl ester.

Step 2

(S)-3-(4-Mercapto-phenyl)-pyrrolidine-1-carboxylic acid tert-butyl ester

A mixture of (S)-3-[4-(2-trimethylsilanyl-ethylsulfanyl)-phenyl]-pyrrolidine-1-carboxylic acid tert-butyl ester (613 mg, 1.615 mmol) and tetrabutylammoniumfluoride (1.0 M in THF, 10.5 mL) was stirred overnight. A solution of 10% KHSO₄/Na₂SO₄ was then added and the resulting mixture was extracted with EtOAc. The combined organic extracts were washed with brine, dried over Na₂SO₄, filtered, and evaporated under reduced pressure. The residue was purified via flash chromatography (hexane/EtOAc, 91/9) to give 288 mg (64% yield) of (S)-3-(4-mercapto-phenyl)-pyrrolidine-1-carboxylic acid tert-butyl ester as a colorless oil.

Preparation 8

3-Chloro-benzenesulfonyl fluoride

The synthetic procedure described in this Preparation was carried out according to the process shown in Scheme I.

SCHEME I

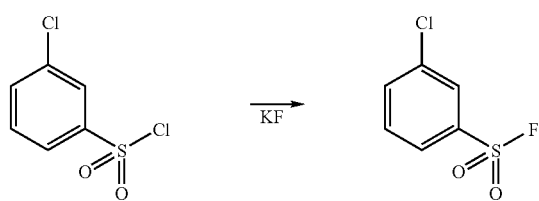

Potassium fluoride (2.28 g, 39.4 mmol) was added to a solution of 3-chlorosulfonylchloride (2.08 g, 9.855 mmol) in 1,4-dioxane (50 mL) under nitrogen atmosphere. The reaction mixture was heated at reflux for 4 hours, then cooled to 0-5° C., and ice-water was added. The resulting mixture was extracted with EtOAc. The combined organic extracts were washed with brine, dried over Na₂SO₄, filtered and evaporated under reduced pressure. The residue was purified via flash chromatography (hexane/EtOAc, 9/1) to give 1.64 g (86% yield) of 3-chlorosulfonylfluoride as a colorless oil.

Example 1

3-[4-(3-Ethylsulfanyl-benzenesulfonyl)-2-methoxy-phenyl]-pyrrolidine and 5-(3-Ethylsulfanyl-benzenesulfonyl)-2-pyrrolidin-3-yl-phenol The synthetic procedure described in this Preparation was carried out according to the process shown in Scheme J.

SCHEME J

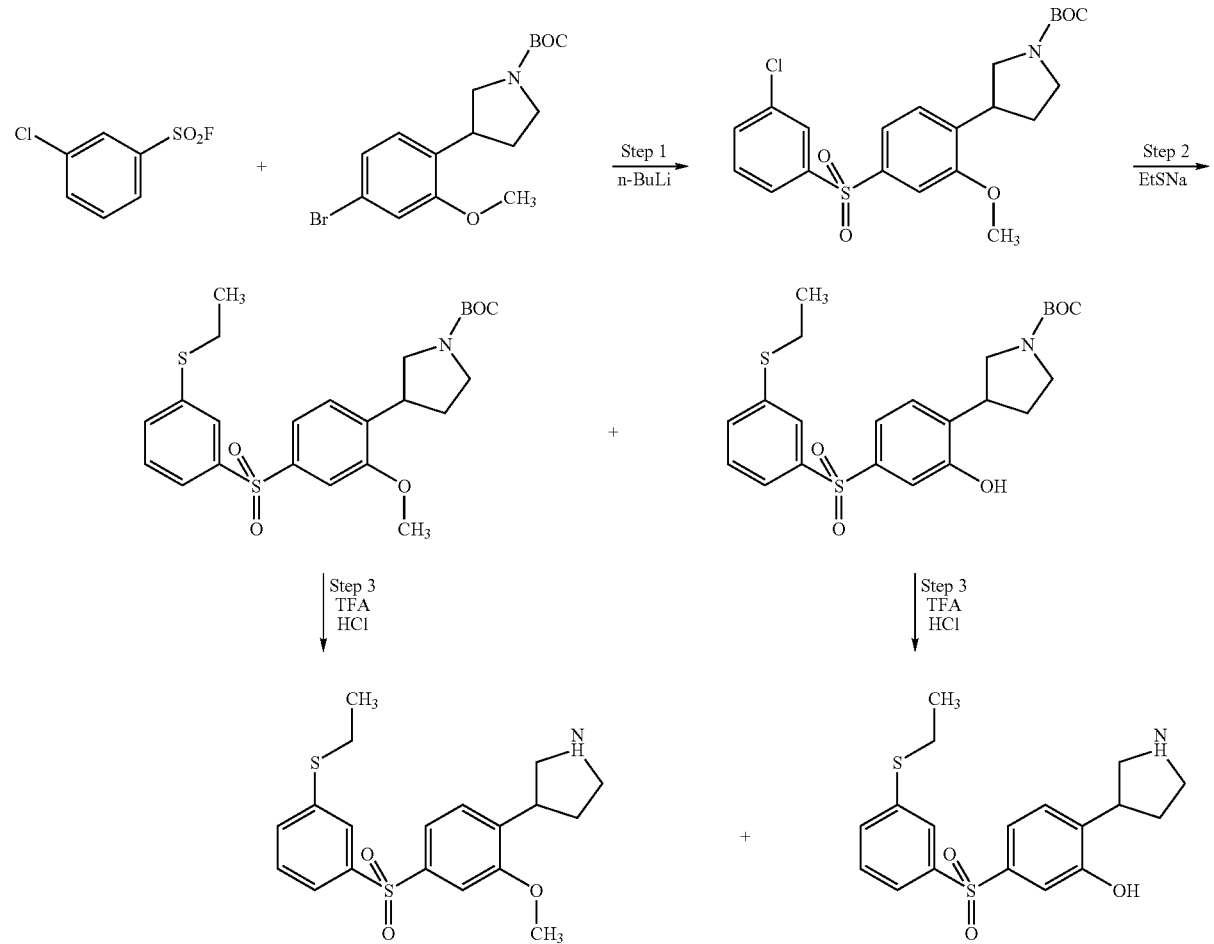

Step 1 3-[4-(3-Chloro-benzenesulfonyl)-2-methoxy-phenyl]-pyrrolidine-1-carboxylic acid tert-butyl ester n-BuLi (2.5 M in hexane, 2.76 mL, 6.905 mmol) was added to a solution of 3-(4-bromo-2-methoxy-phenyl)-pyrrolidine-1-carboxylic acid tert-butyl ester (2.05 mg, 5.754 mmol) in THF (2.5 mL) at −78° C. under Argon atmosphere. After stirring for 10 minutes at −78° C. 3-chlorosulfonylfluoride (1.13 g, 5.754 mmol) was added to the reaction and the resulting mixture was stirred for 1 hour at −78° C. A saturated solution of NH$_4$Cl was added then at −78° C. and the resulting mixture was allowed to reach room temperature. The mixture was extracted 3 times with EtOAc. The combined organic extracts were washed with water and brine; and then dried over Na$_2$SO$_4$. The solvent was evaporated under reduced pressure and the crude material was purified via flash chromatography (hexane/EtOAc, 7/3) to give 1.5 g (58% yield) of 3-[4-(3-chloro-benzenesulfonyl)-2-methoxy-phenyl]-pyrrolidine-1-carboxylic acid tert-butyl ester as a white foam.

Step 2 3-[4-(3-Ethylsulfanyl-benzenesulfonyl)-2-methoxy-phenyl]-pyrrolidine-1-carboxylic acid tert-butyl ester and 3-[4-(3-Ethylsulfanyl-benzenesulfonyl)-2-hydroxy-phenyl]-pyrrolidine-1-carboxylic acid tert-butyl ester Sodium ethanethiolate (0.698 g, 8.304 mmol) was added to a solution of 3-[4-(3-chloro-benzenesulfonyl)-2-methoxy-phenyl]-pyrrolidine-1-carboxylic acid tert-butyl ester (1.251 g, 2.768 mmol) in DMF (10 mL) and the mixture was heated at 100° C. for 48 hours. The reaction mixture was cooled to room temperature and water was added. The resulting mixture was extracted with EtOAc, and the combined organic extracts were washed with water brine, dried over Na$_2$SO$_4$, filtered and evaporated under reduced pressure. The residue was purified via flash chromatography (hexane/EtOAc/AcOH, 70/30/1) to give 3-[4-(3-ethylsulfanyl-benzenesulfonyl)-2-methoxy-phenyl]-pyrrolidine-1-carboxylic acid tert-butyl ester as a first fraction, and 3-[4-(3-ethylsulfanyl-benzenesulfonyl)-2-hydroxy-phenyl]-pyrrolidine-1-carboxylic acid tert-butyl ester as a second fraction.

Step 3 3-[4-(3-Ethylsulfanyl-benzenesulfonyl)-2-methoxy-phenyl]-pyrrolidine

Trifluoroacetic acid (1 mL) was added to a solution of 3-[4-(3-ethylsulfanyl-benzenesulfonyl)-2-methoxy-phenyl]-pyrrolidine-1-carboxylic acid tert-butyl ester (60 mg, 0.1256 mmol) in DCM (3 mL), and the mixture was stirred at room temperature for 2 hours. The solvent was evaporated under reduced pressure and the residue was partitioned between NaOH (2 M) and DCM. The organic layer was separated and washed with water, dried over Na$_2$SO$_4$, and evaporated under reduced pressure, affording 3-[4-(3-ethylsulfanyl-benzenesulfonyl)-2-methoxy-phenyl]-pyrrolidine, which was transformed in the corresponding hydrochloride (white foam, 53 mg) by addition of a small excess of HCl in 1,4-dioxane. MS (M+H)=378.

3-[4-(3-Ethylsulfanyl-benzenesulfonyl)-2-hydroxy-phenyl]-pyrrolidine-1-carboxylic acid tert-butyl ester was similarly converted to 5-(3-ethylsulfanyl-benzenesulfonyl)-2-pyrrolidin-3-yl-phenol hydrochloride: Mp=65.1-70.0° C.; MS (M+H)=364.

Similarly prepared using the procedure of Example 1, was 2-Ethylsulfanyl-4-(3-methyl-4-pyrrolidin-3-yl-benzenesulfonyl)-phenol: Mp=190.7-192.5° C.; MS (M+H)=378.

Example 2

5-(3-Ethanesulfonyl-benzenesulfonyl)-2-pyrrolidin-3-yl-phenol

The synthetic procedure described in this Example was carried out according to the process shown in Scheme K.

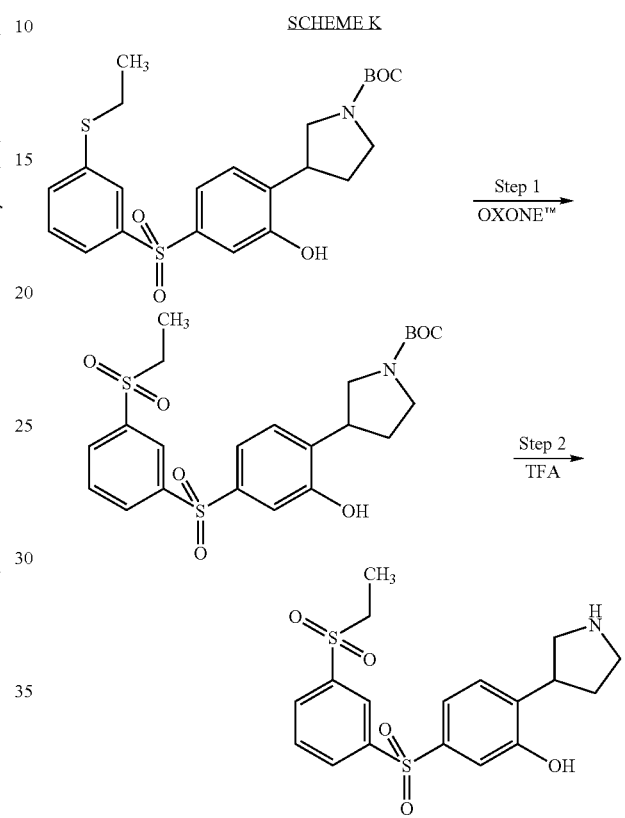

SCHEME K

Step 1 3-[4-(3-Ethanesulfonyl-benzenesulfonyl)-2-hydroxy-phenyl]-pyrrolidine-1-carboxylic acid tert-butyl ester A solution of OXONE™ (0.663 g, 1.078 mmol) in water (5 mL) was added to a solution of 3-[4-(3-ethylsulfanyl-benzenesulfonyl)-2-hydroxy-phenyl]-pyrrolidine-1-carboxylic acid tert-butyl ester (0.50 g, 1.078 mmol) in a mixture of MeOH (5 mL) and acetonitrile (5 mL). The reaction mixture was stirred at room temperature for 3 hours, then water was then added and the mixture was extracted with EtOAc. The combined organic extracts were washed with brine, dried over Na$_2$SO$_4$, filtered and evaporated under reduced pressure. The crude material was purified via flash chromatography (hexane/EtOAc, 7/3) to give 0.369 g (69% yield) of 3-[4-(3-ethanesulfonyl-benzenesulfonyl)-2-hydroxy-phenyl]-pyrrolidine-1-carboxylic acid tert-butyl ester as a white solid.

Step 2 5-(3-Ethanesulfonyl-benzenesulfonyl)-2-pyrrolidin-3-yl-phenol

Using the procedure of step 3 of Example 1,5-(3-ethanesulfonyl-benzenesulfonyl)-2-pyrrolidin-3-yl-phenol was prepared as a hydrochloride salt: Mp=124.5-126.7° C.; MS (M+H)=396.

Similarly prepared was 3-[4-(3-Ethanesulfonyl-benzene-sulfonyl)-2-methoxy-phenyl]-pyrrolidine hydrochloride: Mp=98.5-100.0° C.; MS (M+H)=410.

Example 3

3-[4-(4-Methoxy-benzenesulfonyl)-2-methyl-phenyl]-1-methyl-pyrrolidine

The synthetic procedure described in this Example was carried out according to the process shown in Scheme L.

SCHEME L

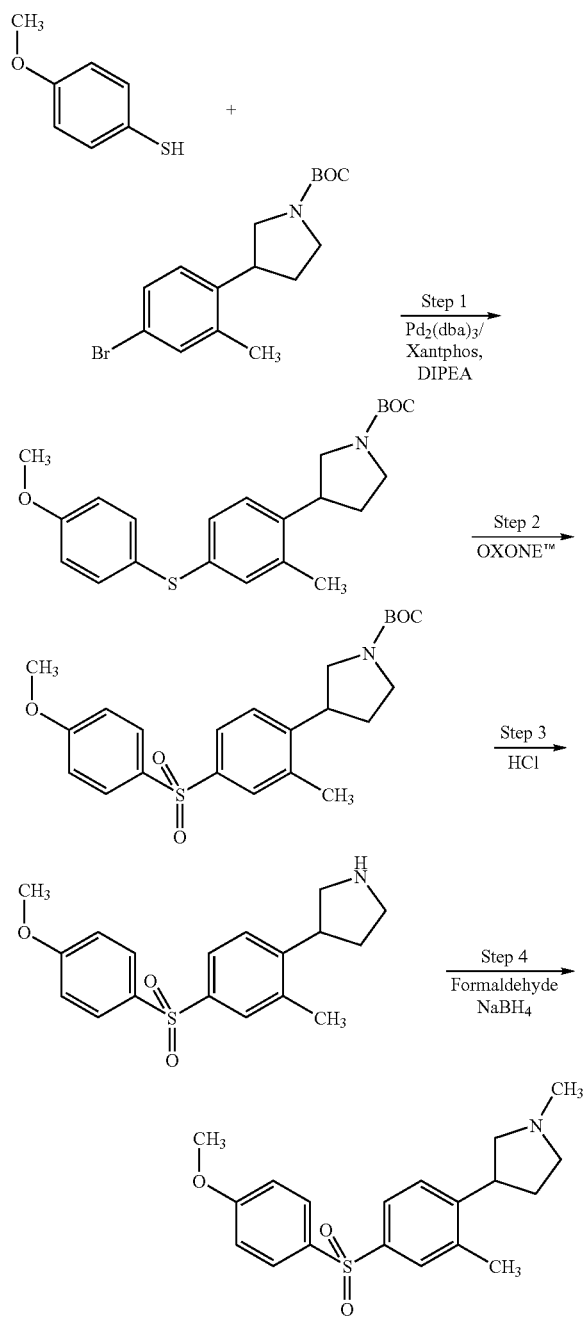

Step 1 3-[4-(4-Methoxy-phenylsulfanyl)-2-methyl-phenyl]-pyrrolidine-1-carboxylic acid tert-butyl ester Tris(dibenzylideneacetone)dipalladium(0) (336 mg, 0.3674 mmol), 4,5-Bis(diphenylphosphino)-9,9-dimethylxanthene (425 mg, 0.7347 mmol), 4-methoxy-benzenethiol (361 µL, 2.939 mmol) and DIPEA (0.538 mL, 5.878 mmol) were added to a solution of 3-(4-bromo-2-methyl-phenyl)-pyrrolidine-1-carboxylic acid tert-butyl ester (1.0 g, 2.939 mmol) in 1,4-dioxane (10 mL). The reaction mixture was heated at reflux for 18 hours, then cooled to room temperature, and a solution of 10% $KHSO_4/Na_2SO_4$ was added. The mixture was extracted with EtOAc, and the combined organic extracts were washed with water and brine, dried over $Na_2SO_4$, filtered and evaporated under reduced pressure. The resulting crude material was purified via flash chromatography (hexane/EtOAc, 95/5) to give 0.91 g (77% yield) of 3-[4-(4-methoxy-phenylsulfanyl)-2-methyl-phenyl]-pyrrolidine-1-carboxylic acid tert-butyl ester as a white foam.

Step 2 3-[4-(4-Methoxy-benzenesulfonyl)-2-methyl-phenyl]-pyrrolidine-1-carboxylic acid tert-butyl ester A solution of OXONE™ (2.8 g, 4.554 mmol) in water (3 mL) was added to a solution of 3-[4-(4-methoxy-phenylsulfanyl)-2-methyl-phenyl]-pyrrolidine-1-carboxylic acid tert-butyl ester (0.91 g, 2.277 mmol) in a mixture of MeOH (5 mL) and acetonitrile (5 mL). The reaction mixture was stirred at room temperature for 1 hour, then quenched by addition of water. The resulting mixture was extracted with EtOAc, and the combined organic extracts were washed with water and brine, dried over $Na_2SO_4$, filtered and evaporated under reduced pressure. The resulting crude material was purified via flash chromatography (hexane/EtOAc) to give 0.845 g (86% yield) of 3-[4-(4-methoxy-benzenesulfonyl)-2-methyl-phenyl]-pyrrolidine-1-carboxylic acid tert-butyl ester as a white foam.

Step 3 3-[4-(4-Methoxy-benzenesulfonyl)-2-methyl-phenyl]-pyrrolidine

A solution of HCl (4.0 M in 1,4-dioxane, 3.4 mL) was added to a solution of 3-[4-(4-methoxy-benzenesulfonyl)-2-methyl-phenyl]-pyrrolidine-1-carboxylic acid tert-butyl ester (0.845 g, 1.958 mmol) in 1,4-dioxane (2 mL) and the reaction mixture was stirred for 3 hours at room temperature. A solution of NaOH (2.0 M) was added and the mixture was extracted with DCM. The combined organic extracts were washed with water and brine, dried over $Na_2SO_4$, filtered, and evaporated under reduced pressure. The resulting crude material was purified via flash chromatography (DCM/MeOH/$NH_4OH$) to give 0.650 g of 3-[4-(4-methoxy-benzenesulfonyl)-2-methyl-phenyl]-pyrrolidine as a white foam: MS (M+H)=332.

Step 4 3-[4-(4-Methoxy-benzenesulfonyl)-2-methyl-phenyl]-1-methyl-pyrrolidine

A solution of formaldehyde (37% in water, 1.47 mL, 19.53 mmol) was added to a solution of 3-[4-(4-methoxy-benzenesulfonyl)-2-methyl-phenyl]-pyrrolidine (0.20 g, 0.6301 mmol) in MeOH (2 mL) and the reaction mixture was heated at reflux for 30 minutes. The mixture was cooled to 0° C. and NaBH$_4$ (0.833 g, 22.05 mmol) was slowly added. The mixture was allowed to reach room temperature and it was stirred for an additional hour. The solvent was evaporated under reduced pressure and the residue was partitioned between water and DCM. The organic layer was separated and washed with water and brine, dried over Na$_2$SO$_4$, filtered and evaporated under reduced pressure. The resulting crude material was purified via flash chromatography (DCM/MeOH/NH$_4$OH) to give 0.167 g (77% yield) of 3-[4-(4-methoxy-benzenesulfonyl)-2-methyl-phenyl]-1-methyl-pyrrolidine as a white foam: MS (M+H)=346.

Example 4

4-[3-Methyl-4-(1-methyl-pyrrolidin-3-yl)-benzenesulfonyl]-phenol hydrochloride

The synthetic procedure described in this Example was carried out according to the process shown in Scheme M.

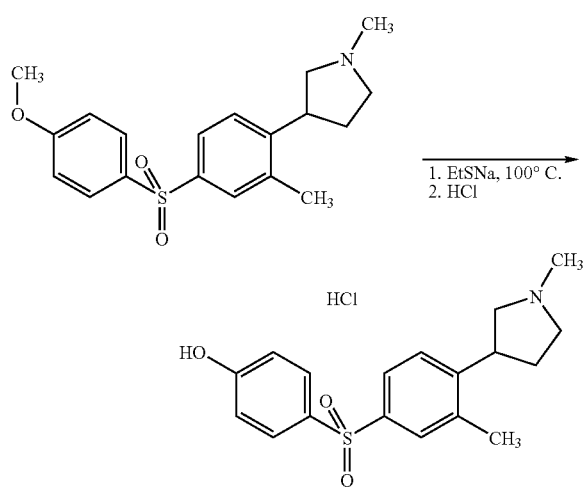

Sodium ethanethiolate (94 mg, 1.111 mmol) was added to a solution of 3-[4-(4-methoxy-benzenesulfonyl)-2-methyl-phenyl]-1-methyl-pyrrolidine (128 mg, 0.3705 mol) in DMF (2 mL) and the reaction mixture was heated at 100° C. for 4 hours. The solvent was evaporated under reduced pressure and the residue was purified via flash chromatography (DCM/MeOH/NH$_4$OH) to give 4-[3-methyl-4-(1-methyl-pyrrolidin-3-yl)-benzenesulfonyl]-phenol as a white foam. The free amine was transformed in the corresponding hydrochloride (white foam) by addition of a small excess of HCl in 1,4-dioxane: MP=186.0-187.5° C.

Example 5

3-[3-Methyl-4-(1-methyl-pyrrolidin-3-yl)-benzenesulfonyl]-phenol

The synthetic procedure described in this Example was carried out according to the process shown in Scheme N.

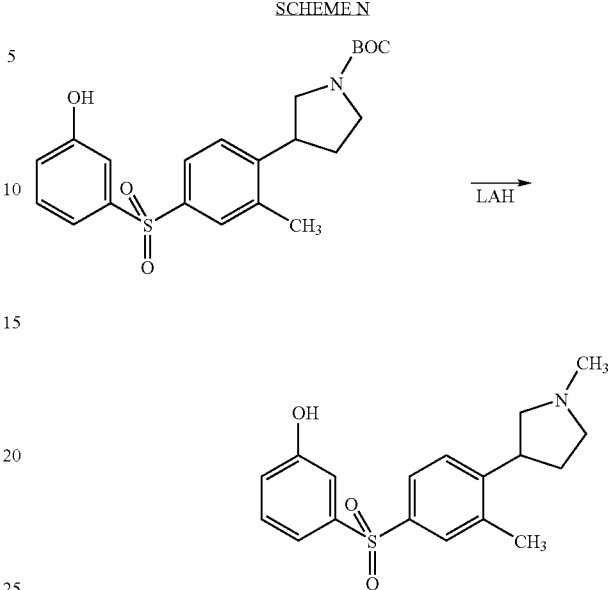

A solution of LAH (1.0 M in THF, 0.51 mL) was added to a solution of {3-[4-(3-hydroxy-benzenesulfonyl)-2-methyl-phenyl]-pyrrolidin-1-yl}-acetic acid tert-butyl ester (85 mg, 0.2036 mmol) in THF (1 mL). The reaction mixture was stirred at reflux for 2 hours, it was cooled to room temperature and Na$_2$SO$_4$·10H$_2$O was added. The mixture was filtered and the filtrate was evaporated under reduced pressure. The residue was purified via flash chromatography (DCM/MeOH/NH$_4$OH) to give 42 mg of 3-[3-methyl-4-(1-methyl-pyrrolidin-3-yl)-benzenesulfonyl]-phenol as a white foam: MS (M+H)=332.

Example 6

2-(3-Methoxy-4-pyrrolidin-3-yl-benzenesulfonyl)-benzonitrile

The synthetic procedure described in this Example was carried out according to the process shown in Scheme O.

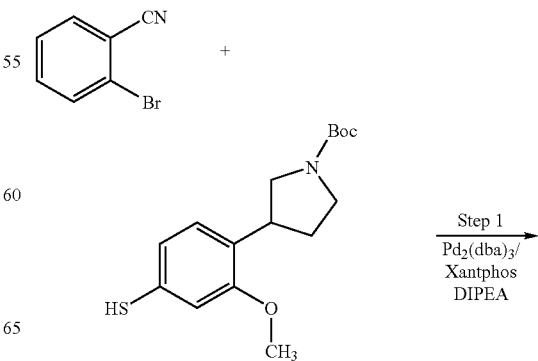

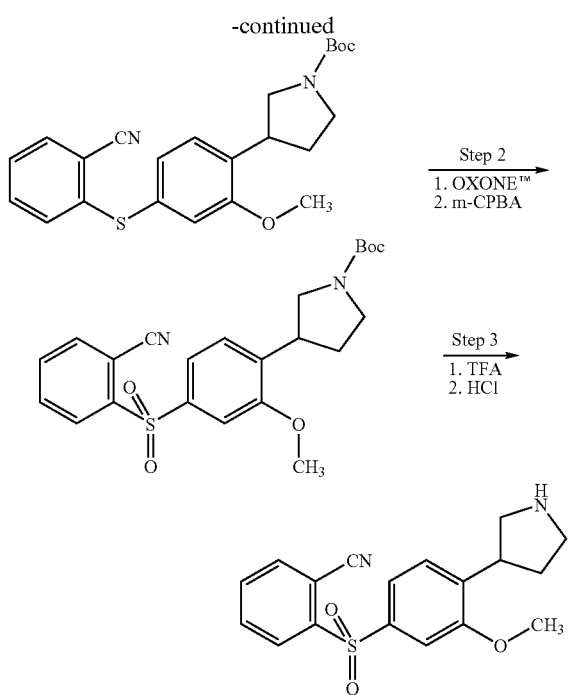

Step 1 3-[4-(2-Cyano-phenylsulfanyl)-2-methoxy-phenyl]-pyrrolidine-1-carboxylic acid tert-butyl ester Pd$_2$(dba)$_3$ (13 mg, 0.01414 mmol), Xantphos (16 mg, 0.02828 mmol), 2-bromobenzonitrile (0.103 mg, 0.5655 mmol) and DIPEA (0.103 mL, 1.131 mmol) were added to a solution of 3-(4-mercapto-2-methoxy-phenyl)-pyrrolidine-1-carboxylic acid tert-butyl ester (0.175 g, 0.5655 mmol) in 1,4-dioxane (10 mL). The reaction mixture was heated at reflux for 16 hours, then cooled and a solution of 10% KHSO$_4$/Na$_2$SO$_4$ was added. The mixture was extracted with EtOAc, and the combined organic extracts were washed with water and brine, dried over Na$_2$SO$_4$, filtered and evaporated under reduced pressure. The resulting crude material was purified via flash chromatography (hexane/EtOAc, 7/3) to give 0.209 g (90% yield) of 3-[4-(2-cyano-phenylsulfanyl)-2-methoxy-phenyl]-pyrrolidine-1-carboxylic acid tert-butyl ester as a clear oil.

Step 2 3-[4-(2-Cyano-benzenesulfonyl)-2-methoxy-phenyl]-pyrrolidine-1-carboxylic acid tert-butyl ester A solution of OXONE™ (0.470 g, 0.7636 mmol) in water (5 mL) was added to a solution of 3-[4-(2-cyano-phenylsulfanyl)-2-methoxy-phenyl]-pyrrolidine-1-carboxylic acid tert-butyl ester (0.209 g, 0.5091 mmol) in a mixture of MeOH (5 mL) and acetonitrile (5 mL). The reaction mixture was stirred at room temperature for 3 hours, then water was added and the mixture was extracted with EtOAc. The combined organic extracts were washed with water and brine, dried over Na$_2$SO$_4$, filtered, and evaporated under reduced pressure. The resulting crude material was purified via flash chromatography (hexane/EtOAc, 7/3) to give 0.215 g of 3-[4-(2-cyano-benzenesulfinyl)-2-methoxy-phenyl]-pyrrolidine-1-carboxylic acid tert-butyl ester (not shown in Scheme O) as a clear oil.

To 3-[4-(2-cyano-benzenesulfinyl)-2-methoxy-phenyl]-pyrrolidine-1-carboxylic acid tert-butyl ester (0.135 mg, 0.3165 mmol) dissolved in DCM (5 mL) was added m-CPBA (0.115 mg, 0.9495 mmol), and the mixture was stirred at room temperature for 6 hours. DCM was added and the resulting mixture was washed with sodium thiosulfate (10% aqueous solution), NaHCO$_3$ (saturated aqueous solution), water, and brine. The organic phase was then dried over Na$_2$SO$_4$, filtered, and evaporated under reduced pressure. The resulting crude material was purified via flash chromatography (hexane/EtOAc, 1/1) to give 0.125 g (89% yield) of 3-[4-(2-cyano-benzenesulfonyl)-2-methoxy-phenyl]-pyrrolidine-1-carboxylic acid tert-butyl ester as a clear oil.

Step 3 2-(3-Methoxy-4-pyrrolidin-3-yl-benzene-sulfonyl)-benzonitrile

3-[4-(2-Cyano-benzenesulfonyl)-2-methoxy-phenyl]-pyrrolidine-1-carboxylic acid tert-butyl ester was deprotected following the procedure described in Example 1. The free amine base was converted in the corresponding hydrochloride salt by addition of a small excess of HCl in 1,4-dioxane: MP=247.8-249.1° C.

Example 7

5-Fluoro-3-[3-methyl-4-(1-methyl-pyrrolidin-3-yl)-benzenesulfonyl]-1H-indole

The synthetic procedure described in this Example was carried out according to the process shown in Scheme P.

SCHEME P

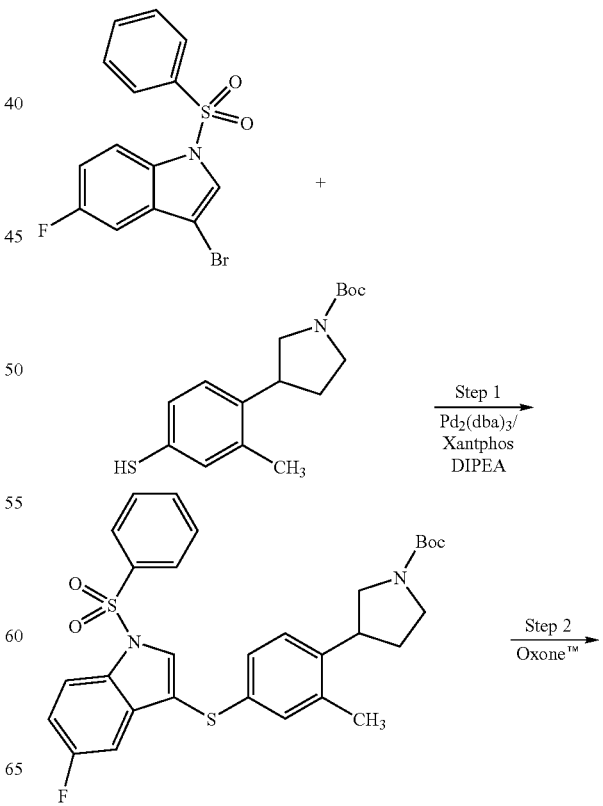

83

-continued

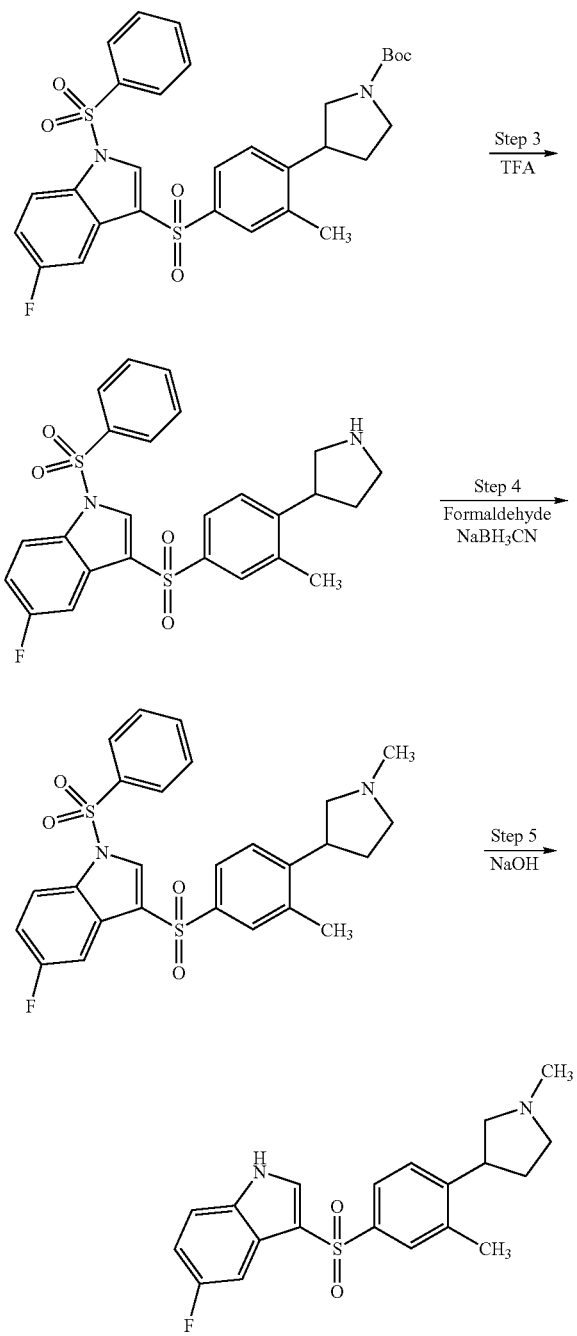

Step 1 3-[4-(1-Benzenesulfonyl-5-fluoro-1H-indol-3-ylsulfanyl)-2-methyl-phenyl]-pyrrolidine-1-carboxylic acid tert-butyl ester 3-(4-Mercapto-2-methyl-phenyl)-pyrrolidine-1-carboxylic acid tert-butyl ester was reacted with 1-benzenesulfonyl-3-bromo-5-fluoro-1H-indole using the procedure of step 1 of Example 3 to provide 3-[4-(1-Benzenesulfonyl-5-fluoro-1H-indol-3-ylsulfanyl)-2-methyl-phenyl]-pyrrolidine-1-carboxylic acid tert-butyl ester.

84

Step 2 3-[4-(1-Benzenesulfonyl-5-fluoro-1H-indole-3-sulfonyl)-2-methyl-phenyl]-pyrrolidine-1-carboxylic acid tert-butyl ester 3-[4-(1-Benzenesulfonyl-5-fluoro-1H-indol-3-ylsulfanyl)-2-methyl-phenyl]-pyrrolidine-1-carboxylic acid tert-butyl ester was oxidized to 3-[4-(1-benzenesulfonyl-5-fluoro-1H-indole-3-sulfonyl)-2-methyl-phenyl]-pyrrolidine-1-carboxylic, acid tert-butyl ester using the procedure of step 2 of Example 3.

Step 3 1-Benzenesulfonyl-5-fluoro-3-(3-methyl-4-pyrrolidin-3-yl-benzenesulfonyl)-1H-indole 3-[4-(1-Benzenesulfonyl-5-fluoro-1H-indole-3-sulfonyl)-2-methyl-phenyl]-pyrrolidine-1-carboxylic acid tert-butyl ester was deprotected using the procedure of step 3 of Example 3 to afford 1-Benzenesulfonyl-5-fluoro-3-(3-methyl-4-pyrrolidin-3-yl-benzenesulfonyl)-1H-indole, MS (M+H)=499.

Step 4 5-Benzenesulfonyl-5-fluoro-3-[3-methyl-4-(1-methyl-pyrrolidin-3-yl)-benzenesulfonyl]-1H-indole Formaldehyde (37% in water, 0.19 mL, 2.505 mmol) and sodium cyanoborohydride (63 mg, 1.002 mmol) were added to a solution of 1-benzenesulfonyl-5-fluoro-3-(3-methyl-4-pyrrolidin-3-yl-benzenesulfonyl)-1H-indole trifluoroacetate (0.305 mg, 0.5011 mmol) in acetonitrile (3 mL). The reaction mixture was stirred at room temperature for 2 hours, then buffered to pH 12 by addition of 1 M aqueous NaOH. The mixture was extracted with DCM, and the combined organic extracts were washed with water and brine, dried over $Na_2SO_4$, filtered and evaporated under reduced pressure. The resulting crude material was purified via flash chromatography (DCM/MeOH($NH_4OH$)) to give 0.209 g (81% yield) of 1-benzenesulfonyl-5-fluoro-3-[3-methyl-4-(1-methyl-pyrrolidin-3-yl)-benzenesulfonyl]-1H-indole as a white foam. MS (M+H)=513.

Step 5 5-Fluoro-3-[3-methyl-4-(1-methyl-pyrrolidin-3-yl)-benzenesulfonyl]-1H-indole An aqueous solution of NaOH (2 M, 0.8 mL) was added to a solution of 1-benzenesulfonyl-5-fluoro-3-[3-methyl-4-(1-methyl-pyrrolidin-3-yl)-benzenesulfonyl]-1H-indole (0.209 g, 0.4045 mmol) in MeOH (1 mL) and the resulting mixture was stirred at room temperature for 5 hours. The solvent was evaporated under reduced pressure and the crude material was purified via flash chromatography (DCM/MeOH/$NH_4OH$) to give 0.102 g of 5-fluoro-3-[3-methyl-4-(1-methyl-pyrrolidin-3-yl)-benzenesulfonyl]-1H-indole as a white foam. MP=86.5-93.5° C.; MS (M+H)=378.

Example 8

4-(3-Methyl-4-pyrrolidin-3-yl-benzenesulfonyl)-phenylamine

The synthetic procedure described in this Example was carried out according to the process shown in Scheme Q.

SCHEME Q

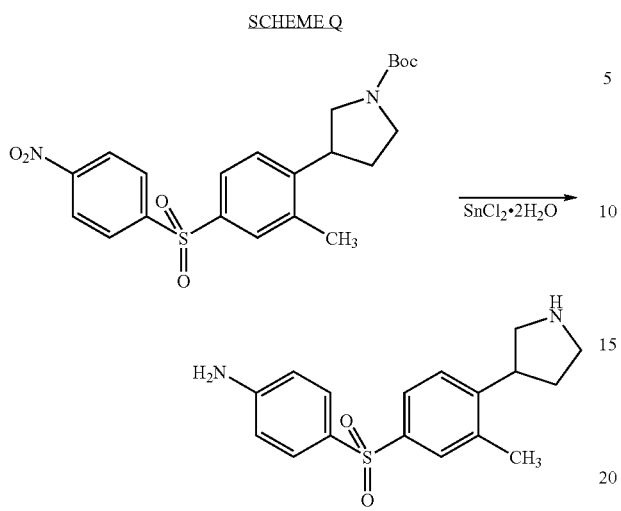

SnCl$_2$·2H$_2$O (1.74 g, 7.726 mmol) was added to a solution of 3-[2-methyl-4-(4-nitro-benzenesulfonyl)-phenyl]-pyrrolidine-1-carboxylic acid tert-butyl ester (0.69 g, 1.545 mmol) (prepared following the procedure described in Example 3) in isopropanol (20 mL) and the mixture was stirred at 75° C. for 2 hours. The reaction mixture was then cooled to 0° C. and a saturated solution of NaHCO$_3$ was added. The gelatinous material obtained was filtered and the solvent was evaporated under reduced pressure. The crude material was purified via flash chromatography (DCM/MeOH/NH$_4$OH) to give 0.407 g (83% yield) of 4-(3-methyl-4-pyrrolidin-3-yl-benzenesulfonyl)-phenylamine as a white foam: MS (M+H)=317.

Example 9

2-Chloro-4-(3-methyl-4-pyrrolidin-3-yl-benzenesulfonyl)-phenol

The synthetic procedure described in this Example was carried out according to the process shown in Scheme R.

SCHEME R

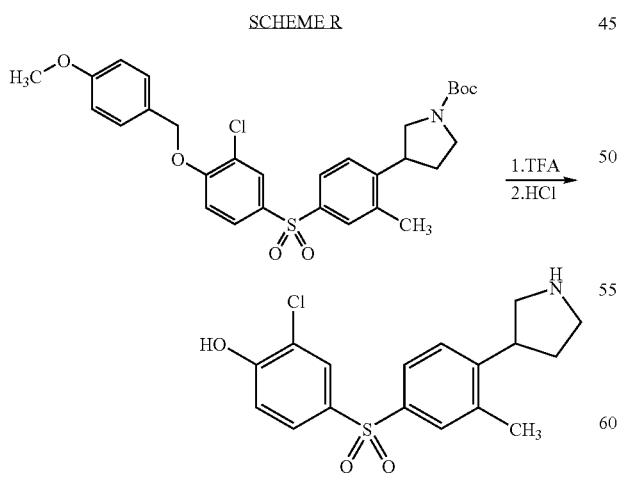

Trifluoroacetic acid was added to a solution of 3-{4-[3-chloro-4-(4-methoxy-benzyloxy)-benzenesulfonyl]-2-methyl-phenyl}-pyrrolidine-1-carboxylic acid tert-butyl ester (prepared following the procedure described in Example 6) (0.397 g, 0.6939 mmol) in DCM (2 mL). The reaction mixture was stirred at room temperature for 3 hours, and the solvent was then evaporated under reduced pressure. The crude residue was purified via flash chromatography (DCM/MeOH/NH$_4$OH) to give 0.143 g of 2-chloro-4-(3-methyl-4-pyrrolidin-3-yl-benzenesulfonyl)-phenol (white foam) that was transformed in the corresponding hydrochloride salt by addition of a small excess of HCl in 1,4-dioxane. The hydrochloride was recrystallized to afford 0.129 g of a white solid: MP=110.0-112.9° C.

Example 10

5-(3-Fluoro-benzenesulfonyl)-2-(S)-pyrrolidin-3-yl-phenol

The synthetic procedure described in this Example was carried out according to the process shown in Scheme S.

SCHEME S

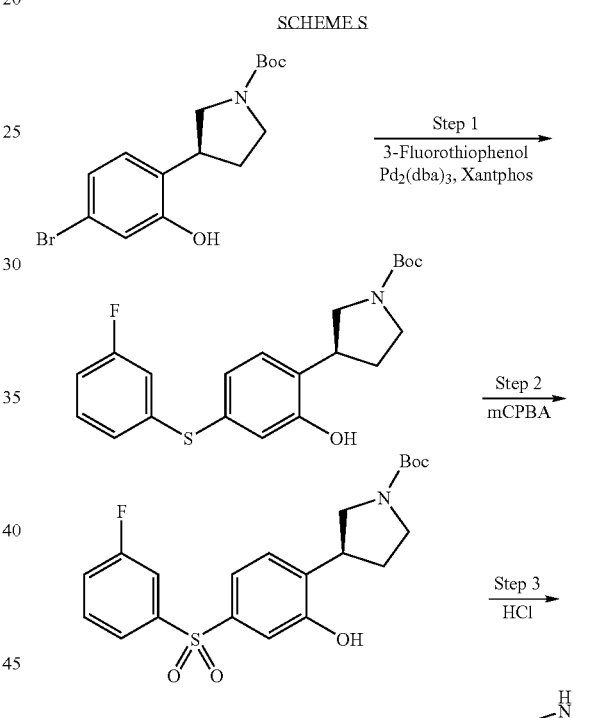

Step 1 (S)-3-[4-(3-Fluoro-phenylsulfanyl)-2-hydroxy-phenyl]-pyrrolidine-1-carboxylic acid tert-butyl ester 3-Fluorothiophenol (58 μL, 0.681 mmol), Tris(dibenzylideneacetone) dipalladium(0) (77.4 mg, 0.085 mmol), 4,5-Bis(diphenylphosphino)-9,9-dimethylxanthene (97.4 mg, 0.170 mmol) and DIPEA (0.156 mL, 1.71 mmol) were added to a solution of (S)-3-(4-bromo-2-hydroxy-phenyl)-pyrrolidine-1-carboxylic acid tert-butyl ester (233 mg, 0.681 mmol) in 1,4-dioxane (4.6 mL). The reaction mixture was heated at reflux for 18 hours, then cooled to 5° C. and a solution of 10% KHSO$_4$/Na$_2$SO$_4$ was added, followed by brine. The mixture was extracted with EtOAc, and the combined organic extracts were washed with brine, dried over Na$_2$SO$_4$, filtered through a celite pad, and evaporated under reduced pressure. The resulting crude material was purified via flash chromatography (hexane/acetone, 9/1) to give 187 mg (70% yield) of (S)-3-[4-(3-fluoro-phenylsulfanyl)-2-hydroxy-phenyl]-pyrrolidine-1-carboxylic acid tert-butyl ester as a white foam.

Step 2 (S)-3-[4-(3-Fluoro-benzenesulfonyl)-2-hydroxy-phenyl]-pyrrolidine-1-carboxylic acid tert-butyl ester m-CPBA (226.8 mg, 0.92 mmol) was added to a solution of (S)-3-[4-(3-fluoro-phenylsulfanyl)-2-hydroxy-phenyl]-pyrrolidine-1-carboxylic acid tert-butyl ester (182.5 mg, 0.469 mmol) in DCM (8 mL) at room temperature under argon atmosphere. The reaction mixture was stirred at room temperature for 2 hours, and then solution of sodium thisulphate (10%) was added. The organic layer was separated and washed with NaHCO$_3$ (10% aqueous solution), dried over Na$_2$SO$_4$, filtered and evaporated under reduced pressure. The resulting crude material was purified via flash chromatography (hexane/EtOAc, 65/35) to give 192 mg (97% yield) of (S)-3-[4-(3-fluoro-benzenesulfonyl)-2-hydroxy-phenyl]-pyrrolidine-1-carboxylic acid tert-butyl ester.

Step 3 5-(3-Fluoro-benzenesulfonyl)-2-(S)-pyrrolidin-3-yl-phenol hydrochloride A solution of HCl (4 M in 1,4-dioxane, 0.63 mL) was added to a solution of (S)-3-[4-(3-fluoro-benzenesulfonyl)-2-hydroxy-phenyl]-pyrrolidine-1-carboxylic acid tert-butyl ester (177.5 mg, 0.421 mmol) in 1,4-dioxane (1 mL) under nitrogen atmosphere. The reaction mixture was stirred at room temperature for 7.5 hours. The reaction mixture was filtered and the white solid was collected and washed with 1,4-dioxane and dried under reduced pressure to afford 111 mg (74% yield) of 5-(3-fluoro-benzenesulfonyl)-2-(S)-pyrrolidin-3-yl-phenol hydrochloride. MP=239-241° C.

Similarly prepared was 5-(3-Fluoro-benzenesulfonyl)-2-(R)-pyrrolidin-3-yl-phenol; Mp=239.0-241.0° C.

Example 11

5-[4-((S)-1-Methyl-pyrrolidin-3-yl)-benzenesulfonyl]-1H-indazole

The synthetic procedure described in this Example was carried out according to the process shown in Scheme T.

SCHEME T

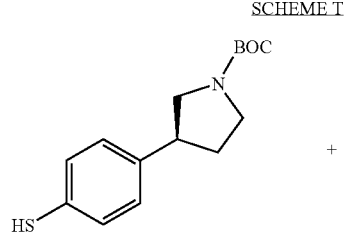

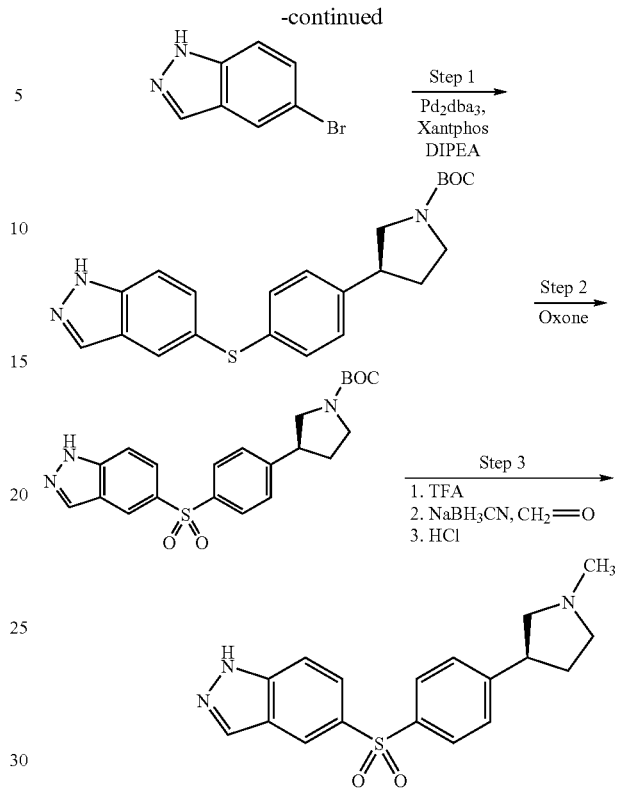

Step 1 (S)-3-[4-(1H-Indazol-5-ylsulfanyl)-phenyl]-pyrrolidine-1-carboxylic acid tert-butyl ester 5-Bromo-1H-indazole (200.9 mg, 1.02 mmol), Pd$_2$(dba)$_3$ (115.9 mg), Xantphos (145.9 mg) and DIPEA (0.188 mL) were added to a solution of (S)-3-(4-mercapto-phenyl)-pyrrolidine-1-carboxylic acid tert-butyl ester (285 mg, 1.02 mmol) in 1,4-dioxane (4 mL) under argon atmosphere. The reaction mixture was heated at 100° C. for 18 hours, then cooled to 5° C. and a solution of 10% KHSO$_4$/Na$_2$SO$_4$ was added. The mixture was filtered, the filter cake was washed with EtOAc, and the filtrate was extracted with EtOAc. The combined organic extracts were washed with brine, dried over Na$_2$SO$_4$, filtered, and evaporated under reduced pressure. The resulting crude material was purified via flash chromatography (hexane/EtOAc, 7/3) to give 252 mg (62% yield) of (S)-3-[4-(1H-indazol-5-ylsulfanyl)-phenyl]-pyrrolidine-1-carboxylic acid tert-butyl ester.

Step 2 (S)-3-[4-(1H-Indazole-5-sulfonyl)-phenyl]-pyrrolidine-1-carboxylic acid tert-butyl ester OXONE™ (627.3 mg, 1.02 mmol) was added to a solution of (S)-3-[4-(1H-indazol-5-ylsulfanyl)-phenyl]-pyrrolidine-1-carboxylic acid tert-butyl ester (201.8 mg, 0.510 mmol) in a mixture of acetonitrile (3.1 mL), methanol (3.1 mL) and water (2.5 mL). The reaction mixture was vigorously stirred for 4 hours. Water was then added and the mixture was extracted twice with EtOAc. The combined organic extracts were washed with brine and dried over Na$_2$SO$_4$. The solvent was evaporated under reduced pressure and the crude material was purified via flash chromatography (hexane/EtOAc, 1/1) to give 204.5 mg (94% yield) of (S)-3-[4-(1H-indazole-5-sulfonyl)-phenyl]-pyrrolidine-1-carboxylic acid tert-butyl ester as colorless oil.

Step 4 5-[4-((S)-1-Methyl-pyrrolidin-3-yl)-benzenesulfonyl]-1H-indazole hydrochloride Trifluoroacetic acid (3.4 mL) was added to a solution of (S)-3-[4-(1H-indazole-5-sulfonyl)-phenyl]-pyrrolidine-1-carboxylic acid tert-butyl ester (193.4 mg, 0.452 mmol) in DCM (3.4 mL) under nitrogen atmosphere. The reaction mixture was stirred at room temperature for 1 hour. The solvent was evaporated under reduced pressure, and the residue was dissolved in acetonitrile (4 mL). Formaldehyde (37% in water, 0.181 mL) was added, under nitrogen atmosphere, to this material followed by sodiumcyanoborohydride (85 mg). The reaction mixture was stirred for 1.5 hour, and then a saturated solution of $Na_2CO_3$ was then added. The mixture was extracted with DCM, and the combined organic extracts were dried over $Na_2SO_4$, filtered, and evaporated under reduced pressure. The crude material was dissolved in HCl (2 M, 10 mL) and the resulting mixture was stirred for 8 hours. Solvent was evaporated under reduced pressure and the crude residue was purified via flash chromatography (DCM/MeOH/$NH_4OH$) to give 89.2 mg of 5-[4-((S)-1-methyl-pyrrolidin-3-yl)-benzenesulfonyl]-1H-indazole which was treated with 1,4-dioxane (2 mL) and transformed into 83.3 mg of the corresponding hydrochloride salt by addition of HCl (4 M in 1,4-dioxane, 0.84 mL). MS (M+H)=342.

Example 12

4-[4-((S)-1-Methyl-pyrrolidin-3-yl)-benzenesulfonyl]-phenol hydrochloride

The synthetic procedure described in this Example was carried out according to the process shown in Scheme U.

SCHEME U

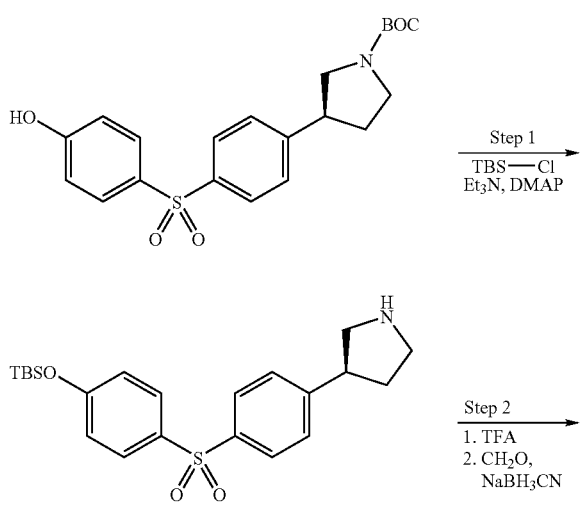

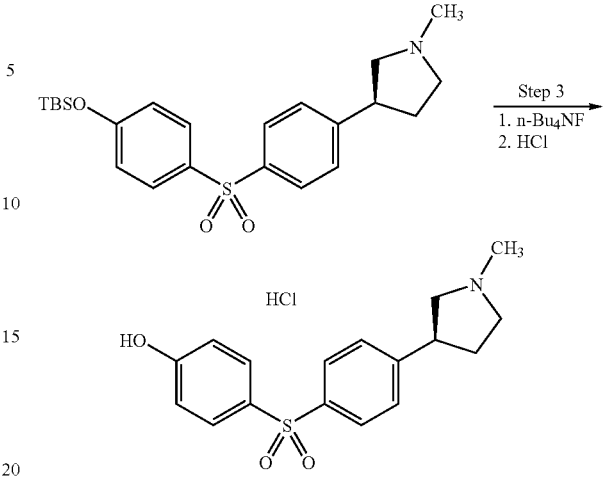

Step 1

(S)-3-[4-[4-(tert-Butyl-dimethyl-silanyloxy)-benzenesulfonyl]-phenyl]-pyrrolidine-1-carboxylic acid tert-butyl ester t-Butyldimethylchlorosilane (116.55 mg, 0.773 mmol), TEA (0.1336 mL, 0.975 mmol) and DMAP (9 mg, 0.0736 mmol) were added to a solution of (S)-3-[4-(4-hydroxy-benzenesulfonyl)-phenyl]-pyrrolidine-1-carboxylic acid tert-butyl ester (297 mg, 0.736 mmol) in DCM (5 mL) under argon atmosphere. The reaction mixture was stirred at room temperature for 3 hours. and then a solution of 10% $KHSO_4$/$Na_2SO_4$ was added. The mixture was extracted with DCM, and the combined organic extracts were washed with $NaHCO_3$ (10% aqueous solution), dried over $Na_2SO_4$, filtered, and evaporated under reduced pressure. The resulting crude material was purified via flash chromatography (hexane/EtOAc, 783/17) to give 370.6 mg (97% yield) of (S)-3-{4-[4-(tert-butyl-dimethyl-silanyloxy)-benzenesulfonyl]-phenyl}-pyrrolidine-1-carboxylic acid tert-butyl ester as a foam.

Step 2 (S)-3-{4-[4-(tert-butyl-dimethyl-silanyloxy)-benzenesulfonyl]-phenyl}-1-methyl-pyrrolidine Trifluoroacetic acid (5 mL) was added to a solution of (S)-3-{4-[4-(tert-butyl-dimethyl-silanyloxy)-benzenesulfonyl]-phenyl}-pyrrolidine-1-carboxylic acid tert-butyl ester (342 mg, 0.661 mmol) in DCM (5 mL) under argon atmosphere. The mixture was stirred at room temperature for 75 minutes, then solvent was evaporated under reduced pressure. The crude material (482.9 mg) was dissolved in acetonitrile (5 mL) and to the resulting solution, under argon atmosphere, was added formaldehyde (37% in water, 0.264 mL, 3.292 mmol) followed by sodium cyanoborohydride (82.4 mg, 1.316 mmol). The reaction mixture was stirred at room temperature for 1.5 hours, then buffered to pH 12. The resulting mixture was extracted with DCM, and the combined organic extracts were dried over $Na_2SO_4$, filtered, and evaporated under reduced pressure. The resulting crude material was purified via flash chromatography (DCM/MeOH/$NH_4OH$) to give 248.2 mg (87% yield) of (S)-3-{4-[4-(tert-butyl-dimethyl-silanyloxy)-benzenesulfonyl]-phenyl}-1-methyl-pyrrolidine as a colorless oil which solidified upon standing.

Step 3 4-[4-((S)-1-Methyl-pyrrolidin-3-yl)-benzenesulfonyl]-phenol hydrochloride A solution of n-tetrabutylammoniumfluoride (1.0 M in THF, 0.593 mL, 0.59 mmol), was added to a solution of (S)-3-{4-[4-(tert-butyl-dimethyl-silanyloxy)-benzenesulfonyl]-phenyl}-1-methyl-pyrrolidine (242 mg, 0.561 mmol) in THF (2 mL) at 0-5° C. under argon atmosphere. The reaction mixture was stirred at 0-5° C. for 1 hour and then concentrated under reduced pressure. The crude residue was purified by preparative TLC (DCM/MeOH/NH$_4$OH) to give 122 mg of 4-[4-((S)-1-methyl-pyrrolidin-3-yl)-benzenesulfonyl]-phenol. The amine (119 mg) was dissolved in isopropanol (2 mL) and was treated with HCl (4 M in 1,4-dioxane, 0.12 mL, 0.487 mL) under nitrogen atmosphere. The mixture was stirred for one hour and the white solid formed was collected by filtration, washed with isopropanol and dried under reduced pressure to give 63 mg of 4-[4-((S)-1-methyl-pyrrolidin-3-yl)-benzenesulfonyl]-phenol hydrochloride, MP=197-199° C.

Example 13

2-[5-(3-Fluoro-benzenesulfonyl)-2-pyrrolidin-3-yl-phenoxy]-ethanol

The synthetic procedure described in this Example was carried out according to the process shown in Scheme V.

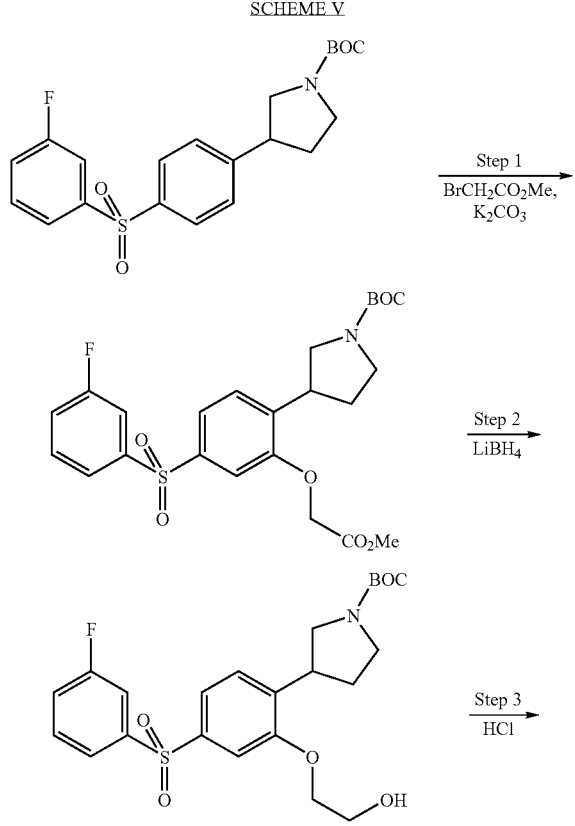

SCHEME V

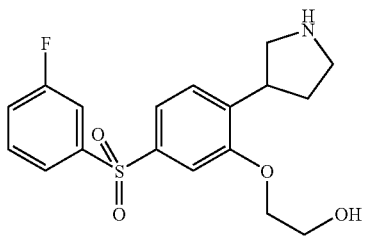

Step 1 3-[4-(3-Fluoro-benzenesulfonyl)-2-hydroxy-phenyl]-pyrrolidine-1-carboxylic acid tert-butyl ester Methyl bromoacetate (47 L, 0.495 mmol), followed by potassium carbonate (136.7 mg, 0.99 mmol) were added to a solution of 3-[4-(3-fluoro-benzenesulfonyl)-2-hydroxy-phenyl]-pyrrolidine-1-carboxylic acid tert-butyl ester (198.7 mg, 0.471 mmol) in acetone (5 mL) under argon atmosphere. The reaction mixture was stirred at room temperature for 4 hours, then filtered and the solvent was evaporated under reduced pressure to give 240.9 mg of 3-[4-(3-fluoro-benzenesulfonyl)-2-methoxycarbonylmethoxy-phenyl]-pyrrolidine-1-carboxylic acid tert-butyl ester, which was used without further purification in the next step.

Step 2 3-[4-(3-Fluoro-benzenesulfonyl)-2-(2-hydroxy-ethoxy)-phenyl]-pyrrolidine-1-carboxylic acid tert-butyl ester 3-[4-(3-Fluoro-benzenesulfonyl)-2-hydroxy-phenyl]-pyrrolidine-1-carboxylic acid tert-butyl ester (120 mg) was dissolved in THF (2 mL) and lithiumborohydride (7.94 mg, 0.365 mmol) was added under argon atmosphere. The reaction mixture was stirred at room temperature for 6 hours, then cooled to 0-5° C. and a solution of 10% KHSO$_4$/Na$_2$SO$_4$ was carefully added until pH 2 was reached. The resulting mixture was extracted with EtOAc, and the combined organic extracts were washed with brine, dried over Na$_2$SO$_4$, filtered and evaporated under reduced pressure. The resulting crude material was purified via flash chromatography (hexane/EtOAc, 1/1) to give 103 mg (91% yield) of 3-[4-(3-fluoro-benzenesulfonyl)-2-(2-hydroxy-ethoxy)-phenyl]-pyrrolidine-1-carboxylic acid tert-butyl ester.

Step 3

2-[5-(3-Fluoro-benzenesulfonyl)-2-pyrrolidin-3-yl-phenoxy]-ethanol

A solution of HCl (4 M in 1,4-dioxane, 0.3 mL, 1.2 mmol) was added to a solution of 3-[4-(3-fluoro-benzenesulfonyl)-2-(2-hydroxy-ethoxy)-phenyl]-pyrrolidine-1-carboxylic acid tert-butyl ester (100 mg, 0.215 mmol) in 1,4-dioxane (1 mL) under nitrogen atmosphere. The reaction mixture was stirred for 4 hours The solvent was then evaporated under reduced pressure to give 82 mg of 2-[5-(3-fluoro-benzenesulfonyl)-2-pyrrolidin-3-yl-phenoxy]-ethanol hydrochloride as a foam. MS (M+H)=366.

Example 14

2-[5-(3-Fluoro-benzenesulfonyl)-2-pyrrolidin-3-yl-phenoxy]-N-methyl-acetamide The synthetic procedure described in this Example was carried out according to the process shown in Scheme W.

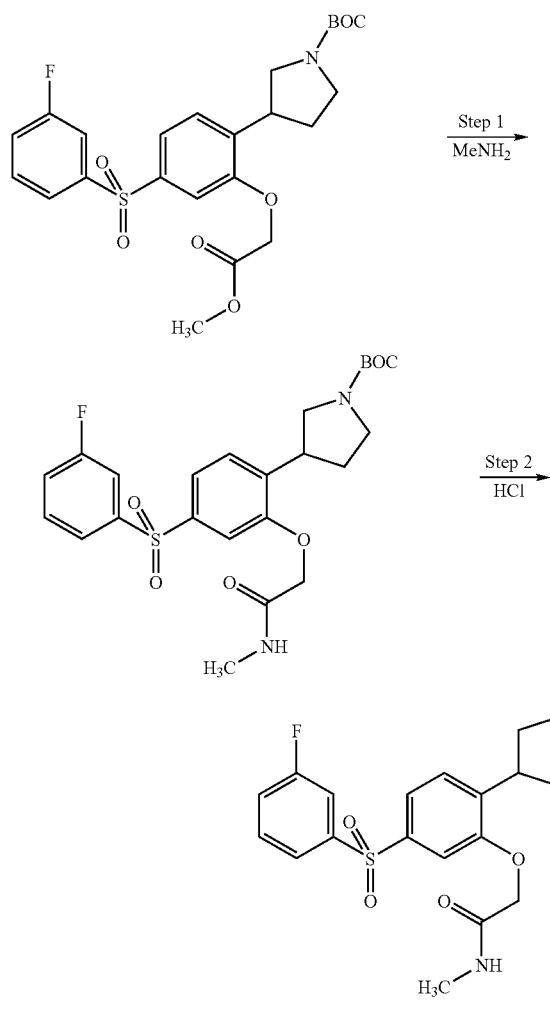

Step 1  3-[4-(3-Fluoro-benzenesulfonyl)-2-methylcarbamoylmethoxy-phenyl]-pyrrolidine-1-carboxylic acid tert-butyl ester A mixture of 3-[4-(3-fluoro-benzenesulfonyl)-2-methoxycarbonylmethoxy-phenyl]-pyrrolidine-1-carboxylic acid tert-butyl ester (120 mg, prepared as described in Example 13) and methylamine (2M in THF, 1.2 mL) was heated at 90° C. in a sealed tube for 16 hours. The reaction mixture was cooled and concentrated under reduced pressure, and the crude residue was purified via flash chromatography (hexane/EtOAc, 3/7) to give 109 mg of 3-[4-(3-fluoro-benzenesulfonyl)-2-methylcarbamoylmethoxy-phenyl]-pyrrolidine-1-carboxylic acid tert-butyl ester as a colorless oil.

Step 2

2-[5-(3-Fluoro-benzenesulfonyl)-2-pyrrolidin-3-yl-phenoxy]-N-methyl-acetamide 3-[4-(3-Fluoro-benzenesulfonyl)-2-methylcarbamoylmethoxy-phenyl]-pyrrolidine-1-carboxylic acid tert-butyl ester was deprotected using HCl in 1,4-dioxane following the procedure described in Example 13, to afford 2-[5-(3-Fluoro-benzenesulfonyl)-2-pyrrolidin-3-yl-phenoxy]-N-methyl-acetamide as a hydrochloride salt. MS (M+H)=393.

Example 15

2-{3-[4-(3-Fluoro-benzenesulfonyl)-2-methyl-phenyl]-pyrrolidin-1-yl}-ethanol The synthetic procedure described in this Example was carried out according to the process shown in Scheme X.

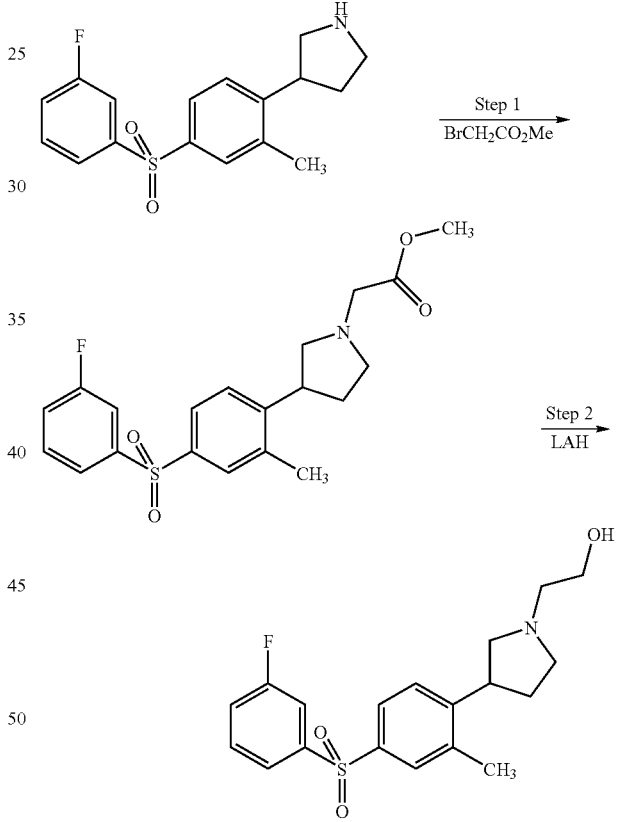

Step 1  {3-[4-(3-Fluoro-benzenesulfonyl)-2-methyl-phenyl]-pyrrolidin-1-yl}-acetic acid methyl ester Triethylamine (0.387 mL, 1.533 mmol) and methyl bromoacetate (0.146 mL, 1.533 mmol) were added at 0° C. to a solution of 3-[4-(3-fluoro-benzenesulfonyl)-2-methyl-phenyl]-pyrrolidine (0.445 g, 1.393 mmol) in DCM (5 mL). The reaction mixture was stirred at room temperature for 4 hours, then concentrated under reduced pressure, and the crude residue was purified via flash chromatography (DCM/MeOH/NH$_4$OH) to give 0.410 g (84% yield) of {3-[4-(3-fluorobenzenesulfonyl)-2-methyl-phenyl]-pyrrolidin-1-yl}-acetic acid methyl ester as a yellow oil.

Step 2 2-{3-[4-(3-Fluoro-benzenesulfonyl)-2-methyl-phenyl]-pyrrolidin-1-yl}-ethanol Lithium alluminiumhydride (1.0 M in THF, 0.51 mL) was added to a solution of {3-[4-(3-fluoro-benzenesulfonyl)-2-methyl-phenyl]-pyrrolidin-1-yl}-acetic acid methyl ester (100 mg, 0.2554 mmol) in THF (1 mL) and the resulting mixture was stirred at room temperature for 1 hour. Water was slowly added and the mixture was extracted with DCM. The combined organic extracts were washed with water and brine, dried over $Na_2SO_4$, filtered, and evaporated under reduced pressure. The resulting crude material was purified via flash chromatography (DCM/MeOH/$NH_4OH$) to give 7 mg of 2-{3-[4-(3-fluoro-benzenesulfonyl)-2-methyl-phenyl]-pyrrolidin-1-yl}-ethanol, MS (M+H)=364.

Example 16

2-{3-[4-(3-Fluoro-benzenesulfonyl)-2-methyl-phenyl]-pyrrolidin-1-yl}-acetamide

The synthetic procedure described in this Example was carried out according to the process shown in Scheme Y.

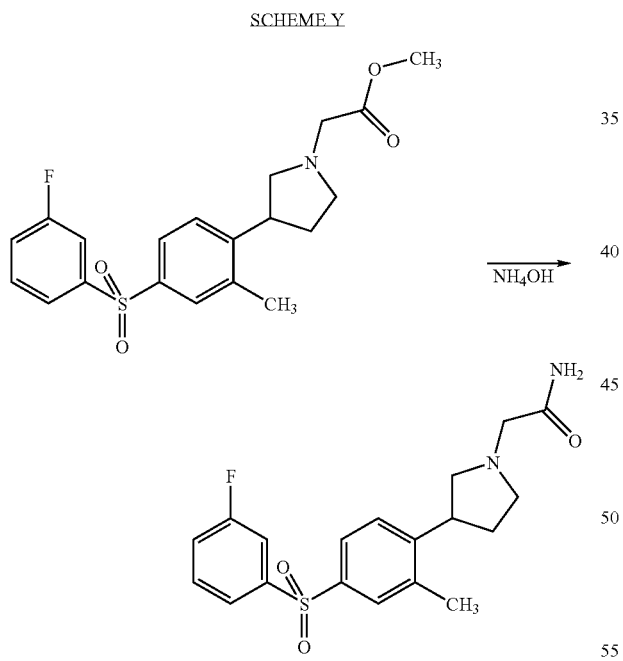

A concentrated solution of ammonium hydroxide (2 mL) was added to a solution of {3-[4-(3-fluoro-benzenesulfonyl)-2-methyl-phenyl]-pyrrolidin-1-yl}-acetic acid methyl ester (130 mg, 0.3321 mmol) in methanol (2 mL) and the resulting mixture was stirred at room temperature for 16 hours. Solvent was evaporated under reduced pressure and the crude material was purified via flash chromatography (DCM/MeOH/$NH_4OH$) to give 0.102 g of 2-{3-[4-(3-fluoro-benzenesulfonyl)-2-methyl-phenyl]-pyrrolidin-1-yl}-acetamide of a white foam: MS (M+H)=377.

Example 17

5-(3-Fluoro-benzenesulfonyl)-2-pyrrolidin-3-yl-benzoic acid ethyl ester

The synthetic procedure described in this Preparation was carried out using the procedure of Scheme Z.

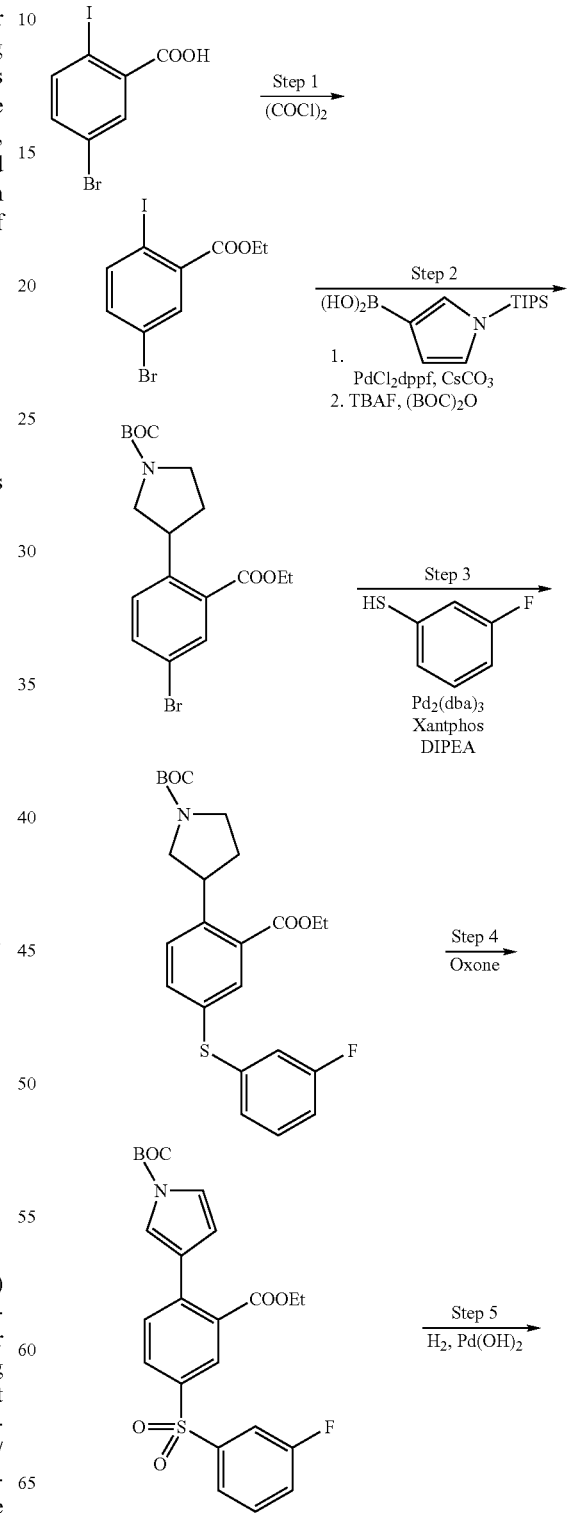

-continued

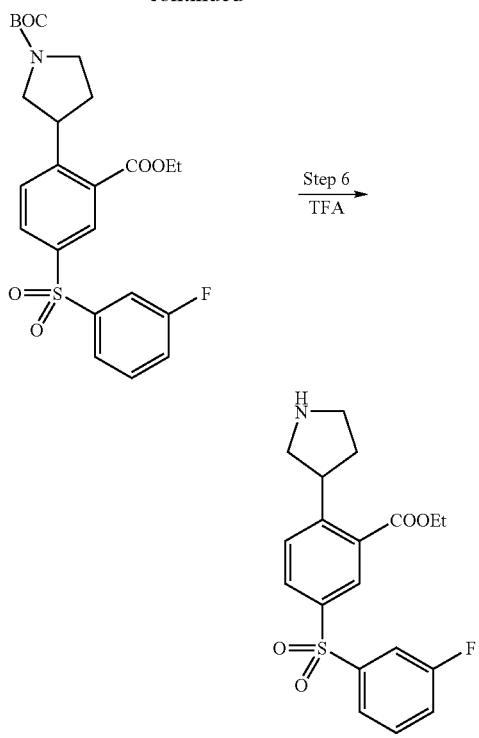

Step 6
TFA

Step 1 5-Bromo-2-iodo-benzoic acid ethyl ester

5-Bromo-2-iodo-benzoic acid (25.0 g, 76.47 mol) was dissolved in $CH_2Cl_2$ (75 ml) at room temperature. Oxalyl chloride (14.5 ml, 152.94 mmol) was added and the mixture was stirred at 40° C. for 30 minutes. The mixture was allowed to cool to room temperature and EtOH (6.69 ml, 114.71 mmol) was added. The mixture was concentrated under reduced pressure to give 27.2 g (quantitative) of 5-bromo-2-iodo-benzoic acid ethyl ester as a yellow crystalline solid.

Step 2 3-(4-Bromo-2-ethoxycarbonyl-phenyl)-pyrrole-1-carboxylic acid tert-butyl ester 5-Bromo-2-iodo-benzoic acid ethyl ester (3.93 g, 11.07 mmol), triisopropylsilanyl-1H-pyrrole-3-boronic acid (2.96 g, 11.07 mmol), $PdCl_2dppf$ (443 mg, 0.55 mmol) and $CsCO_3$ (4.32 g, 13.28 mmol) were dissolved in 100 ml of a mixture of DME and Water (9:1). The mixture was heated to 80° C. overnight. Upon cooling, the mixture was diluted with water and extracted with $Et_2O$. The ether extracts were washed with brine, dried over $Na_2SO_4$ and concentrated under reduced pressure. The residue was immediately diluted in THF. $(Boc)_2O$ (2.42 g, 11.07 mmol) was added followed by TBAF (11.07 ml, 11.07 mmol). The mixture was allowed to stir for 2 hours at room temperature, the mixture was diluted with water, extracted with $Et_2O$. The combined ether extracts were washed with brine, dried over $Na_2SO_4$, filtered and concentrated under reduced pressure to give 1.648 g (37.77%) of 3-(4-bromo-2-ethoxycarbonyl-phenyl)-pyrrole-1-carboxylic acid tert-butyl ester as a clear oil which used in step 3 without further purification.

Step 3 3-[2-Ethoxycarbonyl-4-(3-fluoro-phenylsulfanyl)-phenyl]-pyrrole-1-carboxylic acid tert-butyl ester 3-(4-Bromo-2-ethoxycarbonyl-phenyl)-pyrrole-1-carboxylic acid tert-butyl ester (1.65 g, 4.180 mmol) was dissolved in 25 ml of dioxane. Tris(dibenzylideneacetone) dipalladium(0) (478 mg. 0.522 mmol), 4,5-bis(diphenylphosphino)-9,9-dimethylxanthene (605 mg, 1.044 mmol), and DIPEA (1.82 ml, 10.45 mmol) were added followed by 3-fluorothiophenol (0.353 ml, 4.180 mmol). The mixture was heated to 90° C. overnight. The mixture was cooled to 5° C. and diluted with pH 2 buffer. Brine was added and the mixture was extracted with EtOAc. The combined extracts were washed with brine, dried over $Na_2SO_4$, filtered through a GF/F filter and concentrated under reduced pressure. The residue was purified by flash chromatography (Hexane/EtOAc 9/1) to give 983 mgs (53.02%) of 3-[2-Ethoxycarbonyl-4-(3-fluoro-phenylsulfanyl)-phenyl]-pyrrole-1-carboxylic acid tert-butyl ester as a clear oil.

Step 4 3-[2-Ethoxycarbonyl-4-(3-fluoro-benzenesulfonyl)-phenyl]-pyrrole-1-carboxylic acid tert-butyl ester 3-[2-Ethoxycarbonyl-4-(3-fluoro-phenylsulfanyl)-phenyl]-pyrrole-1-carboxylic acid tert-butyl ester (983 mg, 2.226 mmol) was dissolved in 10 ml of a (1:1) mixture of acetonitrile and MeOH. A solution of Oxone (2.053 g, 3.390 mmol) in 5 ml water was added and the mixture was allowed to stir at room temperature for 3 hours. The mixture was diluted with water and extracted with EtOAc. The combined organic extracts were dried over $Na_2SO_4$ and concentrated under reduced pressure. The residue was purified by flash chromatography (Hexanes/Acetone 9/1) to give 906 mgs (86%) of 3-[2-Ethoxycarbonyl-4-(3-fluoro-benzenesulfonyl)-phenyl]-pyrrole-1-carboxylic acid tert-butyl ester as a clear oil.

Step 5 3-[2-Ethoxycarbonyl-4-(3-fluoro-benzenesulfonyl)-phenyl]-pyrrolidine-1-carboxylic acid tert-butyl ester 3-[2-Ethoxycarbonyl-4-(3-fluoro-benzenesulfonyl)-phenyl]-pyrrole-1-carboxylic acid tert-butyl ester (288 mg, 0.608 mmol) was dissolved in 40 ml of MeOH. $Pd(OH)_2$ (200 mg) was added and the mixture was placed in a Parr bomb and stirred under 200 psi of Hydrogen for 72 hours. The solution was filtered through Celite and the filtrate was concentrated under reduced pressure to give 290 mgs (quantitative) of 3-[2-Ethoxycarbonyl-4-(3-fluoro-benzenesulfonyl)-phenyl]-pyrrolidine-1-carboxylic acid tert-butyl ester as a white crystalline solid.

Step 6 5-(3-Fluoro-benzenesulfonyl)-2-pyrrolidin-3-yl-benzoic acid ethyl ester 3-[2-Ethoxycarbonyl-4-(3-fluoro-benzenesulfonyl)-phenyl]-pyrrolidine-1-carboxylic acid tert-butyl ester (71 mg, 0.149 mmol) was dissolved in 2 ml of $CH_2Cl_2$. TFA (0.5 ml) was added and the mixture was stirred for 4 hours. The solution was concentrated under reduced pressure to give 5-(3-Fluoro-benzenesulfonyl)-2-pyrrolidin-3-yl-benzoic acid ethyl ester, MS (M+H)=378.

Example 18

[5-(3-Fluoro-benzenesulfonyl)-2-pyrrolidin-3-yl-phenyl]-methanol

The synthetic procedure described in this Preparation was carried out using the procedure of Scheme AA.

SCHEME AA

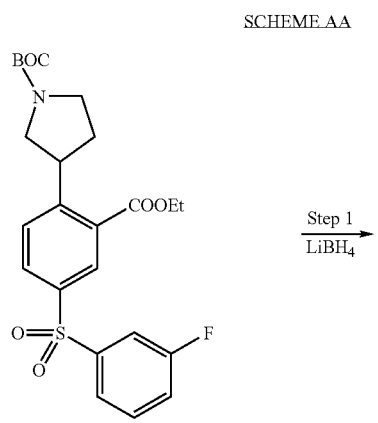

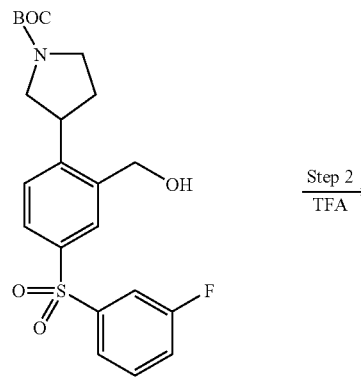

Step 1 3-[4-(3-Fluoro-benzenesulfonyl)-2-hydroxymethyl-phenyl]-pyrrolidine-1-carboxylic acid tert-butyl ester 3-[2-Ethoxycarbonyl-4-(3-fluoro-benzenesulfonyl)-phenyl]-pyrrolidine-1-carboxylic acid tert-butyl ester (136 mg, 0.285 mmol) was dissolved in 25 ml of THF. LiBH$_4$ (9.3 mg, 0.428 mmol) was added and the mixture was stirred at room temperature for 4 hours. The reaction was quenched by the addition of pH2 buffer and extracted with EtOAc. The combined extracts were dried over Na$_2$SO$_4$ and concentrated under reduced pressure. The residue was purified by flash chromatography (CH$_2$Cl$_2$/MeOH 95/5) to give 139 mg (quantitative) of 3-[4-(3-Fluoro-benzenesulfonyl)-2-hydroxymethyl-phenyl]-pyrrolidine-1-carboxylic acid tert-butyl ester as a clear oil.

Step 2 [5-(3-Fluoro-benzenesulfonyl)-2-pyrrolidin-3-yl-phenyl]-methanol

3-[4-(3-Fluoro-benzenesulfonyl)-2-hydroxymethyl-phenyl]-pyrrolidine-1-carboxylic acid tert-butyl ester (55 mg. 0.126 mmol) was dissolved in 2 ml of CH$_2$Cl$_2$. TFA (0.5 ml) was added and the mixture was stirred for 5 hours. The solution was concentrated under reduced pressure to give [5-(3-Fluoro-benzenesulfonyl)-2-pyrrolidin-3-yl-phenyl]-methanol; compound with oxalic acid as a brown gum, MS (M+H)=336.

Example 19

Dimethyl-carbamic acid 5-(3-fluoro-benzenesulfonyl)-2-pyrrolidin-3-yl-benzyl ester The synthetic procedure described in this Preparation was carried out using the procedure of Scheme BB.

SCHEME BB

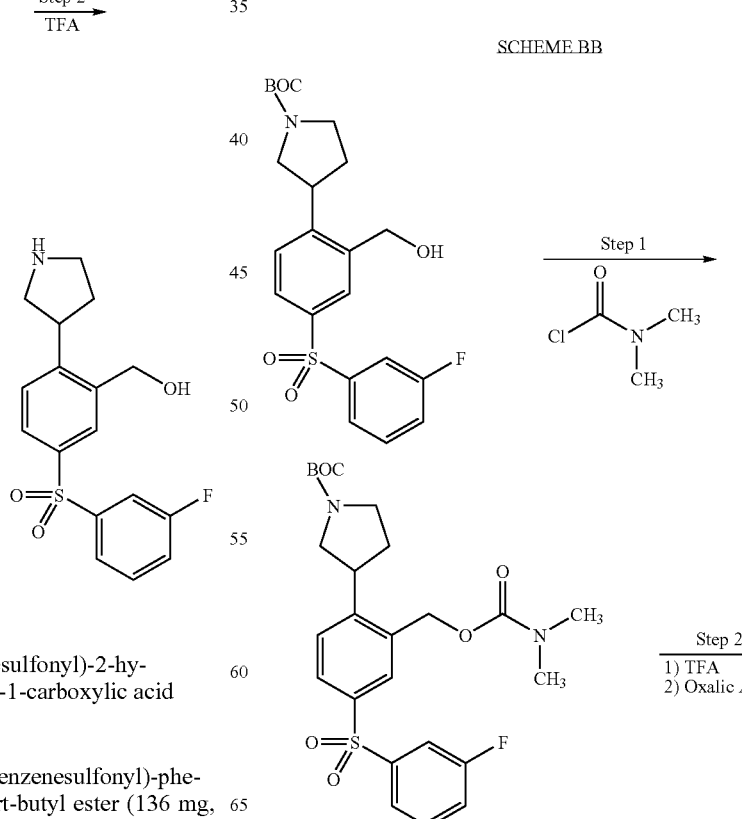

-continued

Step 1 3-[2-Dimethylcarbamoyloxymethyl-4-(3-fluoro-benzenesulfonyl)-phenyl]-pyrrolidine carboxylic acid tert-butyl ester 3-[4-(3-Fluoro-benzenesulfonyl)-2-hydroxymethyl-phenyl]-pyrrolidine-1-carboxylic acid tert-butyl ester (74 mg, 0.170 mmol) was dissolved in 25 ml of THF and the mixture was cooled to −78° C. LDA (0.102 ml, 0.204 mmol) was added and allowed to stir for 30 minutes. Dimethylcarbamoyl chloride (0.023 ml, 0.255 mmol) was added and the mixture was allowed to warm to room temperature over 3 hours. The mixture was diluted with water and extracted with EtOAc. The combined organic extracts were dried over $Na_2SO_4$, filtered, and concentrated under reduced pressure. The residue was purified by flash chromatography ($CH_2Cl_2$/MeOH 95/5) to give 83 mgs (96%) of 3-[2-Dimethylcarbamoyloxymethyl-4-(3-fluoro-benzenesulfonyl)-phenyl]-pyrrolidine-1-carboxylic acid tert-butyl ester as a clear oil.

Step 2 Dimethyl-carbamic acid 5-(3-fluoro-benzenesulfonyl)-2-pyrrolidin-3-yl-benzyl ester 3-[2-Dimethylcarbamoyloxymethyl-4-(3-fluoro-benzenesulfonyl)-phenyl]-pyrrolidine-1-carboxylic acid tert-butyl ester (83 mg, 1.638 mmol) was dissolved in 3 ml of $CH_2Cl_2$. TFA (0.5 ml) was added and the mixture was stirred for 5 hours. The solution was concentrated under reduced pressure to give dimethyl-carbamic acid 5-(3-fluoro-benzenesulfonyl)-2-pyrrolidin-3-yl-benzyl ester, MS (M+H)=407.

Example 20

5-(3-Fluoro-benzenesulfonyl)-2-pyrrolidin-3-yl-benzoic acid

The synthetic procedure described in this Preparation was carried out using the procedure of Scheme CC.

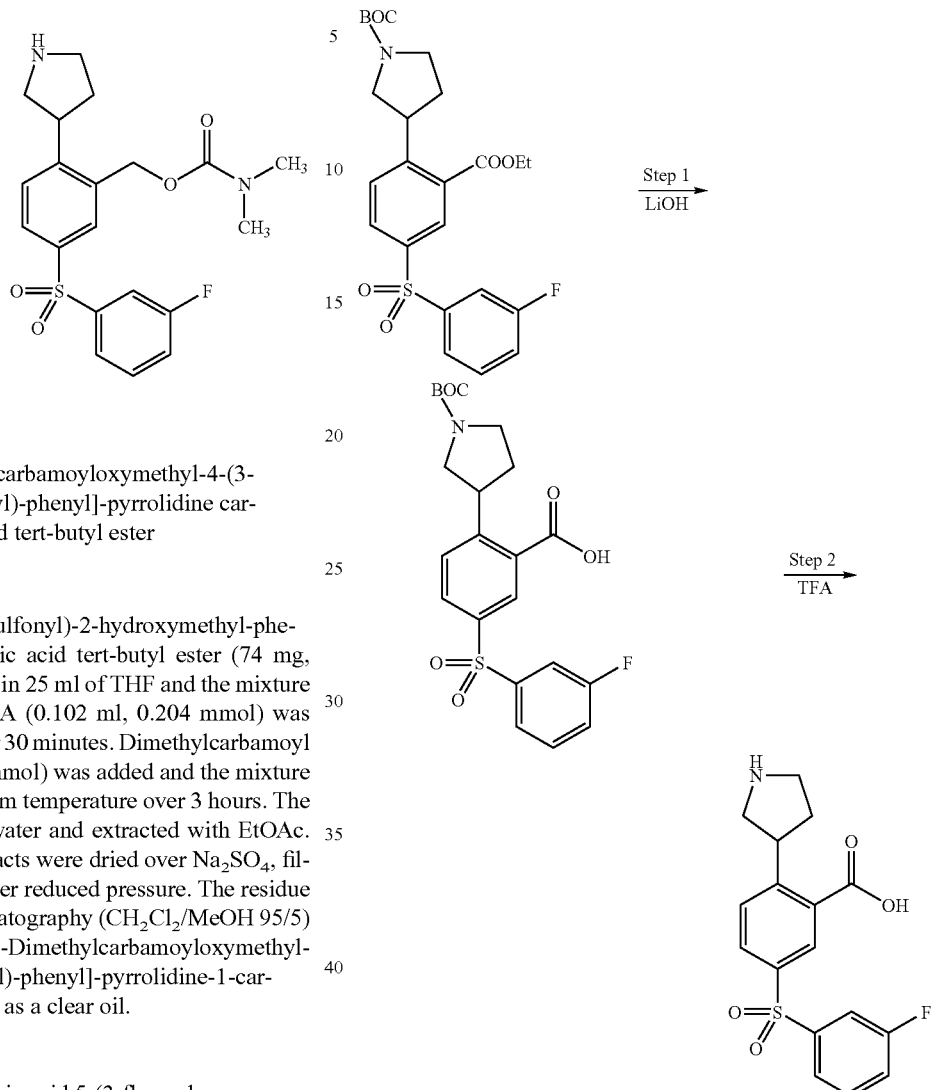

SCHEME CC

Step 1 3-[2-Carboxy-4-(3-fluoro-benzenesulfonyl)-phenyl]-pyrrolidine-1-carboxylic acid tert-butyl ester 3-[2-Ethoxycarbonyl-4-(3-fluoro-benzenesulfonyl)-phenyl]-pyrrolidine-1-carboxylic acid tert-butyl ester (290 mg, 0.607 mmol) was dissolved in 3 ml of MeOH. LiOH hydrate (76 mg, 1.821 mmol) was dissolved in 1 ml of water and added to the reaction mixture and allowed to stir for 4 hours. The MeOH was removed under reduced pressure. The aqueous residue was washed with $Et_2O$ and then acidified with 3N HCl to give a white precipitate which was filtered and dried to give 270 mgs (99%) of 3-[2-Carboxy-4-(3-fluoro-benzenesulfonyl)-phenyl]-pyrrolidine-1-carboxylic acid tert-butyl ester as a white powder.

Step 2 5-(3-Fluoro-benzenesulfonyl)-2-pyrrolidin-3-yl-benzoic acid

3-[2-Carboxy-4-(3-fluoro-benzenesulfonyl)-phenyl]-pyrrolidine-1-carboxylic acid tert-butyl ester (75 mg, 0.167 mmol) was dissolved in 3 ml of $CH_2Cl_2$. TFA (0.5 ml) was added and the mixture was stirred for 4 hours. The solution was concentrated under reduced pressure. The residue was crystallized from MeOH to give 59 mgs (quantitative) of 5-(3-Fluoro-benzenesulfonyl)-2-pyrrolidin-3-yl-benzoic acid as a white powder, MS (M+H)=350.

Example 17

Formulations

Pharmaceutical preparations for delivery by various routes are formulated as shown in the following Tables. "Active ingredient" or "Active compound" as used in the Tables means one or more of the Compounds of Formula I.

Composition for Oral Administration

| Ingredient | % wt./wt. |
|---|---|
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Composition for Oral Administration

| Ingredient | % wt./wt. |
|---|---|
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Composition for Oral Administration

| Ingredient | Amount |
|---|---|
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

Parenteral Formulation

| Ingredient | % wt./wt. |
|---|---|
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Suppository Formulation

| Ingredient | % wt./wt. |
|---|---|
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Topical Formulation

| Ingredients | grams |
|---|---|
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

Example 18

Radioligand Binding Studies

This example illustrates in vitro radioligand binding studies of compound of formula I.

The binding activity of compounds of this invention in vitro was determined as follows. Duplicate determinations of 5-$HT_6$ ligand affinity were made by competing for binding of [$^3$H]LSD in cell membranes derived from HEK293 cells stably expressing recombinant human 5-$HT_6$ receptor. Duplicate determinations of 5-$HT_{2A}$ ligand affinity were made by competing for binding of [$^3$H]Ketanserin (3-(2-(4-(4-fluorobenzoyl)piperidinol)ethyl)-2,4(1H,3H)-quinazolinedione) in cell membranes derived from CHO-K1 cells stably expressing recombinant human 5-$HT_{2A}$ receptor. Membranes were prepared from HEK 293 cell lines by the method described by Monsma et al., Molecular Pharmacology, Vol. 43 pp. 320-327 (1993), and from CHO-K1 cell lines as described by Bonhaus et al., Br J. Pharmacol. June; 115(4): 622-8 (1995).

For estimation of affinity at the 5-$HT_6$ receptor, all determinations were made in assay buffer containing 50 mM Tris-HCl, 10 mM $MgSO_4$, 0.5 mM EDTA, 1 mM ascorbic acid, pH 7.4 at 37° C., in a 250 microliter reaction volume. For estimation of affinity at the 5-$HT_{2A}$ receptor all determinations were made in assay buffer containing 50 mM Tris-HCl, 5 mM ascorbic acid, 4 mM $CaCl_2$, pH 7.4 at 32° C., in a 250 microliter reaction volume.

Assay tubes containing [$^3$H] LSD or [$^3$H]Ketanserin (5 nM), competing ligand, and membrane were incubated in a shaking water bath for 75 min. at 37° C. (for 5-$HT_6$) or 60 min. at 32° C. (for 5-$HT_{2A}$), filtered onto Packard GF-B plates (pre-soaked with 0.3% PEI) using a Packard 96 well cell harvester and washed 3 times in ice cold 50 mM Tris-HCl. Bound [$^3$H] LSD or [$^3$H]Ketanserin were determined as radioactive counts per minute using Packard TopCount.

Displacement of [$^3$H]LSD or [$^3$H]Ketanserin from the binding sites was quantified by fitting concentration-binding data to a 4-parameter logistic equation:

$$\text{binding} = \text{basal} + \left(\frac{B\max - \text{basal}}{1 + 10^{-\text{Hill}(\log[\text{ligand}] - \log IC_{50})}}\right)$$

where Hill is the Hill slope, [ligand] is the concentration of competing radioligand and $IC_{50}$ is the concentration of radioligand producing half-maximal specific binding of radioligand. The specific binding window is the difference between the Bmax and the basal parameters.

Using the procedures of this Example, compounds of Formula I were tested and found to be selective 5-$HT_6$ antagonists, selective 5-$HT_{2A}$ antagonists, or both. For example, the compound 4-[3-Fluoro-4-(1-methyl-(S)-pyrrolidin-3-yl)-benzenesulfonyl]-phenol exhibited a pKi of approximately 10.0 for the 5-HT6 receptor, and the compound 5-(3-Ethylsulfanyl-benzenesulfonyl)-2-pyrrolidin-3-yl-phenol exhibited a pKi of approximately 9.05 for the 5-HT2A receptor.

Example 19

Cognition Enhancement

The cognition-enhancing properties of compounds of the invention may be in a model of animal cognition: the object recognition task model. 4-month-old male Wistar rats (Charles River, The Netherlands) were used. Compounds were prepared daily and dissolved in physiological saline and tested at three doses. Administration was always given i.p. (injection volume 1 ml/kg) 60 minutes before T1. Scopolamine hydrobromide was injected 30 minutes after compound injection. Two equal testing groups were made of 24 rats and were tested by two experimenters. The testing order of doses was determined randomly. The experiments were performed using a double blind protocol. All rats were treated once with each dose condition. The object recognition test was performed as described by Ennaceur, A., Delacour, J., 1988, A new one-trial test for neurobiological studies of memory in rats. 1: Behavioral data. *Behav. Brain Res.* 31, 47-59.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound of formula I:

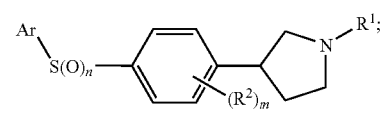

or a pharmaceutically acceptable salt thereof, wherein:
m is from 0 to 4;
n is from 0 to 2;
Ar is optionally substituted aryl or optionally substituted heteroaryl;
$R^1$ is:
  hydrogen;
  $C_{1-6}$alkyl;
  hetero-$C_{1-6}$alkyl; or
  —$(CH_2)_p$—X—$(CH_2)_q$—$R^a$;
  wherein:
    X is —C(O)— or —$SO_2$—;
    p and q each independently is 0 or 1; and
    $R^a$ is:
      $C_{1-6}$alkyl;
      $C_{1-6}$alkoxy;
      halo-$C_{1-6}$alkyl;
      halo-$C_{1-6}$alkoxy;
      hydroxy;
      amino;
      N—$C_{1-6}$alkyl-amino; or
      N,N-di-$C_{1-6}$alkylamino; and
each $R^2$ is independently:
  halo;
  $C_{1-6}$alkyl;
  halo-$C_{1-6}$alkyl;
  halo-$C_{1-6}$alkoxy;
  $C_{1-6}$alkoxy;
  hydroxy;
  hetero-$C_{1-6}$alkyl;
  cyano;
  nitro;
  amino;
  N—$C_{1-6}$alkyl-amino;
  N,N-di-$C_{1-6}$alkylamino; or
  —$(CH_2)_r$—Y—$(CH_2)_s$-Z-$(CH_2)_t$-Q-$(CH_2)_u$—$R^b$;

wherein
r, s, t and u each independently is 0 or 1;
Z is —C(O)— or —SO$_2$—;
X and Y each independently is —O—, —NR$^c$— or a bond;
R$^b$ is:
hydrogen;
C$_{1-6}$alkyl;
halo-C$_{1-6}$alkyl;
halo-C$_{1-6}$alkoxy;
C$_{1-6}$alkoxy;
hydroxy;
hetero-C$_{1-6}$alkyl;
cyano;
amino;
C$_{1-6}$alkyl-amino; or
N,N-di-C$_{1-6}$alkylamino; and
R$^c$ is:
hydrogen; or
C$_{1-6}$alkyl.

2. The compound of claim 1, wherein Ar is optionally substituted aryl.

3. The compound of claim 1, wherein Ar is optionally substituted heteroaryl.

4. The compound of claim 1, wherein Ar is optionally substituted phenyl.

5. The compound of claim 1, wherein Ar is indolyl, indazolyl, quinolinyl, pyrrolyl, pyridinyl, pyrimidinyl and dihydroindolonyl, each optionally substituted.

6. The compound of claim 1, wherein Ar is optionally substituted indolyl or optionally substituted indazolyl.

7. The compound of claim 1, wherein Ar is phenyl optionally substituted once, twice or three times with halo, C$_{1-6}$alkoxy, C$_{1-6}$alkylsulfonyl, C$_{1-6}$alkylsulfanyl, cyano, hydroxy, nitro, amino, or C$_{1-6}$alkyl.

8. The compound of claim 1, wherein Ar is phenyl substituted once with halo, C$_{1-6}$alkoxy or hydroxy.

9. The compound of claim 1, wherein R$^1$ is hydrogen or methyl.

10. The compound of claim 1, wherein n is 2.

11. The compound of claim 1, wherein m is 0 or 1 and R$^2$ is halo, C$_{1-6}$alkyl, C$_{1-6}$alkoxy, hydroxy, hydroxy-C$_{1-6}$alkoxy, hydroxy-C$_{1-6}$alkyl, cyano, —O—C(O)—R$^b$, —O—CH$_2$—C(O)—R$^b$, —C(O)—R$^b$ or —CH$_2$—C(O)—R$^b$.

12. The compound of claim 1, wherein m is 0 or 1 and R$^2$ is halo, C$_{1-6}$alkyl, C$_{1-6}$alkoxy, or hydroxy.

13. The compound of claim 1, wherein said compound is of formula II:

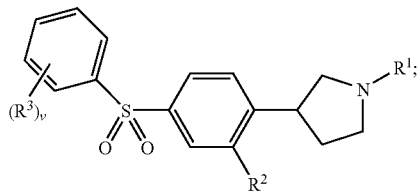

II and wherein:
v is from 1 to 4;
each R$^3$ is independently:
halo;
C$_{1-6}$alkyl;
halo-C$_{1-6}$alkyl;
halo-C$_{1-6}$alkoxy;
C$_{1-6}$alkoxy;
hydroxy;
hetero-C$_{1-6}$alkyl;
cyano;
nitro;
amino;
N—C$_{1-6}$alkyl-amino;
N,N-di-C$_{1-6}$alkylamino; or
—(CH$_2$)$_w$—S(O)$_x$—R$^d$;
wherein:
w is 0 or 1;
x is from 0 to 2;
R$^d$ is:
hydrogen;
C$_{1-6}$alkyl;
halo-C$_{1-6}$alkyl;
hydroxy;
hetero-C$_{1-6}$alkyl;
amino;
C$_{1-6}$alkyl-amino; or
N,N-di-C$_{1-6}$alkylamino; and
R$^1$ and R$^2$ are as recited in claim 1.

14. The compound of claim 13, wherein said compound is of formula IIa or IIb:

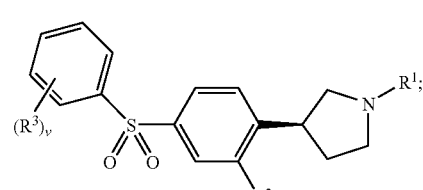

IIa

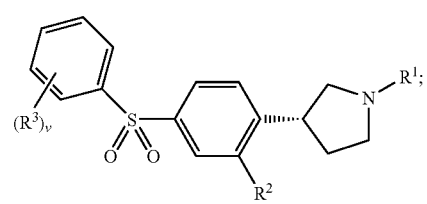

IIa and wherein v, R$^1$, R$^2$ and R$^3$ are as recited in claim 12.

15. The compound of claim 1, wherein said compound is of formula II:

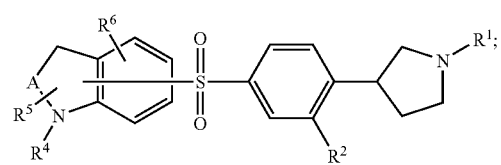

II and wherein:
A is C or N;
R$^4$ is:
hydrogen; or
C$_{1-6}$alkyl;
R$^5$ and R$^6$ each is independently:
halo;
C$_{1-6}$alkyl;
halo-C$_{1-6}$alkyl;
halo-C$_{1-6}$alkoxy;

$C_{1-6}$alkoxy;
hydroxy;
hetero-$C_{1-6}$alkyl;
cyano;
nitro;
amino;
$C_{1-6}$alkyl-amino;
N,N-di-$C_{1-6}$alkylamino;
—$(CH_2)_w$—$S(O)_x$—$R^d$; and
w, x, $R^1$, $R^2$ and $R^d$ are as recited in claim 1.

16. A pharmaceutical composition comprising an effective amount of the compound of claim 1 in admixture with a pharmaceutically acceptable carrier.

* * * * *